US008232390B2

(12) United States Patent
Capito et al.

(10) Patent No.: US 8,232,390 B2
(45) Date of Patent: Jul. 31, 2012

(54) PENTACYCLIC INDOLE DERIVATIVES AS ANTIVIRAL AGENTS

(75) Inventors: Elena Capito, Rome (IT); Joerg Habermann, Rome (IT); Frank Narjes, Rome (IT); Maria del Rosario Rico Ferreira, Rome (IT); Ian Stansfield, Rome (IT)

(73) Assignee: Istituto di Richerche di Biologia Molecolare P. Angeletti SpA, Rome (IT)

( * ) Notice: Subject to any disclaimer, the term of this patent is extended or adjusted under 35 U.S.C. 154(b) by 675 days.

(21) Appl. No.: 12/299,833

(22) PCT Filed: May 4, 2007

(86) PCT No.: PCT/GB2007/050239
§ 371 (c)(1),
(2), (4) Date: Apr. 8, 2009

(87) PCT Pub. No.: WO2007/129119
PCT Pub. Date: Nov. 15, 2007

(65) Prior Publication Data
US 2010/0009959 A1    Jan. 14, 2010

(30) Foreign Application Priority Data
May 8, 2006  (GB) .................................. 0608928.8

(51) Int. Cl.
*C07D 225/04*  (2006.01)
*C07D 267/22*  (2006.01)
*C07D 223/14*  (2006.01)
*C07D 267/02*  (2006.01)
*A61K 31/55*  (2006.01)

(52) U.S. Cl. ........ 540/466; 540/467; 540/543; 540/544; 514/214.01

(58) Field of Classification Search ................... 540/466, 540/467, 543, 544
See application file for complete search history.

(56) References Cited

U.S. PATENT DOCUMENTS

| 5,206,382 | A | 4/1993 | Costa et al. |
| 7,153,848 | B2 | 12/2006 | Hudyma et al. |
| 2005/0119318 | A1 | 6/2005 | Hudyma et al. |
| 2005/0239767 | A1 | 10/2005 | Chan et al. |
| 2006/0100262 | A1 | 5/2006 | Conte et al. |
| 2007/0049593 | A1 | 3/2007 | Oka et al. |
| 2007/0060565 | A1 | 3/2007 | Meanwell et al. |

FOREIGN PATENT DOCUMENTS

| EP | 1719773 A1 | 11/2006 |
| WO | WO9300334 A1 | 1/1993 |
| WO | WO9637619 A1 | 11/1996 |
| WO | WO0068216 A1 | 11/2000 |
| WO | WO02059321 A2 | 8/2002 |
| WO | WO03099824 A1 | 12/2003 |
| WO | WO2004065367 A1 | 8/2004 |
| WO | WO2004087714 A1 | 10/2004 |
| WO | WO2005/080388 A1 | 9/2005 |
| WO | WO2005080399 A1 | 9/2005 |
| WO | WO2006007693 A1 | 1/2006 |
| WO | WO2006020082 A1 | 2/2006 |
| WO | WO2006029912 A1 | 3/2006 |
| WO | WO2006046030 A2 | 5/2006 |
| WO | WO2006046039 A2 | 5/2006 |
| WO | WO2006052013 A1 | 5/2006 |
| WO | WO2007029029 A2 | 3/2007 |
| WO | WO2007033032 A1 | 3/2007 |
| WO | WO2007033175 A1 | 3/2007 |
| WO | WO2007054741 A1 | 5/2007 |
| WO | WO2007129119 A1 | 11/2007 |
| WO | WO2007131966 A1 | 11/2007 |

OTHER PUBLICATIONS

Duane E. Rudisill & J. K. Stille, "Palladium-catalyzed synthesis of 2-substituted indoles," 54(25) J. Org. Chem. 5856-66 (2002).
Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).
Yuusaku Yokoyama et al., "Palladium-Catalyzed Reaction of 3-Bromoindole Derivative with Allyl Esters in the Presence of Hexa-n-butyldistannane," 31(8) Heterocycles 1505-11 (1990).
Makoto Satoh et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).
V. Lohmann et al., "Replication of Subgenomic Hepatitis C Virus RNAs in a Hepatoma Cell Line," 285 Science 110-13 (1999).
Volker Lohmann et al., "Selective stimulation of Hepatitis C Virus and Pestivirus NS5B RNA Polymerase Activity by GTP," 274(16) The Journal of Biological Chemistry 10807-15 (1999).
W. Clark Still et al., "Rapid Chromatographic Technique for Preparative Separations with Moderate Resolution," 43 (14) Journal of Organic Chemistry 2923-25 (1978).
J.M. Travins & F.A. Etzkorn, "Facile synthesis of D-amino acids from an L-serine-derived axiridine," 39 Tetrahedron Letters 9389-92 (1998).

(Continued)

*Primary Examiner* — Shengjun Wang
(74) *Attorney, Agent, or Firm* — Sheldon Heber; Jeffrey Bergman; Julie Lake

(57) ABSTRACT

The present invention relates to pentacyclic indole derivatives of formula (I): wherein A, Ar, $R^1$, $R^2$, W, X, Y and Z are defined herein, and pharmaceutically acceptable salts thereof, pharmaceutical compositions comprising them, and their use for the treatment or prevention of infection by hepatitis C virus.

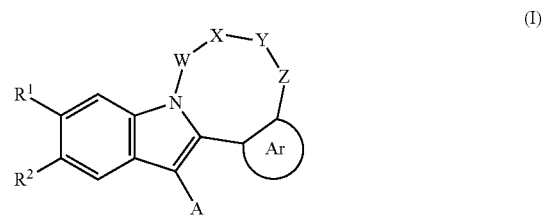

(I)

12 Claims, No Drawings

OTHER PUBLICATIONS

Tim Mosmann, "Rapid Colorimetric Assay for Cellular Growth and Survival: Application to Proliferation and Cytotoxicity Assays," 65 Journal of Immunological Methods 55-63 (1983).

Paul Blaney et al., "Fused and bridged bi- and tri-cyclic lactams via sequential metallo-azomethine ylide cycloaddition-lactamisation," 58(9) Tetrahedron 1719(37) (2002).

Jean-Yves Winum et al., "N-(tert-Butoxycarbonyl)-N-[4-(dimethylazaniumylidene)-1,4-dihydropyridin-1-ylsulfonyl] azanide: A New Sulfamoylating Agent. Structure and Reactivity toward Amines," 3(14) Organic Letters 2241-2243 (2001).

Eric P. Gillis & Martin D. Burke, "A Simple and Modular Strategy for Small Molecule Synthesis: Iterative Suzuki-Miyaura Coupling of B-Protected Haloboronic Acid Building Blocks," 129(21) Journal of the American Chemical Society 6716-17 (2007).

Ana Martinez et al., "Benzothiadiazine Dioxides (BTD) Derivatives as Non-nucleoside Human Cytomegalovirus (HCMV) Inhibitors. Study of Structural Requirements for Biological Activity," 11(11) Bioorganic & Medicinal Chemistry 2395-402 (2003).

A. Srikrishna et al., "Enantiospecific construciton of the BC-ring system of taxanes," 45(14) Tetrahedron Letters 2939-42 (2004).

Nathalie Goudreau & Montse Llinas-Brunet, "The therapeutic potential of NS3 protease inhibitors in HCV infection," 14(9) Expert Opinion on Investigational Drugs 1129-44 (2005).

Gennadiy Koev & Warren Kati, "The emerging field of HCV drug resistance," 17(3) Expert Opinion on Investigational Drugs 303-19 (2008).

R. Jennifer Randall, "Hepatitis C Virus Infection and Long-Term Survivors of Childhood Cancer: Issues for the Pediatric Oncology Nurse," 18(1) Journal of Pediatric Oncology Nursing 4-15 (2001).

Michael J. Szymonifka & James V. Heck, "The Synthesis and Reactions of 4-Carbomethoxy Betat-Sultams," 30 (22) Tetrahedron Letters 2869-72 (1989).

Albert Padwa et al., "Transmutation of 1,3-Dipoles. The Conversion of Alpha-Diazo Ketones into Azomethine Ylides via Carbonyl Ylides," 114(2) Journal of the American Chemical Society 593-601 (1992).

Gulam A. Bahadur et al., "The Reactions of Four Derivatives of Pyrrolo[1,2-a]indole with Arene-sulfonyl Azides," 12 Journal of the American Chemical Society: Perkins Transactions 1 2870-77 (1980).

"Prophylactic treatment from online medical dictionary," http://cancerweb.nc.ac.uk/cgi-bin/omd?prophylactic+treatment, accessed May 7, 2007.

Stacey R. Vlahakis, "Human Immunodeficiency Virus (HIV) Disease: Human Immunodeficiency Virus and Hepatitis C Virus Coinfection," 54(2) Lebanese Medical Journal 106-10 (2006).

T. Asselah et al., "Steatosis in Chronic Hepatitis C: Why Does It Really Matter," 55 Gut 123-30 (2006).

Caterina Ercolani et al., U.S. Appl. No. 11/666,583 (unpublished), 2008.

Iain Coldham & Richard Hufton, "Intramolecular Dipolar Cycloaddition Reactions of Azomethine Ylides," 105 Chemical Reviews 2765-2809 (2005).

Konstantinos Kordatos et al., "Novel Versatile Fullerene Synthons," 66 J. Org. Chem. 4915-20 (2001).

K. Ikegashira et al., "Discovery of Conformationally Constrained Tetracyclic Compounds as Potent Hepatitis C Virus NS5B RNA Polymerase Inhibitors," 49(11) Journal of Medicinal Chemistry 6950-53 (2006).

PENTACYCLIC INDOLE DERIVATIVES AS ANTIVIRAL AGENTS

CROSS-REFERENCE TO RELATED APPLICATIONS

This application is a National Stage application of International application PCT/GB2007/050239, filed May 4, 2007. This application also claims priority to British Provisional application GB 0608928.8, filed May 8, 2006.

FIELD OF THE INVENTION

The present invention relates to pentacyclic indole compounds, to pharmaceutical compositions containing them, to their use in the prevention and treatment of hepatitis C infections and to methods of preparation of such compounds and compositions.

BACKGROUND OF THE INVENTION

Hepatitis C(HCV) is a cause of viral infections. There is as yet no adequate treatment for HCV infection but it is believed that inhibition of its RNA polymerase in mammals, particularly humans, would be of benefit.

Published International patent application WO 2005/080399 (Japan Tobacco Inc.) discloses the following fused heterotetracyclic compounds:

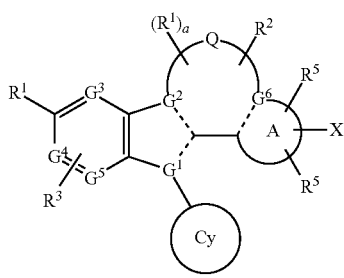

where A, X, Cy, $G^1$, $G^2$, $G^3$, $G^4$, $G^5$, $G^6$, $R^1$, $R^2$, $R^3$, $R^4$, $R^5$, $R^6$ and a are defined therein, and their use as HCV polymerase inhibitors.

Published International patent application WO 2006/020082 (Bristol-Myers Squibb Company) discloses the following fused tetracyclic compounds:

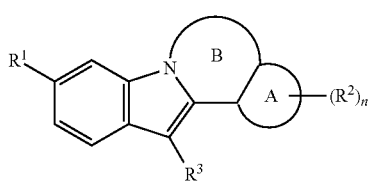

where A, B, $R^1$, $R^2$, $R^3$ and n are defined therein, and their use in treating hepatitis C.

SUMMARY OF THE INVENTION

The present invention provides the compound of the formula (I):

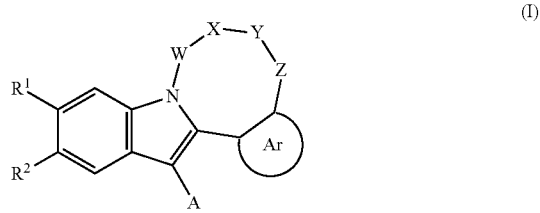

wherein

A is $C_{3-8}$cycloalkyl, optionally substituted by halogen, hydroxy, $C_{1-4}$alkyl or $C_{1-4}$alkoxy;

Ar is a moiety containing at least one aromatic ring and possesses 5, 6, 9 or 10 ring atoms, optionally containing 1, 2 or 3 heteroatoms independently selected from N, O and S, which ring is optionally substituted by groups $Q^1$ and $Q^2$;

$Q^1$ is halogen, hydroxy, $C_{1-6}$alkyl, $C_{1-6}$alkoxy, $(CH_2)_{0-3}$aryl, $(CH_2)_{0-3}$heteroaryl, $CONR^cR^d$, $(CH_2)_{0-3}NR^cR^d$, $O(CH_2)_{0-3}C_{3-8}$cycloalkyl, $O(CH_2)_{1-3}NR^cR^d$, $O(CH_2)_{0-3}CONR^cR^d$, $O(CH_2)_{0-3}CO_2H$, $O(CH_2)_{0-3}$aryl, $O(CH_2)_{0-3}$heteroaryl, $OCHR^eR^f$ or $O(CH_2)_{0-3}S(O)_2(CH_2)_{0-3}NR^cR^d$, where heteroaryl is optionally substituted by halogen or hydroxy;

$R^c$ and $R^d$ are independently selected from hydrogen, $C_{1-6}$alkyl and $C(O)C_{1-6}$alkyl;

or $R^c$ and $R^d$, together with the nitrogen atom to which they are attached, form a heteroaliphatic ring of 4 to 7 ring atoms, optionally containing 1 or 2 more heteroatoms independently selected from O and S and/or 1 or 2 groups independently selected from NH and $NC_{1-4}$alkyl, where said ring is optionally substituted by halogen, hydroxy, $C_{1-4}$alkyl or $C_{1-4}$alkoxy;

$R^e$ and $R^f$ fare independently selected from hydrogen, $C_{1-4}$alkyl and $C_{1-4}$alkoxy;

or $R^e$ and $R^f$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;

and where said $C_{1-4}$alkyl, $C_{1-4}$alkoxy and aryl groups are optionally substituted by halogen or hydroxy;

$Q^2$ is halogen, hydroxy, $C_{1-4}$alkyl or $C_{1-4}$alkoxy, where said $C_{1-4}$alkyl and $C_{1-4}$alkoxy groups are optionally substituted by halogen or hydroxy;

or $Q^1$ and $Q^2$ may be linked to form a ring of 4 to 7 atoms, where said ring optionally contains 1 or 2 heteroatoms independently selected from N, O and S, and is optionally substituted by halogen, hydroxy, $C_{1-4}$alkyl or $C_{1-4}$alkoxy;

one of $R^1$ and $R^2$ is $CO_2H$, $CO_2C_{1-6}$alkyl, $C(O)NR^3R^4$, $C(O)NHS(O)_2NR^aR^b$, $C(O)NHS(O)_2C_{1-6}$alkyl, $C(O)NHS(O)_2(CH_2)_{0-3}CO_2R^c$, $C(O)NHS(O)_2(CH_2)_{0-3}$aryl, tetrazolyl or hydroxyoxadiazolyl, and the other of $R^1$ and $R^2$ is hydrogen;

$R^a$ and $R^b$ are independently selected from hydrogen and $C_{1-6}$alkyl, or $R^a$ and $R^b$, together with the nitrogen atom to which they are attached, form a heteroaliphatic ring of 4 to 7 ring atoms, which ring may optionally contain 1 or 2 more heteroatoms independently selected from O and S and/or 1 or 2 groups independently selected from S(O), $S(O)_2$, NH and $NC_{1-4}$alkyl;

$R^3$ is hydrogen or $C_{1-4}$alkyl;
$R^4$ is hydrogen, $C_{1-4}$alkyl, $C_{2-4}$alkenyl, $(CH_2)_{0-3}$aryl, $(CH_2)_{0-3}$heteroaryl, $(CH_2)_{0-3}$Het or -L-$CO_2R^5$;
$R^5$ is hydrogen or $C_{1-4}$alkyl;
L is

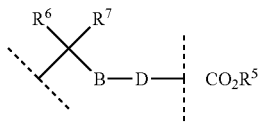

wherein $R^6$ and $R^7$ are independently selected from hydrogen, halogen, $C_{1-4}$alkyl, $C_{2-4}$alkenyl or $C_{1-4}$alkoxy;
or $R^6$ and $R^7$ are linked to form a $C_{3-8}$cycloalkyl group;
B is aryl, heteroaryl or $CONR^8R^9$, optionally substituted by halogen, $C_{1-4}$alkyl, $C_{2-4}$alkenyl or $C_{1-4}$alkoxy;
$R^8$ is hydrogen or $C_{1-6}$alkyl;
$R^9$ is aryl or heteroaryl;
or $R^8$, $R^9$ and the nitrogen atom to which they are attached form a 5- to 10-membered mono- or bi-cyclic ring system, where said ring may be saturated, partially saturated or unsaturated, and where said ring is optionally substituted by halogen, $C_{1-4}$alkyl, $C_{2-4}$alkenyl, $C_{2-4}$alkynyl or $C_{1-4}$alkoxy;
W is —$CH_2$— or —$CH_2CH_2$—;
Z is a bond, O or —$CH_2$—;
or Z and $Q^1$ are joined to form a non-aliphatic 5- or 6-membered ring optionally containing 1, 2 or 3 heteroatoms selected from N, O and S, which ring is optionally substituted by $C_{1-6}$alkyl;
X is a bond or —$CR^{14}R^{15}$;
Y is —$CH_2$— or —$CH_2CH_2$—;
$R^{14}$ and $R^{15}$, together with the carbon atom to which they are attached, form a heteroaliphatic ring of 4 to 7 ring atoms, which ring contains 1 or 2 heteroatoms selected from O and S, and/or 1 or 2 groups independently selected from S(O), $S(O)_2$ and $NR^{16}$, and which ring is optionally substituted by halogen, hydroxy, $C_{1-4}$alkyl or $C_{1-4}$alkoxy;
$R^{16}$ is hydrogen, $C_{1-6}$alkyl, $C_{2-6}$alkenyl, $C_{2-6}$alkynyl, $(CH_2)_{0-3}$-phenyl, $(CH_2)_{1-3}NR^{17}R^{18}$ or $C(O)(CH_2)_{1-3}NR^{17}R^{18}$;
$R^{17}$ and $R^{18}$ are independently selected from hydrogen, $C_{1-4}$alkyl or $(CH_2)_{1-3}$OH;
or $R^{17}$ and $R^{18}$, together with the nitrogen atom to which they are attached, form a heteroaliphatic ring of 4 to 7 atoms, which ring may optionally contain 1 or 2 more heteroatoms selected from O and S and/or 1 or 2 groups independently selected from S(O), $S(O)_2$, NH or $NC_{1-4}$alkyl, and which ring is optionally substituted by halogen, hydroxy, $C_{1-4}$alkyl or $C_{1-4}$alkoxy;
or X is $CHR^{19}$ and Y is $CHR^{20}$ or $NR^{20}$, where $R^{19}$ and $R^{20}$ are joined together to form a 5- to 7-membered ring, which ring may optionally contain 1 or 2 more heteroatoms selected from N, O and S and/or 1 or 2 groups independently selected from S(O), $S(O)_2$ or $NR^{21}$, and which ring is optionally substituted by halogen, hydroxy, oxo, $C_{1-4}$alkyl, $C_{1-4}$alkoxy, $(CH_2)_{0-3}N(R^{24})_2$, or $C(O)N(R^{24})_2$;
$R^{21}$ is hydrogen, $C_{1-4}$alkyl, $(CH_2)_{0-3}$heteroaryl, $C(O)(CHR^{25})CH_2NR^{22}R^{23}$, $(CH_2)_{1-3}NR^{22}R^{23}$, $(CH_2)_{0-1}C(O)(CH_2)_{1-3}NR^{22}R^{23}$ or $C(O)O(CH_2)_{1-3}NR^{22}R^{23}$ where $C_{1-4}$alkyl is optionally substituted by halogen or hydroxy;
$R^{22}R^{23}$ are independently selected from hydrogen, $C_{1-4}$alkyl and $C_{2-4}$alkenyl;
or $R^{22}R^{23}$, together with the nitrogen atom to which they are attached, form a heteroaliphatic ring of 4 to 7 atoms, which ring may optionally contain 1 or 2 more heteroatoms selected from O and S and/or 1 or 2 groups independently selected from S(O), $S(O)_2$, NH or $NC_{1-4}$alkyl;
each $R^{24}$ is independently selected from hydrogen, $C_{1-4}$alkyl and $(CH_2)_{1-3}NR^{17}R^{18}$; where one and only one of the moieties Z plus $Q^1$, X or X plus Y forms a ring;
$R^{25}$ is $C_{1-4}$alkyl;
and pharmaceutically acceptable salts thereof.

The present invention further provides the compound of the formula (Io):

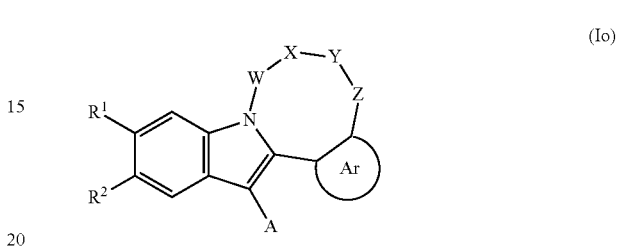

(Io)

wherein
A is $C_{3-8}$cycloalkyl, optionally substituted by halogen, hydroxy, $C_{1-4}$alkyl or $C_{1-4}$alkoxy;
Ar is a moiety containing at least one aromatic ring and possesses 5, 6, 9 or 10 ring atoms, optionally containing 1, 2 or 3 heteroatoms independently selected from N, O and S, which ring is optionally substituted by groups $Q^1$ and $Q^2$;
$Q^1$ is halogen, hydroxy, $C_{1-6}$alkyl, $C_{1-6}$alkoxy, $(CH_2)_{0-3}$aryl, $(CH_2)_{0-3}$heteroaryl, $CONR^cR^d$, $(CH_2)_{0-3}NR^cR^d$, $O(CH_2)_{0-3}C_{3-8}$cycloalkyl, $O(CH_2)_{1-3}NR^cR^d$, $O(CH_2)_{0-3}CONR^cR^d$, $O(CH_2)_{0-3}CO_2H$, $O(CH_2)_{0-3}$aryl, $O(CH_2)_{0-3}$heteroaryl, $OCHR^eR^f$ or $O(CH_2)_{0-3}S(O)_2(CH_2)_{0-3}NR^cR^d$;
$R^c$ and $R^d$ are independently selected from hydrogen, $C_{1-6}$alkyl and $C(O)C_{1-6}$alkyl;
or $R^c$ and $R^d$, together with the nitrogen atom to which they are attached, form a heteroaliphatic ring of 4 to 7 ring atoms, optionally containing 1 or 2 more heteroatoms independently selected from O and S and/or 1 or 2 groups independently selected from NH and $NC_{1-4}$alkyl, where said ring is optionally substituted by halogen, hydroxy, $C_{1-4}$alkyl or $C_{1-4}$alkoxy;
$R^e$ and $R^f$ are independently selected from hydrogen, $C_{1-4}$alkyl and $C_{1-4}$alkoxy;
or $R^e$ and $R^f$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;
and where said $C_{1-4}$alkyl, $C_{1-4}$alkoxy and aryl groups are optionally substituted by halogen or hydroxy;
$Q^2$ is halogen, hydroxy, $C_{1-4}$alkyl or $C_{1-4}$alkoxy, where said $C_{1-4}$alkyl and $C_{1-4}$alkoxy groups are optionally substituted by halogen or hydroxy;
or $Q^1$ and $Q^2$ may be linked to form a ring of 4 to 7 atoms, where said ring optionally contains 1 or 2 heteroatoms independently selected from N, O and S, and is optionally substituted by halogen, hydroxy, $C_{1-4}$alkyl or $C_{1-4}$alkoxy;
one of $R^1$ and $R^2$ is $CO_2H$, $CO_2C_{1-6}$alkyl, $C(O)NHS(O)_2NR^aR^b$, $C(O)NHS(O)_2C_{1-6}$alkyl, $C(O)NHS(O)_2(CH_2)_{0-3}CO_2R^c$, $C(O)NHS(O)_2(CH_2)_{0-3}$aryl, tetrazolyl or hydroxyoxadiazolyl,
and the other of $R^1$ and $R^2$ is hydrogen;
$R^a$ and $R^b$ are independently selected from hydrogen and $C_{1-6}$alkyl,
or $R^a$ and $R^b$, together with the nitrogen atom to which they are attached, form a heteroaliphatic ring of 4 to 7 ring atoms, which ring may optionally contain 1 or 2 more heteroatoms independently selected from O and S and/or 1 or 2 groups independently selected from S(O), S(O)$_2$, NH and NC$_{1-4}$alkyl;

W is —CH$_2$— or —CH$_2$CH$_2$—;

Z is a bond, O or —CH$_2$—;

or Z and Q$^1$ are joined to form a non-aliphatic 5- or 6-membered ring optionally containing 1, 2 or 3 heteroatoms selected from N, O and S, which ring is optionally substituted by C$_{1-6}$alkyl;

X is a bond or —CR$^{14}$R$^{15}$;

Y is —CH$_2$— or —CH$_2$CH$_2$—;

R$^{14}$ and R$^{15}$, together with the carbon atom to which they are attached, form a heteroaliphatic ring of 4 to 7 ring atoms, which ring contains 1 or 2 heteroatoms selected from O and S, and/or 1 or 2 groups independently selected from S(O), S(O)$_2$ and NR$^{16}$, and which ring is optionally substituted by halogen, hydroxy, C$_{1-4}$alkyl or C$_{1-4}$alkoxy;

R$^{16}$ is hydrogen, C$_{1-6}$alkyl, C$_{2-6}$alkenyl, C$_{2-6}$alkynyl, (CH$_2$)$_{0-3}$phenyl or (CH$_2$)$_{1-3}$NR$^{17}$R$^{18}$;

R$^{17}$ and R$^{18}$ are independently selected from hydrogen, C$_{1-4}$alkyl or (CH$_2$)$_{1-3}$OH;

or R$^{17}$ and R$^{18}$, together with the nitrogen atom to which they are attached, form a heteroaliphatic ring of 4 to 7 atoms, which ring may optionally contain 1 or 2 more heteroatoms selected from O and S and/or 1 or 2 groups independently selected from S(O), S(O)$_2$, NH or NC$_{1-4}$alkyl, and which ring is optionally substituted by halogen, hydroxy, C$_{1-4}$alkyl or C$_{1-4}$alkoxy;

or X is CHR$^{19}$ and Y is CHR$^{20}$ or NR$^{20}$, where R$^{19}$ and R$^{20}$ are joined together to form a 5- to 7-membered ring, which ring may optionally contain 1 or 2 more heteroatoms selected from N, O and S and/or 1 or 2 groups independently selected from S(O), S(O)$_2$ or NR$^{21}$, and which ring is optionally substituted by halogen, hydroxy, oxo, C$_{1-4}$alkyl, C$_{1-4}$alkoxy, (CH$_2$)$_{0-3}$N(R$^{24}$)$_2$, or C(O)N(R$^{24}$)$_2$;

R$^{21}$ is hydrogen, C$_{1-4}$alkyl or (CH$_2$)$_{1-3}$NR$^{22}$R$^{23}$;

R$^{22}$R$^{23}$ are independently selected from hydrogen and C$_{1-4}$alkyl;

or R$^{22}$R$^{23}$, together with the nitrogen atom to which they are attached, form a heteroaliphatic ring of 4 to 7 atoms, which ring may optionally contain 1 or 2 more heteroatoms selected from O and S and/or 1 or 2 groups independently selected from S(O), S(O)$_2$, NH or NC$_{1-4}$alkyl;

each R$^{24}$ is independently selected from hydrogen, C$_{1-4}$alkyl and (CH$_2$)$_{1-3}$NR$^{17}$R$^{18}$; where one and only one of the moieties Z plus Q$^1$, X or X plus Y forms a ring;

and pharmaceutically acceptable salts thereof.

DETAILED DESCRIPTION OF THE INVENTION

In one embodiment of the present invention, A is C$_{3-8}$cycloalkyl. Preferably, A is cyclopentyl or cyclohexyl. More preferably, A is cyclohexyl.

In another embodiment, Ar is a 5- or 6-membered aromatic ring optionally containing 1 or 2 heteroatoms independently selected from N, O and S, which ring is optionally substituted by Q$^1$ as hereinbefore defined. Preferably, Ar is phenyl, pyridyl, pyridazinyl, pyrimidinyl, pyrazinyl, thienyl, furanyl, pyrazolyl or imidazolyl, optionally substituted by Q$^1$ as hereinbefore defined.

When Q$^1$ is present, preferably Q$^1$ is halogen, hydroxy, C$_{1-6}$alkyl, C$_{1-6}$alkoxy or O(CH$_2$)$_{0-3}$heteroaryl, where heteroaryl is optionally substituted by halogen or hydroxy. More preferably, Q$^1$ is fluorine, chlorine, bromine, hydroxy, C$_{1-4}$alkyl, C$_{1-4}$alkoxy or O(CH$_2$)$_{1-2}$heteroaryl, where heteroaryl is optionally substituted by halogen. Most preferably, Q$^1$ is fluorine, chlorine, hydroxy, methyl, methoxy or OCH$_2$heteroaryl, where heteroaryl is optionally substituted by chloro. Especially, Q$^1$ is fluorine, hydroxy, methoxy,

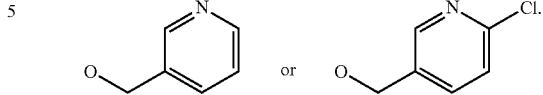

In another embodiment, one of R$^1$ and R$^2$ is CO$_2$H, CO$_2$C$_{1-6}$ alkyl or C(O)NR$^3$R$^4$, where R$^3$ and R$^4$ are as hereinbefore defined, and the other of R$^1$ and R$^2$ is hydrogen. Preferably, R$^1$ is CO$_2$H, CO$_2$C$_{1-6}$alkyl, CO$_2$CH$_2$phenyl or C(O)NHR$^4$ where R$^4$ is as hereinbefore defined, and R$^2$ is hydrogen. More preferably, R$^1$ is CO$_2$H, CO$_2$C$_{1-4}$alkyl or C(O)NH-L-CO$_2$R$^5$ where R$^5$ is as hereinbefore defined, and R$^2$ is hydrogen. Most preferably, R$^5$ is CO$_2$H, CO$_2$CH$_3$ or

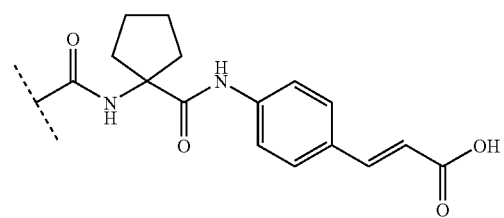

and R$^2$ is hydrogen.

In another embodiment, W is —CH$_2$—.

In another embodiment, Z is a bond or O.

In another embodiment, Z and Q$^1$ are joined to form a non-aliphatic 5- or 6-membered ring containing 1, 2 or 3 heteroatoms selected from N and O, which ring is optionally substituted by C$_{1-4}$alkyl. Preferably, Z and Q$^1$ are joined to form a non-aliphatic 5- or 6-membered ring containing 1 or 2 N atoms, which ring is optionally substituted by C$_{1-2}$alkyl. More preferably, Z and Q$^1$ are joined to form a non-aliphatic 5-membered ring containing 1 or 2 N atoms, which ring is optionally substituted by methyl.

In another embodiment, X is —CR$^{14}$R$^{15}$, where R$^{14}$ and R$^{15}$ are hereinbefore defined. Preferably, R$^{14}$ and R$^{15}$, together with the carbon atom to which they are attached, form a heteroaliphatic ring of 4 to 6 ring atoms, which ring contains an O or S atom and/or 1 or 2 groups independently selected from S(O), S(O)$_2$ and NR$^{16}$, where R$^{16}$ is as hereinbefore defined. More preferably, R$^{14}$ and R$^{15}$, together with the carbon atom to which they are attached, form a 4- or 5-membered heteroaliphatic ring, which ring contains an O atom and/or 1 or 2 NR$^{16}$ groups, where R$^{16}$ is as hereinbefore defined. Most preferably, R$^{14}$ and R$^{15}$, together with the carbon atom to which they are attached, form a 4-membered heteroaliphatic ring, which ring contains an O atom or an NR$^{16}$ group, where R$^{16}$ is as hereinbefore defined.

When R$^{16}$ is present, preferably R$^{16}$ is hydrogen, C$_{1-6}$alkyl, (CH$_2$)$_{0-3}$-phenyl, (CH$_2$)$_{1-3}$NR$^{17}$R$^{18}$ or C(O)(CH$_2$)$_{1-3}$NR$^{17}$R$^{18}$, where R$^{17}$ and R$^{18}$ are as hereinbefore defined. More preferably, R$^{16}$ is hydrogen, C$_{1-4}$alkyl, (CH$_2$)$_{1-2}$-phenyl, CH$_2$CH$_2$NR$^{17}$R$^{18}$ or C(O)(CH$_2$)$_{1-2}$NR$^{17}$R$^{18}$, where R$^{17}$ and R$^{18}$ are as hereinbefore defined. Most preferably, R$^{16}$ is hydrogen, $^i$propyl, CH$_2$-phenyl, CH$_2$CH$_2$NR$^{17}$R$^{18}$, C(O)CH$_2$N(CH$_3$)$_2$ or C(O)CH$_2$CH$_2$N(CH$_3$)$_2$, where R$^{17}$ and R$^{18}$ are as hereinbefore defined.

When R$^{16}$ is (CH$_2$)$_{1-3}$NR$^{17}$R$^{18}$, preferably R$^{17}$ and R$^{18}$ are independently selected from hydrogen, methyl, ethyl or CH$_2$CH$_2$OH. Alternatively, R$^{17}$ and R$^{18}$, together with the nitrogen atom to which they are attached, preferably form a 5- or 6-membered heteroaliphatic ring, which ring may optionally contain one O atom or a group selected from NH or NCH$_3$. More preferably, $R^{17}$ and $R^{18}$, together with the nitrogen atom to which they are attached, form a morpholinyl, pyrrolidinyl or piperazinyl ring, which piperazinyl ring is optionally N-substituted by methyl.

In another embodiment, X is CHR$^{19}$ and Y is CHR$^{20}$ where $R^{19}$ and $R^{20}$ are joined together to form a 5- or 6-membered ring, which ring may optionally contain one O atom and/or an NR$^{21}$ group, where $R^{21}$ is as hereinbefore defined, and which ring is optionally substituted by hydroxy, oxo, C$_{1-4}$alkoxy, CO$_2$H, (CH$_2$)CO$_2$H, NH$_2$, NH(C$_{1-4}$alkyl), (CH$_2$)$_{0-1}$N(C$_{1-4}$alkyl)$_2$ or C(O)N(C$_{1-4}$alkyl)$_2$. Preferably, $R^{19}$ and $R^{20}$ are joined together to form a 5- or 6-membered carbocyclic ring, optionally substituted by hydroxy or N(C$_{1-4}$alkyl)$_2$. More preferably, $R^{19}$ and $R^{20}$ are joined together to form a 5-membered carbocyclic ring, substituted by hydroxy or N(CH$_3$)$_2$.

In another embodiment, X is CHR$^{19}$ and Y is NR$^{20}$ where $R^{19}$ and $R^{20}$ are joined together to form a 5- or 6-membered ring, which ring may optionally contain one further heteroatom selected from N and O and/or an NR$^{21}$ group, where $R^{21}$ is as hereinbefore defined, and which ring is optionally substituted by hydroxy, oxo or C$_{1-4}$alkoxy. Preferably, $R^{19}$ and $R^{20}$ are joined together to form a 5- or 6-membered ring containing a further N atom or an NR$^{21}$ group, where $R^{21}$ is as hereinbefore defined and which ring is optionally substituted by hydroxy or oxo. More preferably, $R^{19}$ and $R^{20}$ are joined together to form either a 5-membered unsaturated ring containing a further N atom or a 6-membered ring containing an NR$^{21}$ group, where K is as hereinbefore defined, and which ring is optionally substituted by oxo.

When $R^{21}$ is present, preferably $R^{21}$ is (CH$_2$)$_{1-3}$NR$^{22}$R$^{23}$ where $R^{22}$ and $R^{23}$ are as hereinbefore defined. More preferably, $R^{21}$ is CH$_2$CH$_2$NR$^{22}$R$^{23}$ where $R^{22}$ and $R^{23}$ are as hereinbefore defined. Most preferably, $R^{21}$ is CH$_2$CH$_2$N(CH$_3$)$_2$.

In another embodiment, Y is —CH$_2$—.

One favoured group of compounds of the present invention is the compound of formula (Ia) and pharmaceutically acceptable salts thereof:

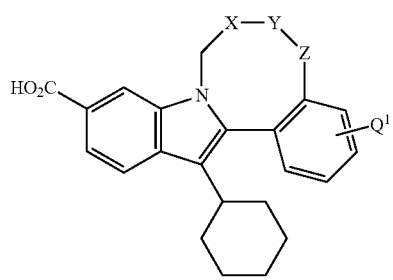
(Ia)

where X, Y, Z and Q$^1$ are as defined in relation to formula (I), where one and only one of the moieties Z plus Q$^1$, X or X plus Y forms a ring.

Preferably, X is —CR$^{14}$R$^{15}$—, where $R^{14}$ and $R^{15}$ are as hereinbefore defined. Preferably, $R^{14}$ and $R^{15}$, together with the carbon atom to which they are attached, form a 4-membered heteroaliphatic ring, which ring contains an O atom and/or an NR$^{16}$ group, where $R^{16}$ is as hereinbefore defined. Examples of suitable —CR$^{14}$R$^{15}$— groups include:

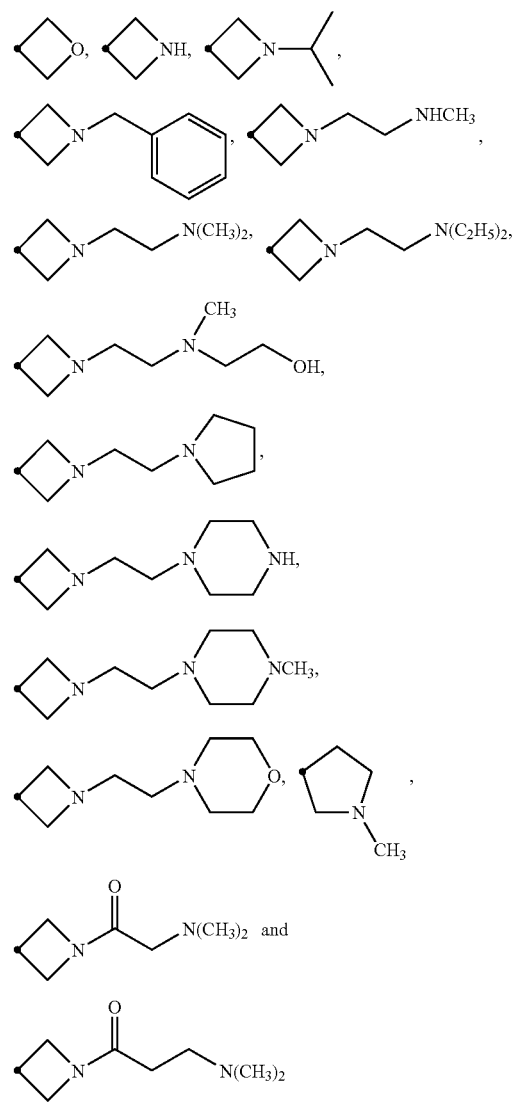

where • indicates the carbon atom of the —CR$^{14}$R$^{15}$— group.

Preferably, X is CHR$^{19}$ and Y is CHR$^{20}$ where $R^{19}$ and $R^{20}$ are joined together to form a 5- or 6-membered ring, which ring may optionally contain an NR$^{21}$ group, where $R^{21}$ is as hereinbefore defined, and which ring is optionally substituted by hydroxy, oxo, C$_{1-4}$alkoxy, (CH$_2$)$_{0-1}$CO$_2$H, (CH$_2$)$_{0-1}$N(R$^{24}$)$_2$ or C(O)N(R$^{24}$)$_2$, where $R^{24}$ is as hereinbefore defined. More preferably, $R^{19}$ and $R^{20}$ are joined to form a 5-membered carbocyclic ring, optionally substituted by hydroxy, oxo, CO$_2$H, CH$_2$CO$_2$H, NH$_2$, NH(C$_{1-2}$alkyl), N(C$_{1-2}$alkyl)$_2$, (CH$_2$)N(CH$_3$)$_2$ or C(O)N(CH$_3$)$_2$. Examples of suitable X plus Y moieties include:

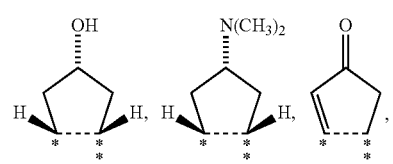

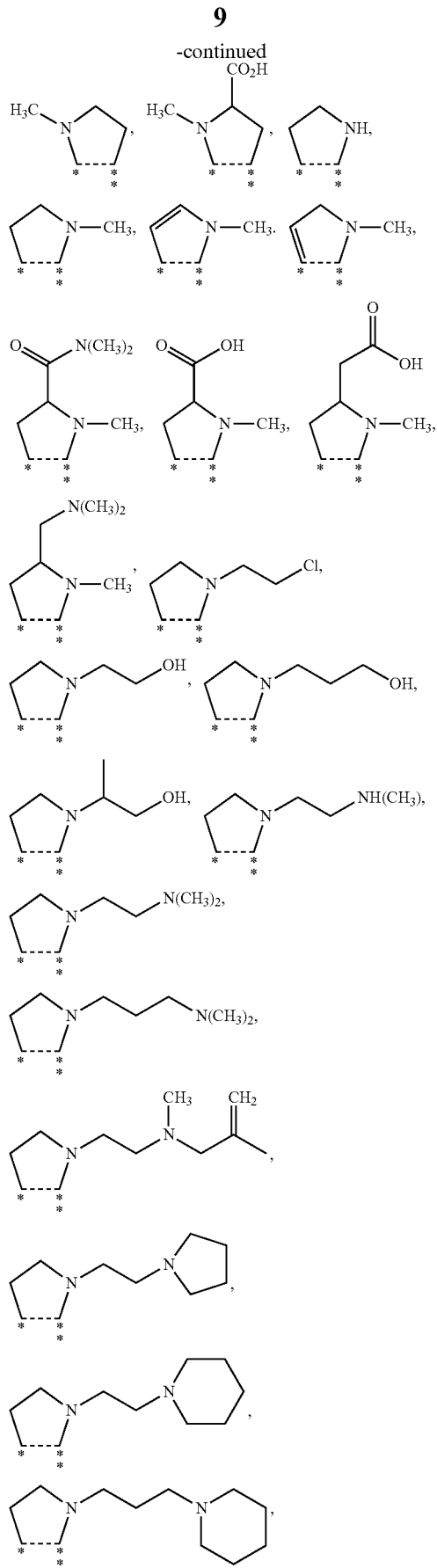
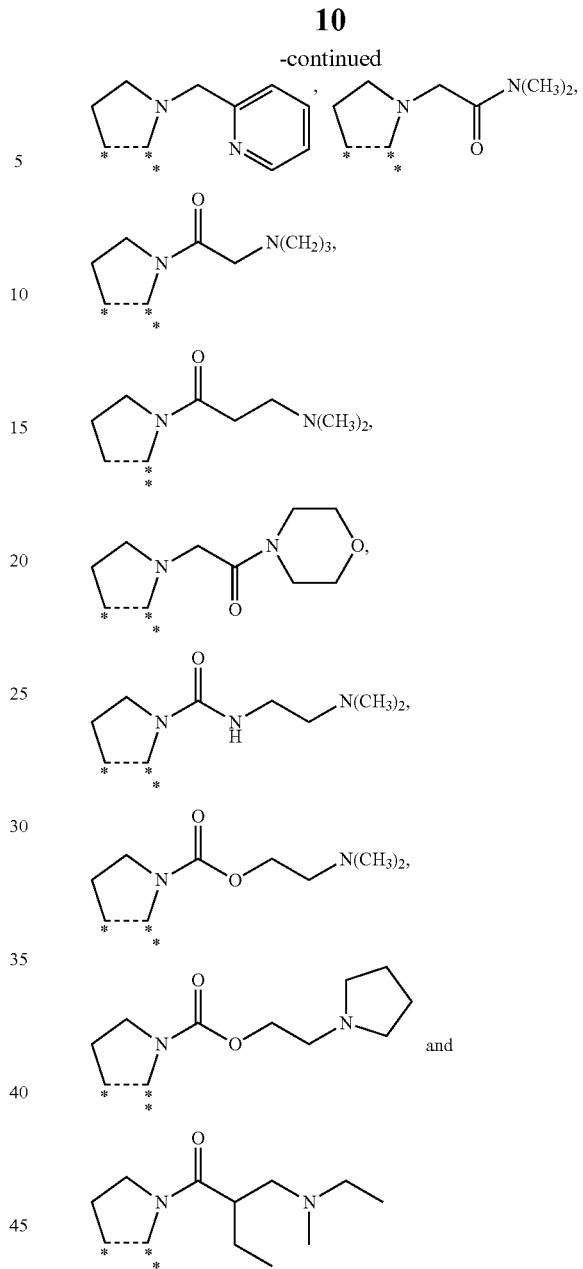

where * indicates the carbon atom of the group $X=CHR^{19}$ and ** indicates the carbon atom of the group $Y=CHR^{20}$ and the dotted line represents the single bond of the tetracyclic core that links X and Y.

Preferably, X is $CHR^{19}$ and Y is $NR^{20}$ where $R^{19}$ and $R^{20}$ are joined together to form a 5- or 6-membered ring, which ring may optionally contain a further N atom or an $NR^{21}$ group, where $R^{21}$ is as hereinbefore defined, and which ring is optionally substituted by hydroxy, oxo or $C_{1-4}$alkoxy. More preferably, $R^{19}$ and $R^{20}$ are joined together to form either a 5-membered unsaturated ring containing a further N atom or a 6-membered ring containing an $NR^{21}$ group, where $R^{21}$ is as hereinbefore defined, and which ring is optionally substituted by oxo.

Preferably, $R^{21}$ is $(CH_2)_{1-3}NR^{22}R^{23}$ where $R^{22}$ and $R^{23}$ are as hereinbefore defined. More preferably, $R^{21}$ is $CH_2CH_2N(C_{1-4}alkyl)_2$. Examples of suitable X plus Y moieties include:

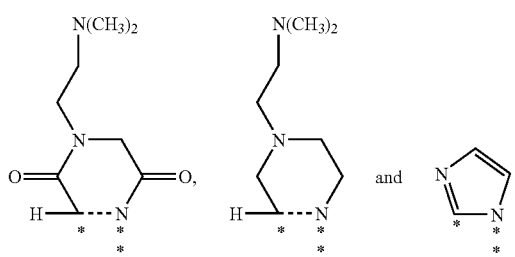

where * indicates the carbon atom of the group X═CHR$^{19}$ and ** indicates the nitrogen atom of the group Y═NR$^{20}$ and the dotted line represents the single bond of the tetracyclic core that links X and Y.

Preferably, Z and Q$^1$ are joined to form a non-aliphatic 5- or 6-membered ring optionally containing 1, 2 or 3 heteroatoms selected from N and O, which ring is optionally substituted by $C_{1-4}$alkyl. More preferably, Z and Q$^1$ are joined to form a non-aliphatic 5- or 6-membered ring containing 1 or 2 N atoms, which ring is optionally substituted by $C_{1-2}$alkyl. Examples of suitable Z plus Q$^1$ moieties include:

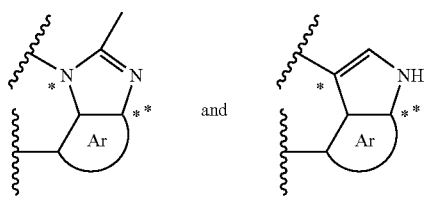

where * indicates the group Z and ** indicates the group Q$^1$.

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl, cyclopentyl or cyclohexyl. A suitable cycloalkylalkyl group may be, for example, cyclopropylmethyl.

As used herein, the term "alkenyl" as a group or part of a group means that the group is straight or branched. Examples of suitable alkenyl groups include vinyl and allyl.

When used herein, the term "halogen" means fluorine, chlorine, bromine and iodine.

When used herein, the term "aryl" as a group or part of a group means a carbocyclic aromatic ring. Examples of suitable aryl groups include phenyl and naphthyl.

When used herein, the term "heteroaryl" as a group or part of a group means a 5- to 10-membered heteroaromatic ring system containing 1 to 4 heteroatoms selected from N, O and S. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzothienyl, benzimidazolyl and quinolinyl.

When used herein, the term "Het" as a group or part of a group means a heteroaliphatic ring of 4 to 7 atoms, which ring may contain 1, 2 or 3 heteroatoms selected from N, O and S or a group S(O), S(O)$_2$, NH or NC$_{1-4}$alkyl.

Where a compound or group is described as "optionally substituted" one or more substituents may be present. Optional substituents may be attached to the compounds or groups which they substitute in a variety of ways, either directly or through a connecting group of which the following are examples: amine, amide, ester, ether, thioether, sulfonamide, sulfamide, sulfoxide, urea, thiourea and urethane. As appropriate an optional substituent may itself be substituted by another substituent, the latter being connected directly to the former or through a connecting group such as those exemplified above.

Specific compounds within the scope of this invention include those named in the Examples and Tables below and their pharmaceutically acceptable salts.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulfonic acid, maleic acid, succinic acid, acetic acid, citric acid, tartaric acid, carbonic acid, phosphoric acid or sulfuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulfate ester, or reduction or oxidation of a susceptible functionality.

The present invention includes within its scope solvates of the compounds of formula (I) and salts thereof, for example, hydrates.

The present invention also includes within its scope N-oxides of the compounds of formula (I).

The present invention also includes within its scope any enantiomers, diastereomers, geometric isomers and tautomers of the compounds of formula (I). It is to be understood that all such isomers and mixtures thereof are encompassed within the scope of the invention.

The present invention further provides a compound of formula (I) or a pharmaceutically acceptable salt thereof for use in therapy.

In another aspect, the invention provides the use of a compound of formula (I) as defined above, or a pharmaceutically acceptable salt thereof, for the manufacture of a medicament for treatment or prevention of infection by hepatitis C virus in a human or animal.

A further aspect of the invention provides a pharmaceutical composition comprising a compound of formula (I) as defined above, or a pharmaceutically acceptable salt thereof, in association with a pharmaceutically acceptable carrier. The composition may be in any suitable form, depending on the intended method of administration. It may for example be in the form of a tablet, capsule or liquid for oral administration, or of a solution or suspension for administration parenterally.

The pharmaceutical compositions optionally also include one or more other agents for the treatment of viral infections such as an antiviral agent, or an immunomodulatory agent such as α-, β- or γ-interferon.

In a further aspect, the invention provides a method of inhibiting hepatitis C virus polymerase and/or of treating or preventing an illness due to hepatitis C virus, the method involving administering to a human or animal (preferably mammalian) subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

The dosage rate at which the compound is administered will depend on a variety of factors including the activity of the specific compound employed, the metabolic stability and length of action of that compound, the age of the patient, body weight, general health, sex, diet, mode and time of administration, rate of excretion, drug combination, the severity of the particular condition and the host undergoing therapy. Suitable dosage levels may be of the order of 0.02 to 5 or 10 g per day, with oral dosages two to five times higher. For instance, administration of from 10 to 50 mg of the compound per kg of body weight from one to three times per day may be in order. Appropriate values are selectable by routine testing. The compound may be administered alone or in combination with other treatments, either simultaneously or sequentially. For instance, it may be administered in combination with effective amounts of antiviral agents, immunomodulators, anti-infectives or vaccines known to those of ordinary skill in the art. It may be administered by any suitable route, including orally, intravenously, cutaneously and subcutaneously. It may be administered directly to a suitable site or in a manner in which it targets a particular site, such as a certain type of cell. Suitable targeting methods are already known.

An additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

The present invention also provides a process for the preparation of compounds of formula (I).

General Synthetic Schemes

Conceptually, fused pentacycles could be assembled by using the Pauson-Khand reaction as key step for the construction of two of the five rings (Method A) or by an intramolecular dipolar cycloaddition (Method F).

Spirocyclic systems were suitably prepared by elaborating a pre-existing quaternary center on a tetracyclic system (Method B).

Further heteroatom-containing pentacycles could be prepared by one of the following methods starting from a 2-bromoindole intermediate:

(i) installation of a branched tether to link the indole nitrogen and the C2 aromatic, generating a tetracyclic system, with subsequent derivatisation of a tether atom and linking back to the tether branchpoint to set up the 5$^{th}$ fused ring (Method C)

(ii) coupling at C2 of an aromatic bearing precursor elements to both the 4$^{th}$ and 5$^{th}$ rings. As for Method C, the tether was first set up to link the C2 aromatic to the indole nitrogen and form the tetracycle. Subsequent functional group manipulation triggered cyclisation to give ring 5 (Method D).

(iii) cross-coupling of 2 pre-formed fused bicyclic systems, with subsequent ring closure to tether the 2 systems setting up the pentacycle (Method E);

These routes are outlined schematically below.

Method A

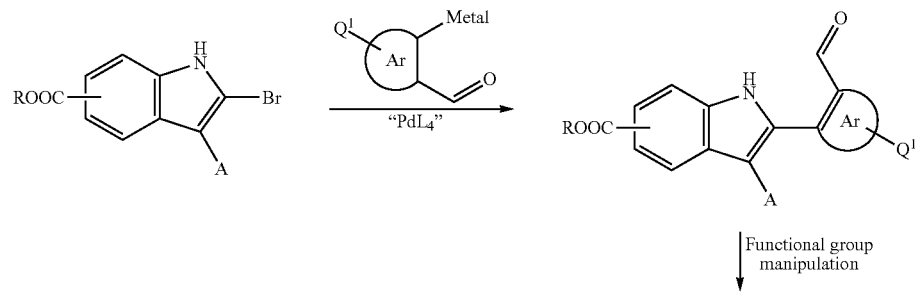

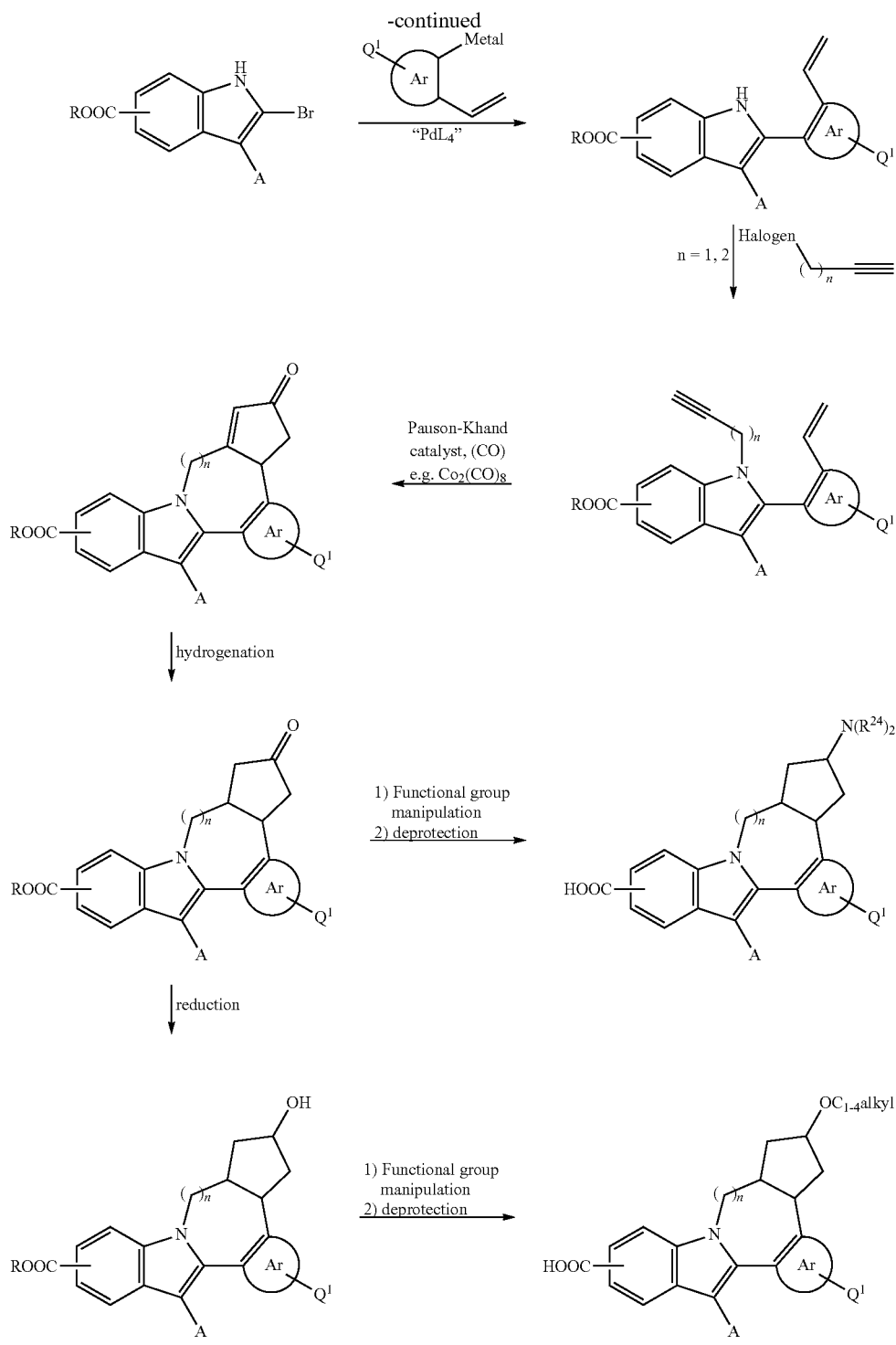

2-Bromoindole (prepared as described in published International patent application WO 2004/087714) was functionalised in position 2 with a suitable ortho-vinyl aryl moiety. Alternatively, a suitable ortho-formyl aryl moiety could be introduced and elaborated to give the ortho-vinyl moiety. The indole nitrogen could then be functionalised with a suitable ω-halogen alkyne to give the precursor for the Pauson-Khand reaction. This precursor could then be subjected to Pauson-Khand ring-closure conditions by reacting it in the presence of a suitable catalyst, such as dicobalt octacarbonyl (with or without the application of additional carbon monoxide pressure). The pentacyclic enone obtained could then be transformed into a ketone, the functionality of which could be diversely elaborated to give alcohols, (optionally substituted) ethers and (optionally substituted) amines. Ester deprotection then yielded the target pentacycle. Alternatively, it was possible to install the alkyne functionality as an ortho-substituent on the C2-aryl moiety and position the alkene on the indole nitrogen to obtain a Pauson-Khand precursor (not shown in the scheme).

Method B

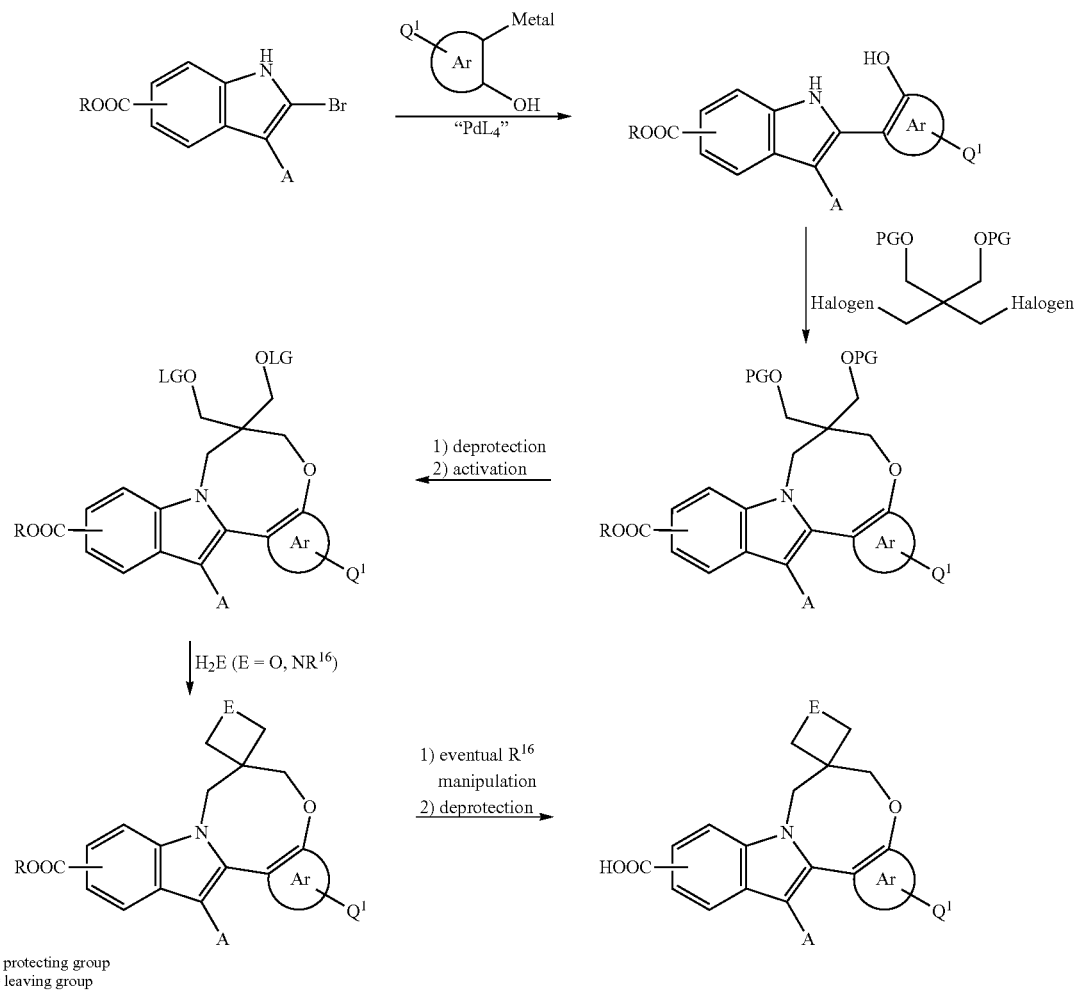

PG = protecting group
LG = leaving group

The spirocyclic systems were constructed by elaboration of a 2-bromoindole intermediate (prepared as described in published International patent application WO 2004/087714) with a suitable 2-hydroxyaryl moiety. The resulting 2-(2'-hydroxyaryl)indole could be reacted with a suitably protected 2,2-bis(bromomethyl)propane-1,3-diol, followed by cleavage of the protecting group(s). The diol could then be activated and reacted with suitably substituted nucleophiles. In the case of nitrogen nucleophiles, $R^{16}$ could also be a suitable protecting group (e.g. benzyl, thus $H_2NR^{16}$=benzylamine). Cleavage of this protecting group and attachment of an alternative $R^{16}$ group (via alkylation with $R^{16}$-halogen or reductive amination with $R^{16}$—CHO) allowed access to a wide variety of compounds. Ester deprotection then yielded the target indole carboxylic acids.

Method C

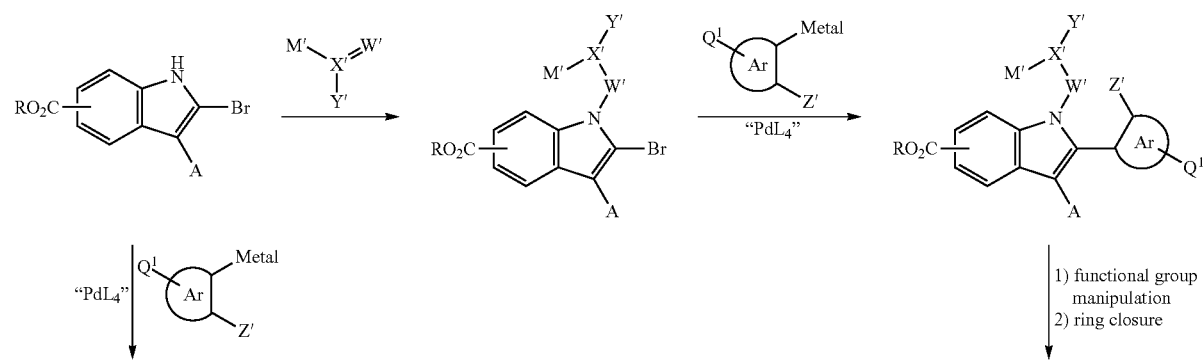

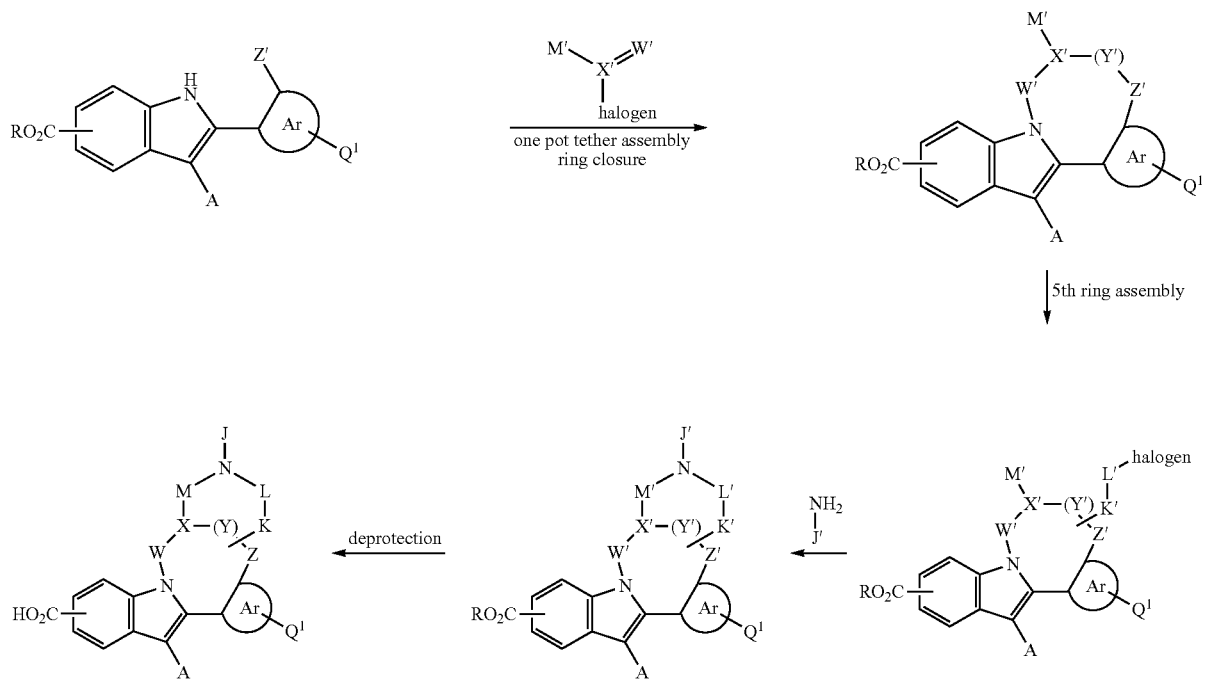

The C2 tethered tetracycle was assembled first, in one of 2 ways: via functionalisation on the indole nitrogen (e.g. conjugate addition to α,β-unsaturated ester) to introduce precursor functionality W'/X'/Y'/M' to any of the elements W/X/Y of the tether and M of what would become part of the 5$^{th}$ fused ring. Pd mediated cross-coupling methodology (e.g., Suzuki, Stille etc) then brought in a C2 aromatic bearing pre-cursor functionality Z' to the element Z of the tether. Functional group manipulation and ring closure afforded the tetracyclic system. Alternatively, the C2 functionality bearing Z' could be installed first and then the tether and branch elements W'/X'/M' introduced with concomitant cyclisation to the tetracycle (e.g. via tandem conjugate addition/alkylation). Installation (e.g. by acylation) of precursor functionality K'/L' to further elements K/L of the 5$^{th}$ ring afforded a suitable substrate for reaction with primary amines to introduce the sidechain J and effect closure of the final ring to give the pentacyclic system, followed by appropriate functional group manipulation.

Method D

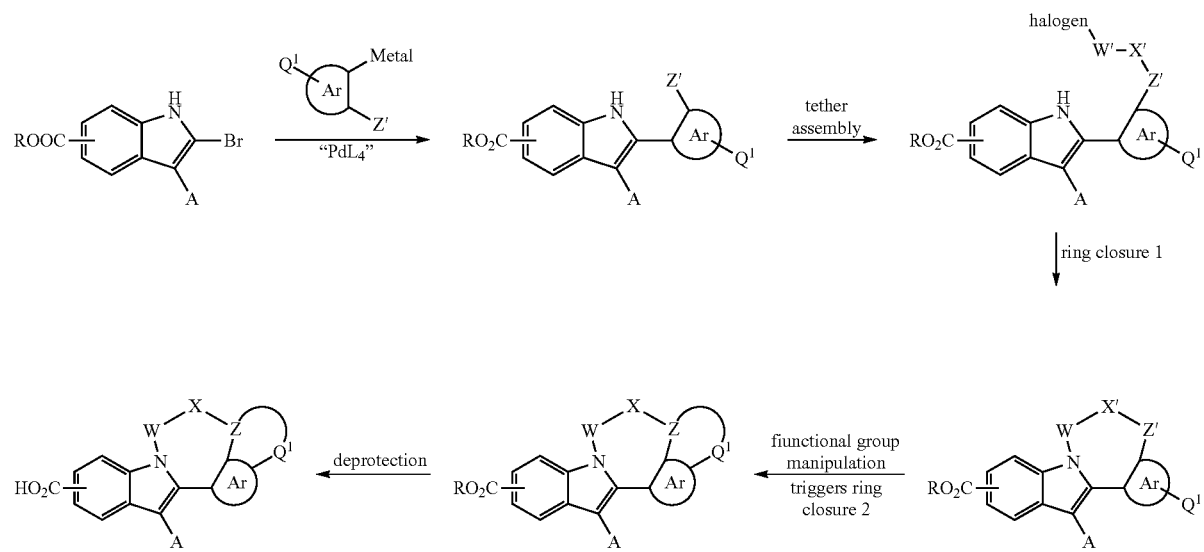

The C2 aromatic was introduced at the outset via Pd mediated cross-coupling methodology (Suzuki, Stille etc.), bringing with it precursor elements $Z'/Q^{1'}$ to both the $4^{th}$ and $5^{th}$ ring elements Z and $Q^1$. Precursor elements $X'/W'$ of the tether were then added (e.g. via acylation), with cyclisation (e.g. via alkylation) onto the indole nitrogen forming the tetracycle. Functional group manipulation (e.g. amide reduction) in the tether then triggered cyclisation (e.g. via dehydration) to set up the pentacycle. Ester deprotection then yielded the target pentacyclic indole carboxylic acids.

Method E

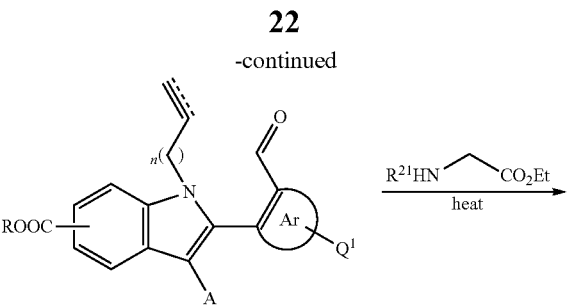

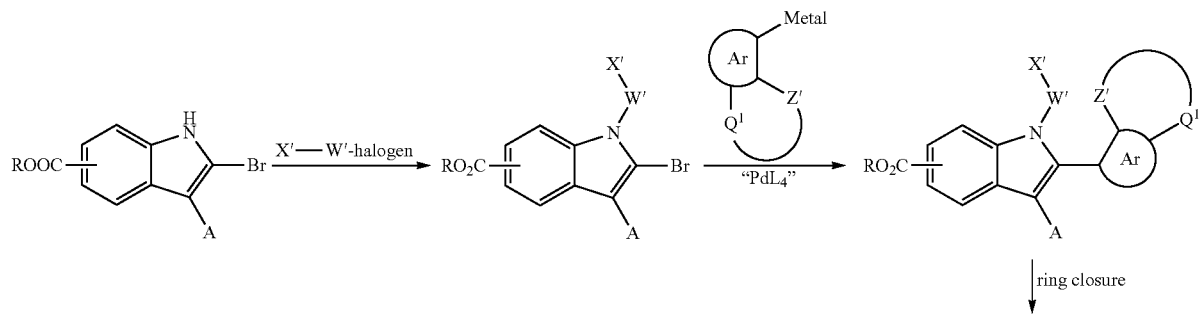

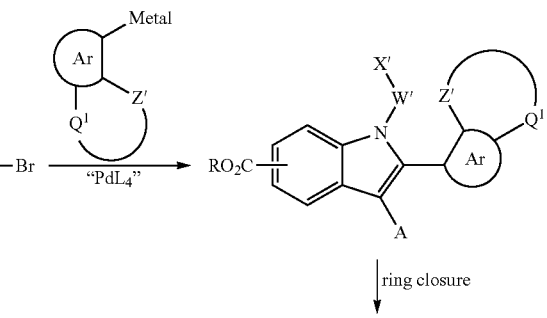

↓ ring closure

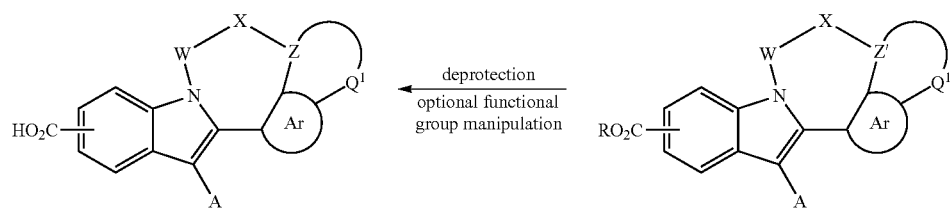

2-Bromoindole was functionalised on the indole nitrogen (e.g. via alkylation) to introduce precursor functionality W'/X' to either or both of the elements W/X of the tether. Pd mediated cross-coupling methodology (e.g., Suzuki, Stille etc.) then brought in a fused bicyclic C2 aromatic bearing precursor functionality Z' to the element Z of the tether. Ring closure (e.g. via Vilsmeier type acylation at Z') afforded the pentacyclic system. Ester deprotection then yielded the target pentacyclic indole carboxylic acids.

Method F

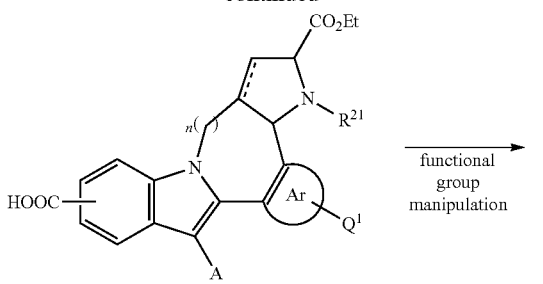

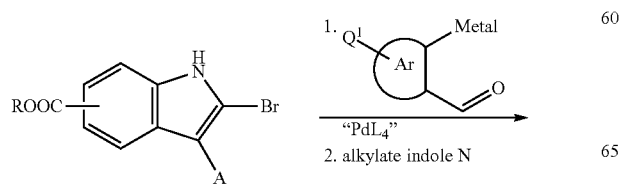

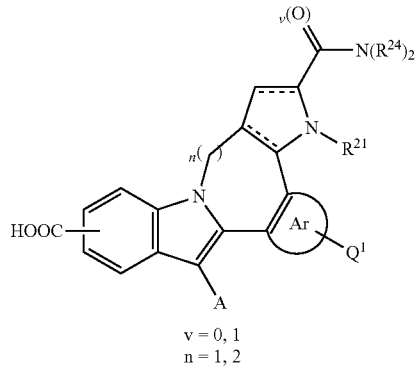

v = 0, 1
n = 1, 2

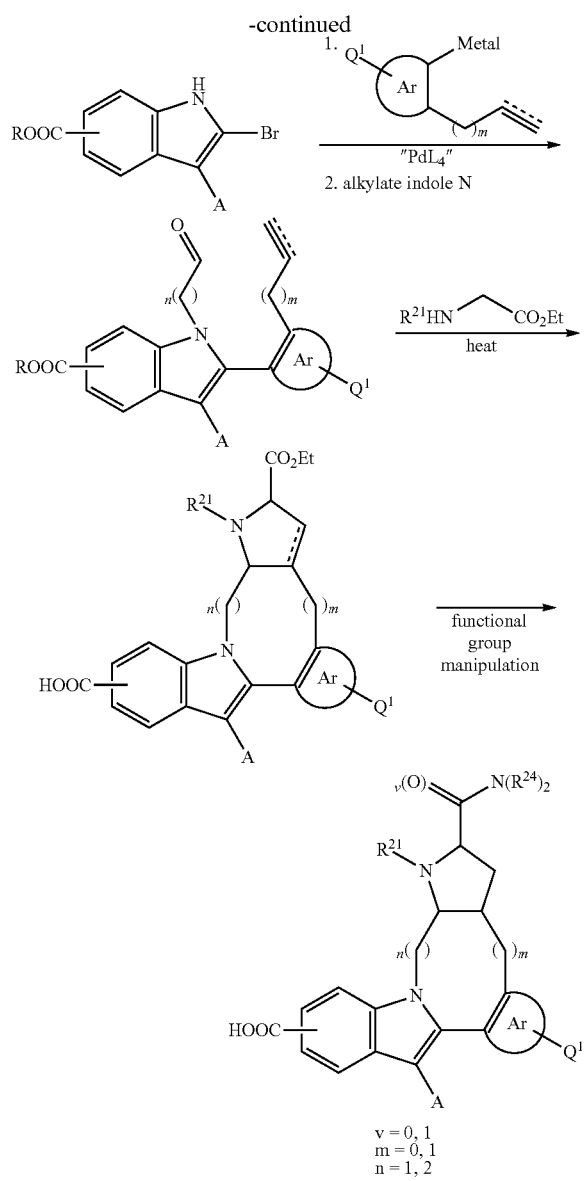

v = 0, 1
m = 0, 1
n = 1, 2

An intramolecular dipolar cycloaddition between a 1,3-dipole, which can be generated from an aldehyde and an amino ester, as shown in the first reaction sequence of Scheme F for N-functionalised glycine ethyl ester, and an alkenyl or alkynyl group (shown as a double bond with a dotted bond to denote the possible triple bond) can be used to construct the pentacyclic system (see I. Coldham, Chem. Rev. 2005, 102, 2765). Standard functional group manipulation (hydrogenation or dehydrogenation, amide formation, reduction of the amide to the amine) then leads to the target molecules. The cycloaddition can also be performed with the free amino acid instead of the amino ester, as shown in the second reaction in Scheme F.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known in the art.

The intermediates shown above are either known in the art or may be prepared by conventional methodology well known to one of ordinary skill in the art using, for instance, procedures described in the accompanying Examples, or by alternative procedures which will be readily apparent.

The skilled addressee will appreciate that compounds of formula (I) can be converted into other compounds of formula (I) using synthetic methodology well known in the art. Thus, for instance, the compound of formula (I) where $R^1$ is $CO_2CH_3$ may be converted into the compound of formula (I) where $R^1$ is $CO_2H$ by conversion of the ester to the carboxylic acid, for example, by treatment with $BBr_3$ in a suitable solvent, such as dichloromethane, or with NaOH in a suitable solvent, such as dioxane, THF and/or methanol.

Furthermore, the compound of formula (I) where $R^{16}$ is hydrogen may be converted into the compound of formula (I) where $R^{16}$ is $C(O)(CH_2)_{1-3}NR^{17}R^{18}$ by reaction with ($C_{1-6}$ alkyl)-O—$C(O)(CH_2)_{1-3}NR^{17}R^{18}$ in the presence of a base, such as DIPEA, and a coupling agent, such as HATU, in a suitable solvent, such as dichloromethane.

In addition, the compound of formula (I) where $Q^1$ is hydroxy may be converted into the compound of formula (I) where $Q^1$ is $OCH_2(CH_2)_{0-2}$heteroaryl by reaction with $ClCH_2(CH_2)_{0-2}$heteroaryl in the presence of a strong base, such as sodium hydride, in a suitable solvent, such as DMF.

Also, the compound of formula (I) where 1 is hydrogen may be converted in the compound of formula (I) where $R^{21}$ is $C(O)O(CH_2)_{1-3}NR^{22}R^{23}$ by reaction with an inorganic carbonate, such as potassium carbonate, and $ClCH_2(CH_2)_{0-2}NR^{22}R^{23}$ in a suitable solvent, such as DMF.

The following Examples are illustrative of this invention.

The compounds of the invention were tested for inhibitory activity against the HCV RNA dependent RNA polymerase (NS5B) in an enzyme inhibition assay (example i)) and in a cell based sub-genomic replication assay (example 11)). The compounds generally have IC50's below 1 µM in the enzyme assay and several examples have EC50's below 0.5 µM in the cell based assay.

i) In-vitro HCV NS5B Enzyme Inhibition Assay

Published International patent application WO 96/37619 describes the production of recombinant HCV RdRp from insect cells infected with recombinant baculovirus encoding the enzyme. The purified enzyme was shown to possess in vitro RNA polymerase activity using RNA as template. The reference describes a polymerisation assay using poly(A) and oligo(U) as a primer or an heteropolymeric template. Incorporation of tritiated UTP or NTPs is quantified by measuring acid-insoluble radioactivity. The present inventors have employed this assay to screen the various compounds described above as inhibitors of HCV RdRp.

Incorporation of radioactive UMP was measured as follows. The standard reaction (50 µl) was carried out in a buffer containing 20 mM tris/HCl pH 7.5, 5 mM $MgCl_2$, 1 mM DTT, 50 mM NaCl, 0.03% N-octylglucoside, 1 µCi [$^3$H]-UTP (40 Ci/mmol, NEN), 10 µM UTP and 10 µg/ml poly(A) or 5 µM NTPs and 5 µg/ml heteropolymeric template. Oligo(U)$_{12}$ (1 µg/ml, GENSET) was added as a primer in the assay working on Poly(A) template. The final NS5B enzyme concentration was 5 nM. The order of assembly was: 1) compound, 2) enzyme, 3) template/primer, 4) NTP. After 1 h incubation at 22° C. the reaction was stopped by adding 50 µl of 20% TCA and applying samples to DE81 filters. The filters were washed thoroughly with 5% TCA containing 1M $Na_2HPO_4/NaH_2PO_4$, pH 7.0, rinsed with water and then ethanol, air dried, and the filter-bound radioactivity was measured in the scintillation counter. Carrying out this reaction in the presence of various concentrations of each compound set out above allowed determination of $IC_{50}$ values by utilising the formula:

% Residual activity=$100/(1+[I]/IC_{50})^S$ where [I] is the inhibitor concentration and "s" is the slope of the inhibition curve.

ii) Cell based HCV Replication Assay

Cell clones that stably maintain subgenomic HCV replicon were obtained by transfecting Huh-7 cells with an RNA replicon identical to $I_{377}$neo/NS3-3'/wt described by Lohmann et al. (1999) (EMBL-GENBANK No. AJ242652), followed by selection with neomycin sulfate (G418). Viral replication was monitored by measuring the expression of the NS3 protein by an ELISA assay performed directly on cells grown in 96 wells microtiter plates (Cell-ELISA) using the anti-NS3 monoclonal antibody 10E5/24 (as described in published International patent application WO 02/59321. Cells were seeded into 96 well plates at a density of $10^4$ cells per well in a final volume of 0.1 ml of DMEM/10% FCS. Two hours after plating, 50 µl of DMEM/10% FCS containing a 3× concentration of inhibitor were added, cells were incubated for 96 hours and then fixed for 10 minutes with ice-cold isopropanol. Each condition was tested in duplicate and average absorbance values were used for calculations. The cells were washed twice with PBS, blocked with 5% non-fat dry milk in PBS+0.1% TRITON X100+0.02% SDS (PBSTS) and then incubated overnight at 4° C. with the 10E5/24 mab diluted in Milk/PBSTS. After washing 5 times with PBSTS, the cells were incubated for 3 hours at room temperature with Fc specific anti-mouse IgG conjugated to alkaline phosphatase (SIGMA), diluted in Milk/PBSTS. After washing again as above, the reaction was developed with p-Nitrophenyl phosphate disodium substrate (SIGMA) and the absorbance at 405/620 nm read at intervals. For calculations, data sets were used where samples incubated without inhibitors had absorbance values comprised between 1 and 1.5. The inhibitor concentration that reduced by 50% the expression of NS3 ($IC_{50}$) was calculated by fitting the data to the Hill equation, Fraction inhibition=$1-(A_i-b)/(A_0-b)=[I]^n/([I]^n+IC_{50})$ where:
Ai=absorbance value of HBI10 cells supplemented with the indicated inhibitor concentration.
A$_0$=absorbance value of HBI10 cells incubated without inhibitor.
b=absorbance value of Huh-7 cells plated at the same density in the same microliter plates and incubated without inhibitor.
n=Hill coefficient.

iii) General Procedures

All solvents were obtained from commercial sources (FLUKA, PURISS.) and were used without further purification. With the exception of routine deprotection and coupling steps, reactions were carried out under an atmosphere of nitrogen in oven dried (110° C.) glassware. Organic extracts were dried over sodium sulfate, and were concentrated (after filtration of the drying agent) on rotary evaporators operating under reduced pressure. Flash chromatography was carried out on silica gel following published procedure (W. C. Still et al., J. Org. Chem. 1978, 43, 2923) or on commercial flash chromatography systems (BIOTAGE corporation and JONES FLASHMASTER II) utilising pre-packed columns.

Reagents were usually obtained directly from commercial suppliers (and used as supplied) but a limited number of compounds from in-house corporate collections were utilised. In the latter case the reagents are readily accessible using routine synthetic steps that are either reported in the scientific literature or are known to those skilled in the art.

$^1$H NMR spectra were recorded on BRUKER AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; b, broad, and combinations thereof); coupling constant(s) in hertz (Hz); number of protons. Mass spectral (MS) data were obtained on a PERKIN ELMER API 100, or WATERS MICROMASS ZQ, operating in negative (ES$^-$) or positive (ES$^+$) ionization mode and results are reported as the ratio of mass over charge (m/z) for the parent ion only. Preparative scale HPLC separations were carried out on a WATERS DELTA PREP 4000 separation module, equipped with a Waters 486 absorption detector, on a mass-triggered automated WATERS FRACTION LYNX, or on a GILSON preparative system. In all cases compounds were eluted with linear gradients of water and MeCN both containing 0.1% TFA using flow rates between 15 and 40 mL/min.

The following abbreviations are used in the examples, the schemes and the tables: Ac: acetyl; aq.: aqueous; Ar: aryl; atm: atmosphere; cat.: catalytic; dioxan(e): 1,4-dioxane; dppf: (1,1'-bisdiphenylphosphino)ferrocene; 1,2-DCE: 1,2-dichloroethane; DCM: dichloromethane; DIPEA: diisopropylethyl amine; DMAP: N,N-dimethylpyridin-4-amine; DME: dimethoxyethane; DMF: N,N-dimethylformamide; DMSO: dimethylsulfoxide; DMP: Dess-Martin Periodinane; EDAC.HCl: 1-ethyl-(3-dimethylaminopropyl)carbodiimide HCl salt; eq.: equivalent(s); Et$_3$N: triethylamine; EtOAc: ethyl acetate; Et$_2$O: diethyl ether; EtOH: ethanol; h: hour(s); Et$_3$SiH: triethylsilane; HOAc: acetic acid; HATU: O-(7-azabenzotriazol-1-yl)-N,N,N', N'-tetramethyluronium hexafluorophosphate; Me: methyl; MeCN: acetonitrile; MeOH: methanol; min: minute(s); MS: mass spectrum; NBS: N-bromo succinimide; PE: petroleum ether; Ph: phenyl; quant.: quantitative; RP-HPLC: reversed phase high-pressure liquid chromatography; RT: room temperature; sec: second(s); SFC: Super-critical fluid chromatography; s.s.: saturated solution; TBTU: O-benzotriazol-1-yl-N,N,N',N'-tetramethyluronium tetrafluoroborate; TFA: trifluoroacetic acid; THF: tetrahydrofuran; THP: tetrahydropyranyl; TMS: trimethylsilyl.

EXAMPLE 1

10-cyclohexyl-2-(dimethylamino)-1,2,3,3a,4,14b-hexahydrocyclopenta[d]indolo[2,1-a][2]benzazepine-7-carboxylic acid

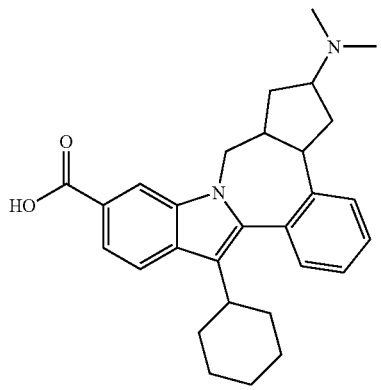

Step 1: Methyl 3-cyclohexyl-2-(2-vinylphenyl)-1H-indole-6-carboxylate 2-bromo-3-cyclohexyl indole-6-carboxylic acid methyl ester (1 eq., prepared as described in WO 2004/087714) was mixed with 2-vinyl benzene boronic acid (1.6 eq.) and bis (triphenylphosphine)palladium dichloride (0.15 eq.) was added. The mixture was degassed and dioxane and 2M aqueous sodium carbonate solution (5 eq.) were added. The mixture was heated under nitrogen atmosphere to 110° C. After 2 h all volatiles were removed in vacuo and the residual material was subjected to flash chromatography (PE:EtOAc, 10:1). After evaporation of the solvent the product was obtained as yellow crystals (83%). MS (ES$^+$): 360.4 (M+H$^+$).

Step 2: Methyl 3-cyclohexyl-1-prop-2-yn-1-yl-2-(2-vinylphenyl)-1H-indole-6-carboxylate Methyl 3-cyclohexyl-2-(2-vinylphenyl)-1H-indole-6-carboxylate was dissolved in DMF (0.277 M) and sodium hydride (1.2 eq.) was added. After the evolution of gas had ceased, a solution of propargylbromide in toluene (80% solution, 1.6 eq.) was added. After 3 h all volatiles were evaporated in vacuo. The residual material was purified by flash chromatography (PE:EtOAc, 20:1). After evaporation of the solvents, the product was obtained as a colourless foam (84%). MS (ES$^+$): 398.4 (M+H$^+$).

Step 3: Methyl 10-cyclohexyl-2-oxo-1,2,4,14b-tetrahydrocyclopenta[d]indolo[2,1-a][2]benzazepine-7-carboxylate Methyl 3-cyclohexyl-1-prop-2-yn-1-yl-2-(2-vinylphenyl)-1H-indole-6-carboxylate was dissolved in toluene (0.04 M), 4 Å molecular sieves were added and the mixture was flushed with argon. Dicobalt octacarbonyl (1.2 eq.) was added, the flushing procedure repeated and the mixture then left stirring for 1 h at RT. The flask was then immersed into an oil bath preheated to 110° C. After 5 h all volatiles were evaporated in vacuo. The residual material was subjected to flash chromatography (PE:EtOAc, 9:1). After evaporation of the solvents, a yellowish solid was obtained (36%). MS (ES$^+$): 426.4 (M+H$^+$).

Step 4: Methyl 10-cyclohexyl-2-oxo-1,2,3,3a,4,14b-hexahydrocyclopenta[d]indolo[2,1-a][2]benzazepine-7-carboxylate Methyl 10-cyclohexyl-2-oxo-1,2,4,14b-tetrahydrocyclopenta[d]indolo[2,1-a][2]benzazepine-7-carboxylate was dissolved in 2-propanol/EtOAc (1:5, 0.17 M), 10% palladium on carbon was added and after degassing, 1 atm hydrogen atmosphere was applied. After 5 h all volatiles were evaporated in vacuo and the residual material was purified by flash chromatography (PE:EtOAc, 8.5:1.5). After evaporation of the solvents the product was obtained as a colourless solid (67%). MS (ES$^+$): 428.4 (M+H$^+$).

Step 5: Methyl 10-cyclohexyl-2-(hydroxyimino)-1,2,3,3a,4,14b-hexahydrocyclopenta[d]indolo[2,1-a][2]benzazepine-7-carboxylate Methyl 10-cyclohexyl-2-oxo-1,2,3,3a,4,14b-hexahydrocyclopenta[d]indolo[2,1-a][2]benzazepine-7-carboxylate was dissolved in methanol/EtOAc (1:1, 0.024 M) and this solution was added to a solution of hydroxylamine hydrochloride (2 eq.) and sodium acetate (2 eq.) in water (0.4 M) kept at 60° C. The resulting mixture was left stirring at 60° C. for 2 h. All volatiles were evaporated in vacuo and the residual material was purified by flash chromatography (PE:EtOAc, 7:3). After evaporation of the solvents, the product was obtained as a colorless solid (83%). MS (ES$^+$): 443.4 (M+H$^+$).

Step 6: Methyl 2-amino-10-cyclohexyl-1,2,3,3a,4,14b-hexahydrocyclopenta[d]indolo[2,1-a][2]benzazepine-7-carboxylate Methyl 10-cyclohexyl-2-(hydroxyimino)-1,2,3,3a,4,14b-hexahydrocyclopenta[d]indolo[2,1-a][2]benzazepine-7-carboxylate was dissolved in acetic acid (0.016 M) and the solution added to platinum(IV) oxide. 50 psi hydrogen atmosphere were applied and the hydrogenation carried out for 3.5 h. The mixture was filtered and all volatiles were evaporated in vacuo. The product was obtained as a colourless solid (quant., 5:1-mixture of diastereomers). MS (ES$^+$): 429.5 (M+H$^+$).

Step 7: 10-cyclohexyl-2-(dimethylamino)-1,2,3,3a,4,14b-hexahydrocyclopenta[d]indolo[2,1-a][2]benzazepine-7-carboxylic acid Methyl 2-amino-10-cyclohexyl-1,2,3,3a,4,14b-hexahydrocyclopenta[d]indolo[2,1-a][2]benzazepine-7-carboxylate was dissolved in DCM (0.04 M) and the pH was adjusted with acetic acid to 4. A solution of formaldehyde in water (35%, 5 eq.) was added and the mixture was left stirring for 45 min. Sodium cyanoborohydride (5 eq.) was added and the mixture was left stirring at RT overnight. The mixture was diluted with DCM and extracted with sat. aqueous NaHCO$_3$ solution. The organic phase was dried over sodium sulfate and evaporated in vacuo. A colourless solid was obtained (94%, 5:1-mixture of diastereomers). The methyl 10-cyclohexyl-2-(dimethylamino)-1,2,3,3a,4,14b-hexahydrocyclopenta[d]indolo[2,1-a][2]benzazepine-7-carboxylate obtained was dissolved in MeOH/THF/water (1:1:0.5) to give a 0.3M solution. 1M aqueous KOH solution (10 eq.) was added and the mixture was warmed to 45° C. After 5 h the product was isolated by prep. RP-HPLC (W$_{ATERS}$ X-T$_{ERRA}$ column, 10% MeCN>99% MeCN, 0.1% TFA, 10 min). After lyophilisation a colourless solid was obtained (37%, single diastereomer). Structure elucidation indicated the rel-all-cis structure. $^1$H NMR (400 MHz, DMSO-d$_6$, 300 K) δ 8.15 (s, 1H), 7.90 (d, 1H, J 8.59), 6.54 (d, 1H, J 8.59), 7.50-7.42 (m, 4H), 4.61 (d, 1H, J 15.15), 3.76-3.70 (m, 2H), 2.82-2.70 (m, 8H), 2.26-2.19

(m, 1H), 2.18-2.02 (m, 4H), 1.90-1.87 (m, 1H), 1.75-1.72 (m, 2H), 1.57-1.39 (m, 4H), 1.24-1.15 (m, 1H); MS (ES+): 443.4 (M+H)+.

EXAMPLE 2

14'-cyclohexyl-1-isopropylspiro[azetidine-3,7'-indolo[1,2-e][1,5]benzoxazocine]-11'-carboxylic acid

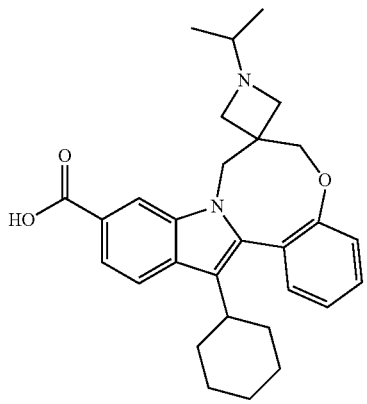

Step 1:
5,5-bis(bromomethyl)-2,2-dimethyl-1,3-dioxane

Para-toluenesulfonic acid monohydrate (0.1 eq) was added at 0° C. to a 0.2M solution of 2,2-bis(bromomethyl)propane-1,3-diol in acetone/2,2-dimethoxypropane (10:1) and the solution was stirred for 2 h at RT. Filtration over a pad of neutral alumina with EtOAc afforded the title compound as a white solid after evaporation of the solvent in vacuo (quant). $^1$H NMR (300 MHz, CDCl$_3$, 300 K) δ 3.80 (s, 4H), 3.58 (s, 4H), 1.42 (s, 6H).

Step 2: methyl 3-cyclohexyl-2-(2-hydroxyphenyl)-1H-indole-6-carboxylate

To a solution of methyl 2-bromo-3-cyclohexyl-1H-indole-6-carboxylate (prepared as described in WO2004/087714, from commercially available methyl indole-6-carboxylate) in a mixture of 1,2-dimethoxyethane and ethanol (5:2, v/v, 0.2 M) were added 2 eq of Na$_2$CO$_3$ (2 M aqueous solution), 1.3 eq of (2-hydroxyphenyl)boronic acid and 0.1 eq of tetrakis(triphenylphosphine)palladium(0). The mixture was degassed thoroughly with a stream of dry nitrogen and then heated to 100° C. overnight. The reaction mixture was allowed to cool, diluted with some EtOAc and filtered over a plug of CELITE. The filtrate was diluted with EtOAc and the organic phase washed with water, brine and dried over Na$_2$SO$_4$ before being filtered and concentrated in vacuo. The crude material was purified by flash chromatography on silica gel (1:7 EtOAc/petroleum ether, then 1:3) to afford the title compound as a light yellow solid (60%). $^1$H NMR (400 MHz, DMSO-d$_6$, 300 K) δ 1.14-1.38 (m, 3H), 1.63-1.81 (m, 5H), 1.82-1.96 (m, 2H), 2.62-2.70 (m, 1H), 3.84 (s, 3H), 6.92 (t, J 7.4, 1H), 7.00 (d, J 8.0, 1H), 7.22 (dd, J 1.3, 7.5, 1H), 7.26 (dt, J 1.4, 8.0, 1H), 7.57 (dd, J 1.2, 8.5, 1H), 7.78 (d, J 8.5, 1H), 7.98 (d, J 1.2, 1H), 9.69 (s, 1H), 11.22 (s, 1H); MS (ES+) m/z 350 (M+H)+.

Step 3: methyl 14'-cyclohexyl-2,2-dimethylspiro[1,3-dioxane-5,7'-indolo[1,2-e][1,5]benzoxazocine]-11'-carboxylate 5.0 eq of NaH (60% dispersion in mineral oil) was added to a degassed solution of the foregoing product in DMF (0.2 M) and the solution was allowed to stir for 20 min at RT. The mixture was then placed in an oil bath preheated at 70° C., a degassed 0.4M solution of 5,5-bis(bromomethyl)-2,2-dimethyl-1,3-dioxane (1.5 eq) in dry DMF was added and the mixture was stirred for 1 h; additional electrophile (1.5 eq) was added and stirring was continued for 3 h at 70° C. The reaction was quenched with aqueous saturated ammonium chloride solution, acidified with 1N HCl and extracted with Et$_2$O; the organic layer was washed with water and brine, dried over Na$_2$SO$_4$ and the solvent was removed in vacuo. The crude was purified by chromatography (PE/EtOAc) to afford the title compound (50%) and recovered starting material (44%). $^1$H NMR (400 MHz, CDCl$_3$, 300 K) δ 8.44 (s, 1H), 7.84 (d, 1H, J 8.5), 7.74 (dd, 1H, J 8.5, 1.3), 7.41 (b.t, 1H, J 7.8), 7.23 (dd, 1H, J 7.8, 1.7), 7.13-7.17 (m, 2H), 4.79 (d, 1H, J 15.3), 4.15 (d, 1H, J 12.5), 3.93 (s, 3H), 3.83 (d, 1H, J 11.8), 3.77 (d, 1H, J 12.5), 3.72 (d, 1H, J 15.3), 3.69 (d, 1H, J 12.3), 3.59 (d, 1H, J 11.8), 3.49 (d, 1H, J 12.3), 2.80-2.72 (m, 1H), 2.11-1.68 (m, 7H), 1.66 (s, 3H), 1.45 (s, 3H), 1.21-1.38 (m, 3H); MS (ES+) m/z 490 (M+H)+.

Step 4: 14'-cyclohexyl-1-isopropylspiro[azetidine-3,7'-indolo[1,2-e][1,5]benzoxazocine]-11'-carboxylic acid A catalytic amount of para-toluenesulfonic acid monohydrate was added to a suspension of methyl 14'-cyclohexyl-2,2-dimethylspiro[1,3-dioxane-5,7'-indolo[1,2e][1,5]benzoxazocine]-11'-carboxylate in MeOH/THF 1:2 (0.03 M), and the solution was stirred for 3 h at RT. Filtration over a pad of neutral alumina with EtOAc afforded after evaporation of the solvent in vacuo, methyl 14-cyclohexyl-7,7-bis(hydroxymethyl)-7,8-dihydro-6H-indolo[1,2-e][1,5]benzoxazocine-11-carboxylate (quant). Triflic anhydride (2.8 eq) was added at 0° C. to a solution of methyl 14-cyclohexyl-7,7-bis(hydroxymethyl)-7,8-dihydro-6H-indolo[1,2-e][1,5]benzoxazocine-11-carboxylate in dry MeCN (0.05M), DIPEA (3.0 eq) was added and the mixture was stirred for 15 min at 0° C., then further 3.0 eq of DIPEA were added, followed by iPrNH$_2$ (2 eq). The mixture was transferred into a closed vessel and stirring was continued at 70° C. for 4 h. EtOAc was added, the organic phase was washed with water and brine, dried over Na$_2$SO$_4$ and the solvent was removed in vacuo. The residue was hydrolysed with aqueous 1N KOH in dioxane (65° C., overnight); evaporation to dryness gave a residue that was purified by RP-HPLC to afford the title compound (4%). $^1$H NMR (300 MHz, DMSO-d$_6$, 330 K) δ 8.50 (s, 1H), 7.87 (d, 1H, J 8.3), 7.70 (d, 1H, J 8.3), 7.51-7.46 (m, 1H), 7.24-7.15 (m, 3H), 5.16 (b.d, 1H, J 15.9), 4.28 (d, 1H, J 12.7), 4.20 (d, ramethyluronium tetrafluoroborate; TFA: trifluoroacetic acid; THF: tetrahydrofuran; THP: tetrahydropyranyl; TMS: trimethylsilyl.

EXAMPLE 1

10-cyclohexyl-2-(dimethylamino)-1,2,3,3a,4,14b-hexahydrocyclopenta[d]indolo[2,1-a][2]benzazepine-7-carboxylic acid

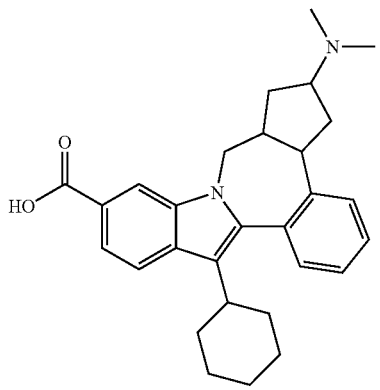

EXAMPLE 3

11-cyclohexyl-3-[2-(dimethylamino)ethyl]-1,2,3,4,4a,5-hexahydroindolo[1,2-d]pyrazino[1,2-a][1,4]benzodiazepine-8-carboxylic acid

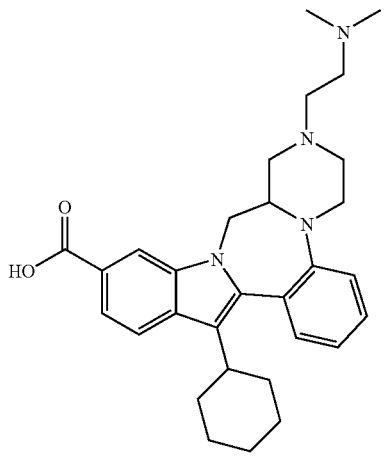

Step 1: methyl 2-(2-{[(tert-butoxycarbonyl)amino]phenyl}-3-cyclohexyl-1H-indole-6-carboxylate To a solution of methyl 2-bromo-3-cyclohexyl-1H-indole-6-carboxylate (prepared as described in WO 2004/087714, from commercially available methyl indole-6-carboxylate) in dioxane (0.07 M) was added 0.3 eq of bis(triphenylphosphine)palladium(II) dichloride at RT under a nitrogen atmosphere. Then 2 eq of aqueous $Na_2CO_3$ (2 M solution) followed by 2 eq tert-butyl[2-(4,4,5,5-tetramethyl-1,3,2-dioxaborolan-2-yl)phenyl]carbamate were added and the reaction flask immersed in a preheated oil bath at 100° C. for 2 h. The reaction mixture was allowed to cool and filtered. The filtrate was diluted with DCM and the organic phase washed with $H_2O$, brine and dried over $Na_2SO_4$ before being filtered and concentrated in vacuo. The crude material was purified by flash chromatography ($SiO_2$; 1:9 EtOAc/PE) to afford the title compound as a solid (69%). MS ($ES^+$) m/z 449 $(M+H)^+$.

Step 2: methyl 2-(2-aminophenyl)-3-cyclohexyl-1H-indole-6-carboxylate

TFA (137 eq) was added to a solution of methyl 2-(2-{[(tert-butoxycarbonyl)amino]phenyl}-3-cyclohexyl-1H-indole-6-carboxylate in DCM (0.1 M) at 0° C. and the solution was allowed to stir at RT for 1 h. The volatiles were removed in vacuo, and the residue diluted with EtOAc. The organic phase was washed with saturated aqueous $NaHCO_3$ (twice) and then brine. The organic phase was dried over $Na_2SO_4$, filtered and the solvent evaporated in vacuo to afford the title compound (quant.). MS ($ES^+$) m/z 349 $(M+H)^+$.

Step 3: dimethyl 13-cyclohexyl-6,7-dihydro-5H-indolo[1,2-d][1,4]benzodiazepine-6,10-dicarboxylate Methyl chloroacrylate (1.7 eq), triethylbutyl ammonium chloride (0.2 eq) and potassium carbonate (6 eq) were added to a solution of methyl 2-(2-aminophenyl)-3-cyclohexyl-1H-indole-6-carboxylate in dry MeCN (0.02 M). The mixture was heated at 60° C. overnight. The mixture was allowed to cool to RT, filtered and concentrated in vacuo. The residue was taken up in MeOH and 5 eq of trimethylsilyldiazomethane (2 N solution in hexanes) added dropwise. Volatiles were then removed in vacuo and the crude product was purified by flash chromatography ($SiO_2$; 2:8 EtOAc/PE) to afford the title compound as a solid (45%). MS ($ES^+$) m/z 433 $(M+H)^+$.

Step 4: dimethyl 5-(chloroacetyl)-13-cyclohexyl-6,7-dihydro-5H-indolo[1,2-d][1,4]benzodiazepine-6,10-dicarboxylate Chloroacetyl chloride (5 eq) was added to a sealed tube containing dimethyl 13-cyclohexyl-6,7-dihydro-5H-indolo[1,2-d][1,4]benzodiazepine-6,10-dicarboxylate (1 eq.). The mixture was heated at 40° C. overnight. The mixture was allowed to cool to RT before being diluted with EtOAc and washed with saturated aqueous $NaHCO_3$ and brine. The organic phase was dried over sodium sulfate, filtered and evaporated in vacuo to afford the title compound (quant.). MS ($ES^+$) m/z 509 $(M+H)^+$.

Step 5: methyl 11-cyclohexyl-3-[2-(dimethylamino)ethyl]-1,4-dioxo-1,2,3,4,4a,5-hexahydroindolo[1,2-d]pyrazino[1,2-a][1,4]-benzodiazepine-8-carboxylate N,N-dimethylethane-1,2-diamine (6 eq) and triethylamine (1 eq) were added to dimethyl 5-(chloroacetyl)-13-cyclohexyl-6,7-dihydro-5H-indolo[1,2-d][1,4]benzodiazepine-6,10-dicarboxylate in THF (0.04 M) and the mixture stirred at 50° C. for 2 nights. The solvent was then concentrated in vacuo and the mixture diluted with EtOAc before being washed with saturated aqueous $NaHCO_3$ and brine. The organic phase was dried over sodium sulfate, filtered and evaporated in vacuo to afford the title compound (65%). MS ($ES^+$) m/z 529 $(M+H)^+$.

Step 6: methyl 11-cyclohexyl-3-[2-(dimethylamino)
ethyl]-1,2,3,4,4a,5-hexahydroindolo[1,2-d]pyrazino
[1,2-a][1,4]benzodiazepine-8-carboxylate To a solution of methyl 11-cyclohexyl-3-[2-(dimethylamino)ethyl]-1,4-dioxo-1,2,3,4,4a,5-hexahydroindolo[1,2-d]pyrazino[1,2-a][1,4]benzodiazepine-8-carboxylate in THF (0.02 M), 10 eq of $BH_3$.THF (1 M solution in THF) was added and the solution allowed to stir at RT overnight. A further 10 eq of $BH_3$.THF (1 M solution in THF) were then added and the solution allowed to stir at RT for a further 24 h. The reaction was diluted carefully with MeOH (to bring the molarity to 0.02 M) and a 1.25 M solution HCl in MeOH was added (to give a final HCl molarity of 0.24 M). The reaction was heated at 70° C. overnight. The reaction was allowed to cool to RT before reducing the volume of the volatiles in vacuo and diluting with EtOAc. The organic phase was washed with saturated aqueous $NaHCO_3$ and brine, before being dried over $Na_2SO_4$, filtered and the solvent evaporated in vacuo to afford the title compound (quant). The material was then used in the next step without any further purification. MS ($ES^+$) m/z 501 (M+H)$^+$.

Step 7: 11-cyclohexyl-3-[2-(dimethylamino)ethyl]-1,
2,3,4,4a, 5-hexahydroindolo[1,2-d]pyrazino[1,2-a][1,
4]-benzodiazepine-8-carboxylic acid Methyl 11-cyclohexyl-3-[2-(dimethylamino)ethyl]-1,2,3,4,4a,5-hexahydroindolo[1,2-d]pyrazino[1,2-a][1,4]benzodiazepine-8-carboxylate was dissolved in a mixture of dioxane: $H_2O$ (1:1) (0.1 M) and to that solution 3 eq of an aqueous solution of KOH (5N) were added. The solution was stirred at 60° C. for 2 h. The mixture was cooled to RT and acidified with aqueous HCl (1N). The mixture was freeze dried and the residue purified by RP-HPLC (column WATERS X-TERRA prep. C18, 5 μm. Mobile phase: MeCN/$H_2O$ buffered with 0.1% TFA). Fractions containing the pure compound were combined and freeze dried to afford the title compound (10%). $^1$H NMR (400 MHz, DMSO-$d_6$+TFA, 330 K) δ 8.16 (s, 1H), 7.89 (d, 1H, J 8.4), 7.66 (d, 1H, J 8.4), 7.53-7.49 (m, 1H), 7.40-7.38 (m, 1H), 7.31-7.29 (m, 2H), 4.55-4.51 (m, 1H), 4.03-4.00 (m, 1H), 3.90-3.88 (m, 1H), 3.55-3.44 (m, 8H), 2.85-2.72 (m, 8H), 2.50-2.49 (m, 1H), 2.07-1.89 (m, 4H), 1.78-1.74 (m, 2H), 1.59-1.56 (m, 1H), 1.40-1.38 (m, 2H), 1.23-1.15 (m, 1H); MS ($ES^+$) m/z 487 (M+H)$^+$.

EXAMPLE 4

11-cyclohexyl-2-[2-(dimethylamino)ethyl]-1,2,3,4,
17,17a-hexahydro-6H-indolo[2,1-a]pyrazino[2,1-d]
[2,5]benzodiazocine-14-carboxylic acid

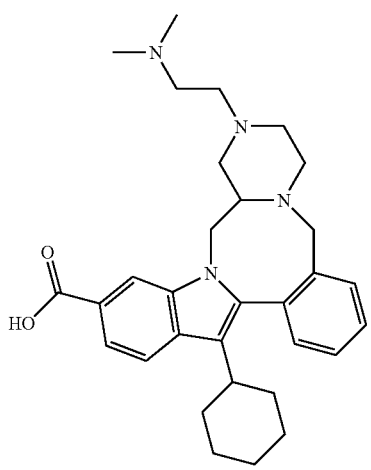

Step 1: methyl
2-[bis(tert-butoxycarbonyl)amino]acrylate

To a solution of methyl N-(tert-butoxycarbonyl)serinate in MeCN (0.9 M), 0.1 eq of DIPEA and 2.5 eq of di-tert-butyl dicarbonate were added and the mixture was stirred overnight at RT. Volatiles were removed in vacuo and the residue was taken up in EtOAc. The organic phase was washed with aqueous $NH_4Cl$, $NaHCO_3$ (s.s.) and then brine before being dried over $Na_2SO_4$, filtered and the solvent evaporated in vacuo to afford the title compound (quant). The material was used in the next step without any further purification. MS ($ES^+$) m/z 302 (M+H)$^+$.

Step 2: methyl 1-{2-[bis(tert-butoxycarbonyl)
amino]-3-methoxy-3-oxopropyl}-2-bromo-3-cyclo-
hexyl-1H-indole-6-carboxylate To a solution of methyl 2-bromo-3-cyclohexyl-1H-indole-6-carboxylate (prepared from commercially available methyl indole-6-carboxylate as described in WO 2004/087714) in MeCN (0.2 M), 6.0 eq of $K_2CO_3$ and 1.0 eq of methyl 2-[bis(tert-butoxycarbonyl)amino]acrylate were added and the mixture was stirred overnight at RT. The mixture was then filtered and the filtrate concentrated in vacuo to afford the title compound (98%). MS ($ES^+$) m/z 636 (M+H)$^+$, MS ($ES^+$) m/z 638 (M+H)$^+$.

Step 3: methyl 1-{2-[bis(tert-butoxycarbonyl)
amino]-3-methoxy-3-oxopropyl}-3-cyclohexyl-2-(2-
formylphenyl)-1H-indole-6-carboxylate To a solution of methyl 1-{2-[bis(tert-butoxycarbonyl)amino]-3-methoxy-3-oxopropyl}-2-bromo-3-cyclohexyl-1H-indole-6-carboxylate in dioxane (0.15 M) were added 6 eq of $Na_2CO_3$ (2 M aqueous solution), 1.5 eq (2-formylphenyl)boronic acid and 0.2 eq of bis(triphenylphosphine)palladium(II) dichloride. The mixture was heated at reflux for 1.5 h. The reaction mixture was filtered and then the filtrate was diluted with EtOAc. The organic phase was washed with $H_2O$, brine and dried over $Na_2SO_4$ before being filtered and concentrated in vacuo. The crude was purified by flash chromatography (Biotage cartridge, 1.0:9.0 EtOAc/PE) to afford the title compound (65%). MS ($ES^+$) m/z 663 (M+H)$^+$.

Step 4: methyl 1-(2-amino-3-methoxy-3-oxopropyl)-
3-cyclohexyl-2-(2-formylphenyl)-1H-indole-6-car-
boxylate To a solution of methyl 1-{2-[bis(tert-butoxycarbonyl)amino]-3-methoxy-3-oxopropyl}-3-cyclohexyl-2-(2-formylphenyl)-1H-indole-6-carboxylate in DCM (0.05 M) a large excess (>100 eq) of TFA was added and the solution stirred at RT for 20 min. Volatiles were removed in vacuo and the residue partitioned between EtOAc and aqueous $NaHCO_3$. The organic phase was washed with brine before being dried over $Na_2SO_4$, filtered and the solvent evaporated in vacuo to afford the title compound (quant). MS ($ES^+$) m/z 463 (M+H)$^+$.

Step 5: dimethyl 14-cyclohexyl-5,6,7,8-tetrahydroin-
dolo[2,1-a][2,5]benzodiazocine-7,11-dicarboxylate To a solution of methyl 1-(2-amino-3-methoxy-3-oxopropyl)-3-cyclohexyl-2-(2-formylphenyl)-1H-indole-6-carboxylate in 1,2-DCE (0.04 M), 2 eq of NaBH(OAc)$_3$ was added and the solution stirred overnight at RT. The reaction mixture was diluted with EtOAc. The organic phase was washed with $NaHCO_3$ (s.s.) and brine before being dried over $Na_2SO_4$, filtered and the solvent evaporated in vacuo to afford the title compound (quant). MS ($ES^+$) m/z 447 (M+H)$^+$.

Step 6: methyl 11-cyclohexyl-2-[2-(dimethylamino) ethyl]-1,4-dioxo-1,2,3,4,17,17a-hexahydro-6H-indolo[2,1-a]pyrazino[2,1-d][2,5]-benzodiazocine-14-carboxylate 1.4 eq of NaH (60% dispersion in mineral oil) was added to a solution of dimethyl 14-cyclohexyl-5,6,7,8-tetrahydroindolo[2,1-a][2,5]benzodiazocine-7,11-dicarboxylate in DMF (0.1 M) and the solution allowed to stir at RT for 30 min. Then 1.2 eq of bromoacetyl bromide were added and the mixture stirred at RT for 20 min. To the mixture, 2 eq of N,N-dimethylethane-1,2-diamine were added and the reaction heated at 50° C. for 30 min. The solution was diluted with EtOAc and washed with water. The aqueous phase was extracted with EtOAc (×3) and the combined organics washed with brine, dried over $Na_2SO_4$, filtered and the solvent evaporated in vacuo to afford the title compound. The material was then used in the next step without any further purification. MS ($ES^+$) m/z 543 (M+H)$^+$.

Step 7: 11-cyclohexyl-2-[2-(dimethylamino)ethyl]-1,2,3,4,17,17a-hexahydro-6H-indolo[2,1-a]pyrazino[2,1-d][2,5]-benzodiazocine-14-carboxylic acid To a solution of methyl 11-cyclohexyl-2-[2-(dimethylamino)ethyl]-1,4-dioxo -1,2,3,4,17,17a-hexahydro-6H-indolo[2,1-a]pyrazino[2,1-d][2,5]benzodiazocine-14-carboxylate in THF (0.15 M), 20 eq of $BH_3.Me_2S$ (2 M solution in THF) were added and the mixture was stirred overnight at RT. The solution was carefully quenched by adding 1.25 N HCl in MeOH until effervescence subsided. Then the volatiles were driven off by boiling the mixture to dryness. The crude residue was dissolved in MeOH (0.06 M) and 10 eq of 1N NaOH (aq) were added. The solution was stirred at 60° C. for 5 h. The solvent was evaporated in vacuo. The crude was then purified by prep RP-HPLC (stationary phase: column WATERS X-TERRA prep. C18, 5 microns. Mobile phase: MeCN/$H_2O$ buffered with 0.1% TFA). Fractions containing the pure compound were combined and freeze dried to afford the title compound as a white powder (8% yield from dimethyl 14-cyclohexyl-5,6,7,8-tetrahydroindolo[2,1-a][2,5]benzodiazocine-7,11-dicarboxylate). $^1$H NMR (400 MHz, DMSO-$d_6$+ TFA, 330 K) δ 8.15 (s, 1H), 7.93 (d, J 8.4, 1H), 7.90-7.85 (m, 1H), 7.76 (d, J 8.4, 1H), 7.70-7.60 (m, 2H), 7.59-7.49 (m, 1H), 4.50-4.40 (m, 1H), 4.30-4.20 (m, 1H), 4.00-3.80 (m, 2H), 3.80-3.70 (m, 1H), 3.70-3.50 (m, 2H), 3.40-3.20 (m, 5H), 2.79 (s, 6H), 2.80-2.70 (m, 2H), 2.70-2.60 (m, 2H), 2.00-1.80 (m, 3H), 1.80-1.60 (m, 2H), 1.60-1.50 (m, 1H), 1.40-1.10 (m, 4H); MS ($ES^+$) m/z 501 (M+H)$^+$.

EXAMPLE 5

14-cyclohexyl-5-methyl-7,8-dihydroimidazo[4,5,1-jk]indolo[1,2-d][1,4]benzodiazepine-11-carboxylic acid

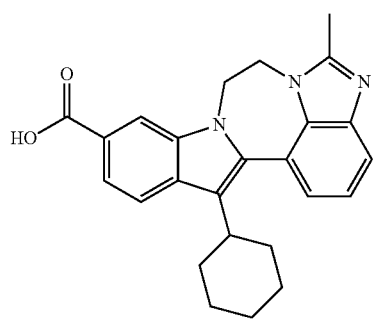

Step 1: [3-(acetylamino)-2-aminophenyl]boronic acid

10% Pd on carbon (cat.) was added as a slurry in EtOH under $N_2$ to [3-(acetylamino)-2-nitrophenyl]boronic acid in EtOH (0.05 M). The atmosphere in the reaction vessel was flushed with hydrogen (1 atm) and the reaction stirred vigorously at RT for 20 min. The hydrogen atmosphere was then replaced with $N_2$ before filtering through a plug of CELITE— washing well with EtOH. The EtOH solution was concentrated in vacuo to afford the crude title compound as a brown solid, which was used immediately in the subsequent cross-coupling step. MS ($ES^+$) m/z 195 (M+H)$^+$.

Step 2: methyl 2-[3-(acetylamino)-2-aminophenyl]-3-cyclohexyl-1H-indole-6-carboxylate

[3-(acetylamino)-2-aminophenyl]boronic acid (prepared as described in Example 5, Step 1 above) (1.1 eq) was added to a solution of 2-bromo-3-cyclohexyl-1H-indole-6-carboxylate (prepared from commercially available methyl indole-6-carboxylate as described in WO 2004/087714) in dioxane (0.06 M). 2M aqueous $Na_2CO_3$ (4 eq) was introduced and the mixture degassed by sonication under a $N_2$ atmosphere prior to introducing bis(triphenylphosphine)palladium(II) dichloride (0.2 eq) and heating at 105° C. for 2 h. The reaction was allowed to cool to RT before partitioning between EtOAc and water. The aqueous phase was extracted a second time with EtOAc and the combined organics washed with water, brine before being dried over anhydrous sodium sulfate, filtered and concentrated in vacuo. Purification by flash chromatography (5% MeOH/$CH_2Cl_2$) afforded the title compound as a glass (59%). MS ($ES^+$) m/z 406 (M+H)$^+$.

Step 3: methyl 2-{3-(acetylamino)-2-[(chloroacetyl)amino]phenyl}-3-cyclohexyl-1H-indole-6-carboxylate N-methyl morpholine (1 eq) and chloroacetylchloride (1 eq) were added to a stirred solution of methyl 2-[3-(acetylamino)-2-aminophenyl]-3-cyclohexyl-1H-indole-6-carboxylate in $CH_2Cl_2$ (0.03 M) under $N_2$. After stirring at RT for 1 h, further N-methyl morpholine (1 eq) and chloroacetylchloride (1 eq) were introduced. The reaction was stirred for another hour before diluting with $CH_2Cl_2$ and washing with 1N HCl (aq), water and brine. The organics were then dried over anhydrous sodium sulfate, filtered and concentrated in vacuo to afford the title compound as a brown solid that was taken on in the subsequent step without further purification (91%). MS ($ES^+$) m/z 482 (M+H)$^+$, 484 (M+H)$^+$.

Step 4: methyl 4-(acetylamino)-13-cyclohexyl-6-oxo-6,7-dihydro-5H-indolo[1,2-d][1,4]-benzodiazepine-10-carboxylate NaH (60% dispersion in mineral oil) (1.7 eq) was added to a stirred solution of methyl 2-{3-(acetylamino)-2-[(chloroacetyl)amino]phenyl}-3-cyclohexyl-1H-indole-6-carboxylate in anhydrous DMF (0.02 M) at RT under $N_2$. The reaction was stirred vigorously for 1 h before quenching with 1N HCl (aq) and extracting into EtOAc. The aqueous phase was extracted a second time with EtOAc and the combined organics washed well with 1N HCl (aq), water and brine before being dried over anhydrous sodium sulfate, filtered and concentrated in vacuo to afford the title compound as a brown glass (94%). The material was taken on in the subsequent step without further purification. MS ($ES^+$) m/z 446 (M+H)$^+$.

Step 5: methyl 14-cyclohexyl-5-methyl-7,8-dihydroimidazo[4,5,1-jk]indolo[1,2-d][1,4]-benzodiazepine-11-carboxylate BH$_3$.Me$_2$S complex (2M in THF) (20 eq) was added to a stirred solution of methyl 4-(acetylamino)-13-cyclohexyl-6-oxo-6,7-dihydro-5H-indolo[1,2-d][1,4]benzodiazepine-10-carboxylate in anhydrous THF (0.02 M) at RT under N$_2$. After 45 min further BH$_3$.Me$_2$S complex (2M in THF) (5 eq) were introduced and the reaction left to stir for 1 h. The reaction was quenched by cautious addition of 1N HCl (aq) and MeOH before partitioning between saturated NaHCO$_3$ (aq) and EtOAc. The organics were washed with water, brine before being dried over anhydrous sodium sulfate, filtered and concentrated in vacuo to afford the crude product. Purification by flash chromatography (3% MeOH/CH$_2$Cl$_2$) afforded the title compound (36%). MS (ES$^+$) m/z 414 (M+H)$^+$.

Step 6: 14-cyclohexyl-5-methyl-7,8-dihydroimidazo[4,5,1-jk]indolo[1,2-d][1,4]-benzodiazepine-11-carboxylic acid Methyl 14-cyclohexyl-5-methyl-7,8-dihydroimidazo[4,5,1-jk]indolo[1,2-d][1,4]benzodiazepine-11-carboxylate was dissolved in a mixture of H$_2$O/MeOH/THF (1/1/1) (0.015 M) and LiOH.H$_2$O added (4.4 eq). The reaction was stirred with heating at 60° C. for 3 h, before being allowed to cool to RT, acidified with 1N HCl (aq). The volatiles were removed in vacuo and the residue purified by RP-HPLC (stationary phase: column WATERS X-TERRA prep. C18, 5 microns. Mobile phase: MeCN/H$_2$O buffered with 0.1% TFA). Fractions containing the pure compound were combined and freeze dried to afford the title compound as a white powder (68%). $^1$H NMR (400 MHz, DMSO-d$_6$, 300 K) δ 8.30 (s, 1H), 7.99 (d, 1H, J 8.6), 7.79 (d, 1H, J 7.6), 7.68 (d, 1H, J 8.6), 7.67-7.56 (m, 2H), 5.39-5.29 (m, 1H), 4.80-4.72 (m, 1H), 4.38-4.29 (m, 1H), 4.23-4.14 (m, 1H), 3.14-3.06 (m, 1H), 2.73 (s, 3H), 2.19-2.06 (m, 3H), 1.98-1.90 (m, 1H), 1.78-1.72 (m, 2H), 1.55-1.42 (m, 3H), 1.24-1.14 (m, 1H); MS (ES$^+$) m/z 400 (M+H)$^+$.

EXAMPLE 6

13-cyclohexyl-6,7-dihydro-4H-indolo[4',3':3,4,5]azepino[1,2-a]indole-10-carboxylic acid

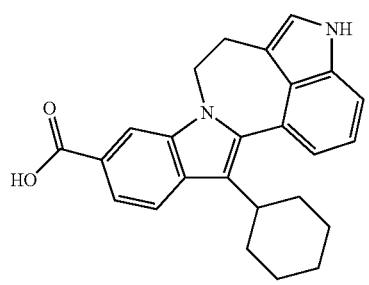

Step 1: methyl 3-cyclohexyl-1-[2-(dimethylamino)-2-oxoethyl]-1H,1'H-2,4'-biindole-6-carboxylate To a solution of methyl 2-bromo-3-cyclohexyl-1-[2-(dimethylamino)-2-oxoethyl]-1H-indole-6-carboxylate (prepared from commercially available methyl indole-6-carboxylate as described in WO 2004/087714) in dioxane (0.15 M) were added 6 eq of Na$_2$CO$_3$ (2 M aqueous solution), 1.5 eq of 1H-indol-4-ylboronic acid and 0.2 eq of bis(triphenylphosphine)palladium(II) dichloride. The mixture was heated at reflux for 1.5 h. The reaction mixture was filtered and then the filtrate was diluted with EtOAc. The organic phase was washed with aqueous Na$_2$CO$_3$, brine and dried over Na$_2$SO$_4$ before being filtered and concentrated in vacuo. The crude was purified by flash chromatography (Biotage cartridge, 6.0:4.0 EtOAc/PE) to afford the title compound (95%). MS (ES$^+$) m/z 458 (M+H)$^+$.

Step 2: methyl 13-cyclohexyl-6-oxo-6,7-dihydro-4H-indolo[4',3':3,4,5]azepino[1,2-a]indole-10-carboxylate To a solution of methyl 3-cyclohexyl-1-[2-(dimethylamino)-2-oxoethyl]-1H,1'H-2,4'-biindole-6-carboxylate in dioxane (0.10 M), 3 eq of POCl$_3$ were added and the mixture was stirred for 2 h at 140° C. The solution was allowed to cool before adding an excess of 1 N HCl (aq) and heating at reflux for 30 min. Then the volatiles were removed in vacuo to afford the title compound, which could be used directly in the next step. MS (ES$^+$) m/z 413 (M+H)$^+$.

Step 3: 13-cyclohexyl-6,7-dihydro-4H-indolo[4',3':3,4,5]azepino[1,2-a]indole-10-carboxylic acid To a solution of methyl 13-cyclohexyl-6-oxo-6,7-dihydro-4H-indolo[4',3':3,4,5]azepino[1,2-a]indole-10-carboxylate in THF (0.15 M), 20 eq of BH$_3$.Me$_2$S (2 M solution in THF) were added and the mixture was stirred overnight at RT. The solution was carefully quenched by adding 1.25 N HCl in MeOH until effervescence subsided. Then the volatiles were driven off by boiling the mixture to dryness. The residue was dissolved in MeOH (0.06 M) and 10 eq of 1N NaOH (aq) were added. The solution stirred at 60° C. for 2 h before removing volatiles in vacuo. The crude was then purified by prep RP-HPLC (stationary phase: column WATERS X-TERRA prep. C18, 5 microns. Mobile phase: MeCN/H$_2$O buffered with 0.1% TFA). Fractions containing the pure compound were combined and freeze dried to afford the title compound (12% yield from methyl 3-cyclohexyl-1-[2-(dimethylamino)-2-oxoethyl]-1H,1'H-2,4'-biindole-6-carboxylate).
$^1$H NMR (400 MHz, DMSO-d$_6$+TFA, 300 K) δ 8.20 (s, 1H), 7.85 (d, J 8.4, 1H), 7.65 (d, J 8.4, 1H), 7.45 (d, J 7.9, 1H), 7.30-7.10 (m, 3H), 5.20-5.00 (m, 1H), 4.10-3.90 (m, 1H), 3.30-3.10 (m, 2H), 2.80-2.70 (m, 1H), 2.10-1.80 (m, 3H), 1.70-1.50 (m, 2H), 1.50-1.30 (m, 3H), 1.30-1.00 (m, 2H); MS (ES$^+$) m/z 385 (M+H)$^+$.

EXAMPLE 7

10-cyclohexyl-5H,16H-imidazo[2,1-d]indolo[2,1-a][2,5]benzodiazocine-13-carboxylic acid

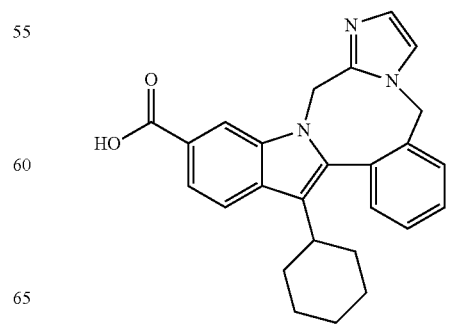

Step 1: Methyl 3-cyclohexyl-2-[2-(hydroxymethyl) phenyl]-1H-indole-6-carboxylate A solution (0.04 M) of methyl 2-bromo-3-cyclohexyl-1H-indole-6-carboxylate (prepared as described in WO2004/087714) in DME/EtOH 5:2 was treated with [2-(hydroxymethyl)phenyl]boronic acid (1.2 eq), $Na_2CO_3$ (6 eq) and $Pd(PPh_3)_4$ (0.1 eq) at 80° C. After 1 h the mixture was diluted with EtOAc, washed with saturated aqueous $NaHCO_3$ and brine, then dried and concentrated under reduced pressure. The residue was purified by flash chromatography on $SiO_2$ (7:3 PE/EtOAc) to give the title compound (93%) as a solid. MS (ES+) m/z 364 (M+H$^+$).

Step 2: Methyl 2-[2-({[tert-butyl(dimethyl)silyl]oxy}methyl)phenyl]-3-cyclohexyl-1H-indole-6-carboxylate A solution (0.039 M) of methyl 3-cyclohexyl-2-[2-(hydroxymethyl)phenyl]-1H-indole-6-carboxylate was treated with 2,6-lutidine (2 eq) and then with tert-butyl(dimethyl)silyl trifluoromethanesulfonate (1.2 eq). The solution was stirred for 15 min. Removal of the volatiles in vacuo gave a residue that was diluted with EtOAc, washed with 1N HCl, saturated aqueous $NaHCO_3$, brine, dried and concentrated in vacuo to afford the title compound (90%) as a solid. MS (ES+) m/z 478 (M+H$^+$).

Step 3: Methyl 1-[(L-benzyl-1H-imidazol-2-yl)methyl]-3-cyclohexyl-2-[2-(hydroxymethyl)phenyl]-1H-indole-6-carboxylate A solution (0.09 M) of the foregoing material was cooled to 0° C. and treated with NaH (60% suspension in mineral oil, 2.7 eq). The mixture was stirred for 30 min then warmed to 20° C. 1-benzyl-2-(chloromethyl)-1H-imidazol-3-ium chloride (1.1 eq) was added and the mixture was stirred for 3 h then taken up in EtOAc, washed with brine, dried and concentrated in vacuo. The residue was purified by flash chromatography on $SiO_2$ (25% to 30% EtOAc: PE as eluent) to give the title compound (18%). MS (ES+) m/z 534 (M+H$^+$).

Step 4: Methyl 3-cyclohexyl-2-[2-(hydroxymethyl) phenyl]-1-(1H-imidazol-2-ylmethyl)-1H-indole-6-carboxylate A solution (0.05 M) of the foregoing material in MeOH was treated with 20 wt/% of Pd/C (10%) and stirred under an atmosphere of hydrogen. The mixture was filtered through CELITE and the filtrate was concentrated to give the title compound (80%). MS (ES+) m/z 444 (M+H$^+$).

Step 5: Methyl 10-cyclohexyl-5H,16H-imidazo[2,1-d]indolo[2,1-a][2,5]benzodiazocine-13-carboxylate The foregoing material was dissolved in THF (0.018 M) then $Ph_3P$ (2.5 eq.) and DEAD (2.5 eq.) were added. The mixture was stirred for 30 min, then the solvent was evaporated under vacuum and the residue was directly purified by RP HPLC(C18, 5 μM, $H_2O$/MeCN with 1% of TFA as eluent) to afford the desired product as the TFA salt. MS (ES+) m/z 426 (M+H$^+$).

Step 6: 10-cyclohexyl-5H,16H-imidazo[2,1-d]indolo[2,1-a][2,5]-benzodiazocine-13-carboxylic acid The foregoing material was dissolved in a solution (0.043 M) of dioxane/water 2:1, treated with 5N KOH (3 eq) and heated to 60° C. for 1 h. This solution was directly purified by RP HPLC (C18, 5 μM, $H_2O$/MeCN with 1% of TFA as eluent) to afford the desired product as TFA salt. $^1$H NMR (300 MHz, DMSO-$d_6$, 300 K) δ12.8 (br s, 1H), 8.13 (s, 1H), 7.93 (d, J 8.4, 1H), 7.80-7.64 (m, 5H), 7.62-7.52 (m, 2H), 5.78 (d, J 17.6, 1H), 5.49 (d, J 14.2, 1H), 4.78 (d, J 17.6, 1H), 4.54 (d, J 14.2, 1H), 2.76-2.64 (m, 1H), 1.98-1.60 (m, 7H), 1.10-1.40 (m, 3H), 1.60-1.98 (m, 7H). MS (ES+) m/z 412 (M+H$^+$).

EXAMPLE 8

14-cyclohexylspiro[indolo[1,2-e][1,5]benzoxazocine-7,3'-oxetane]-11-carboxylic acid

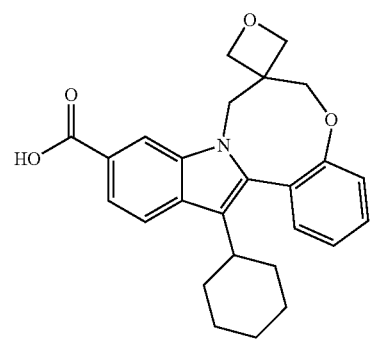

A catalytic amount of TsOH monohydrate was added to a suspension of methyl 14'-cyclohexyl-2,2-dimethylspiro[1,3-dioxane-5,7'-indolo[1,2-e][1,5]benzoxazocine]-11'-carboxylate (as prepared in Example 2, Step 3) in MeOH/THF 1:2 (0.03 M) and the solution was stirred at RT for 3 h. Filtration on a pad of neutral alumina with EtOAc afforded after removal of the solvent in vacuo, methyl 14-cyclohexyl-7,7-bis(hydroxymethyl)-7,8-dihydro-6H-indolo[1,2-e][1,5]benzoxazocine-11-carboxylate (quant). Triflic anhydride (2.8 eq) was added at 0° C. to a solution of this material in dry MeCN (0.05M), DIPEA (3.0 eq) was added and the mixture was stirred at 0° C. for 15 min, then further 3.0 eq of DIPEA were added; iPrNH$_2$ (2 eq) was added, the mixture was transferred to a closed vessel and stirring was continued at 70° C. for 4 h. EtOAc was added, the organic phase was washed with water and brine, dried over $Na_2SO_4$ and the solvent was removed in vacuo. The residue was hydrolysed with aq. 1N KOH in dioxane (65° C., overnight); evaporation to dryness gave a residue that was purified by RP-HPLC affording the title compound (15%) and 14'-cyclohexyl-1-isopropylspiro[azetidine-3,7'-indolo[1,2-e][1,5]benzoxazocine]-111'-carboxylic acid (4%). $^1$H NMR (400 MHz, DMSO-$d_6$, 330 K) δ 1.14-1.38 (m, 3H), 1.56-2.04 (m, 7H), 2.64-2.76 (m, 1H), 3.87 (d, J 15.6, 1H), 4.11 (d, J 6.1, 1H), 4.17 (d, J 12.5, 1H), 4.36 (d, J 6.1, 1H), 4.44 (d, J 12.5, 1H), 4.55 (d, J 6.3, 1H), 4.59 (d, J 6.1, 1H), 5.14 (d, J 15.4, 1H), 7.20-7.24 (m, 3H), 7.47 (bt, J 6.6, 1H), 7.66 (d, J 8.3, 1H), 7.85 (d, J 8.3, 1H), 8.38 (s, 1H); MS (ES$^+$) m/z 418 (M+H)$^+$.

EXAMPLE 9

14'-cyclohexyl-1-[2-(diethylamino)ethyl]spiro[azetidine-3,7'-indolo[1,2-e][1,5]benzoxazocine]-11'-carboxylic acid

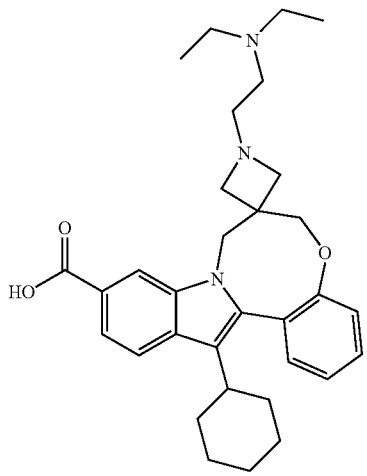

TsOH monohydrate (1 eq.) was added to a suspension of methyl 14'-cyclohexyl-2,2-dimethylspiro[1,3-dioxane-5,7'-indolo[1,2-e][1,5]benzoxazocine]-11'-carboxylate (Example 2, Step 3) in MeOH/THF 1:3 (0.03 M), and the solution was stirred at RT for 6 h. Filtration on a pad of neutral alumina using EtOAc as eluent afforded after evaporation of the solvent in vacuo, methyl 14-cyclohexyl-7,7-bis(hydroxymethyl)-7,8-dihydro-6H-indolo[1,2-e][1,5]benzoxazocine-11-carboxylate (91%). Triflic anhydride (3.5 eq) was added at 0° C. to a solution of this material in dry MeCN (0.05M), DIPEA (4.0 eq) was added and the mixture was stirred at 0° C. for 15 min, then further 4.0 eq of DIPEA were added; N,N-diethylethane-1,2-diamine (2 eq) was added, and the mixture was stirred at 70° C. for 2 h. After removal of the solvent EtOAc was added, the organic phase was washed with water and brine, dried over $Na_2SO_4$ and the solvent was removed in vacuo. The residue was hydrolysed with aq. 1N KOH in dioxane (75° C., 2 h) under degassed conditions; after quenching at 0° C. with 1N HCl evaporation to dryness gave a residue that was purified by RP-HPLC to afford the title compound (TFA salt, 25%). $^1$H NMR (600 MHz, DMSO-$d_6$, 300 K) δ 1.15-1.37 (m, 3H), 1.22 (t, 7.1, 6H), 1.57 (bd, J 11.6, 1H), 1.67-1.74 (m, 2H), 1.84 (bd, J 11.6, 1H), 1.90-2.02 (m, 3H), 2.64-2.68 (m, 1H), 3.18 (q, J 7.1, 4H), 3.24-3.30 (m, 2H), 3.74 (bs, 2H), 3.86 (d, J 10.4, 1H), 3.95 (bd, J 15, 1H), 4.09 (d, J 10.8, 1H), 4.14 (d, J 10.4, 1H), 4.24 (bd, J 12.5, 1H), 4.28 (bd, J 12.5, 1H), 4.37 (d, J 10.8, 1H), 5.21 (bd, J 15, 1H), 7.20-7.22 (m, 3H), 7.48-7.51 (m, 1H), 7.69 (d, J 8.4, 1H), 7.90 (d, J 8.4, 1H), 8.55 (s, 1H); MS (ES$^+$) m/z 516 (M+H)$^+$.

EXAMPLE 10

14'-cyclohexyl-1-(N,N-dimethyl-β-alanyl)spiro[azetidine-3,7'-indolo[1,2-e][1,5]benzoxazocine]-11'-carboxylic acid

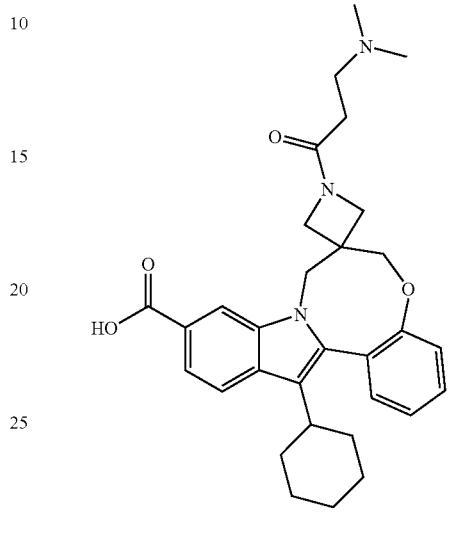

Step 1: methyl 1-benzyl-14'-cyclohexylspiro[azetidine-3,7'-indolo[1,2-e][1,5]benzoxazocine]-11'-carboxylate This compound was prepared from 14'-cyclohexyl-2,2-dimethylspiro[1,3-dioxane-5,7'-indolo[1,2-e][1,5]benzoxazocine]-11'-carboxylate (Example 2, Step 3) and benzylamine as described in Example 9. Flash chromatography (PE:EtOAc 2:1) gave a mixture of the title compound and methyl 14-cyclohexylspiro[indolo[1,2-e][1,5]benzoxazocine-7,3'-oxetane]-11-carboxylate in 65% yield. MS (ES$^+$) m/z 521 (M+H)$^+$.

Step 2: methyl 14'-cyclohexylspiro[azetidine-3,7'-indolo[1,2-e][1,5]-benzoxazocine]-11'-carboxylate A 0.07M solution of methyl 1-benzyl-14'-cyclohexylspiro[azetidine-3,7'-indolo[1,2-e][1,5]benzoxazocine]-11'-carboxylate in MeOH and EtOAc (2:1) was stirred in the presence of 10% Pd/C and 3M HCl under H$_2$-atmosphere for 3 days. The reaction mixture was filtered on CELITE and co-evaporated with toluene, pentane and Et$_2$O until a solid was obtained; this solid was washed with Et$_2$O and dried to afford the title compound as its HCl salt (46%). MS (ES$^+$) m/z 431 (M+H)$^+$.

Step 3: 14'-cyclohexyl-1-(N,N-dimethyl-β-alanyl)spiro[azetidine-3,7'-indolo[1,2-e][1,5]benzoxazocine]-11'-carboxylic acid Methyl 1,4'-cyclohexylspiro[azetidine-3,7'-indolo[1,2-e][1,5]benzoxazocine]-11'-carboxylate (HCl salt) was dissolved in dry DCM (0.1M), DIPEA (4 eq.), N,N-dimethyl-β-alanine (2 eq.) and HATU (3 eq.) were added, and the mixture was stirred at RT for 4 h; after evaporation of the solvent the residue was taken in EtOAc and washed with sat NaHCO$_3$, water and brine, dried over Na$_2$SO$_4$ and concentrated to give the methyl ester of the title compound that was hydrolysed with aq. 1N KOH/dioxane 2:1 (50° C. for 2 h, then overnight at RT); evaporation to dryness gave a residue that was purified by RP-HPLC to afford the title compound (TFA salt, 20%). $^1$H NMR (400 MHz, DMSO-d$_6$, 330 K) δ 1.17-1.38 (m, 3H), 1.57-2.01 (m, 7H), 2.62-3.38 (m, 5H), 2.77 (s, 3H), 2.81 (s, 3H), 3.67-4.42 (m, 7H), 4.98-5.04 (m, 1H), 7.20-7.26 (m, 3H), 7.48-7.54 (m, 1H), 7.68 (bd, J 7.8, 1H), 7.88 (d, J 8.4, 1H), 8.28-8.34 (m, 1H); MS (ES$^+$) m/z 516 (M+H)$^+$

EXAMPLE 11

(7R)-14-cyclohexyl-1'-methylspiro[indolo[1,2-e][1,5]benzoxazocine-7,2'-pyrrolidine]-11-carboxylic acid

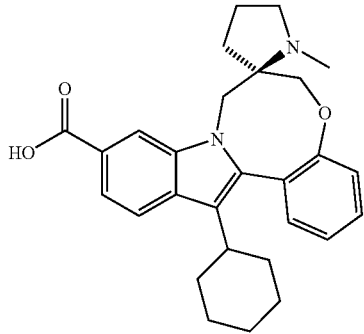

Step 1: (3R,7aR)-7a-[(benzyloxy)methyl]-3-(trichloromethyl)tetrahydro-1H-pyrrolo[1,2-c][1,3]oxazol-1-one Chloral hydrate (1.5 eq) was added to a solution of L-proline in CHCl$_3$ (1 M), the suspension was refluxed (inverse Dean-Stark trap) for 6 h; the mixture was washed with water and the aq. phase re-extracted with CHCl$_3$, the combined organic layers were dried and concentrated. Recrystallization (EtOH) of the residue afforded (3R,7aS)-3-(trichloromethyl)tetrahydro-1H-pyrrolo[1,2-c][1,3]oxazol-1-one in 72% yield. This material was dissolved in dry THF (0.12M), 2M LDA (1.5 eq) was added at −78° C. and the mixture was stirred for 40 min; 60% benzyl chloromethyl ether (3 eq) was added and stirring was continued from −78 to 0° C. for 3 h; after quenching with water the mixture was extracted with CHCl$_3$ (3×), dried over Na$_2$SO$_4$ and concentrated. Flash chromatography (PE:EtOAc 5:1) afforded the title compound which was used without further characterisation in the next reaction (48%).

Step 2: (7aR)-7a-[(benzyloxy)methyl]tetrahydro-1H-pyrrolo[1,2-c][1,3]oxazol-3-one SOCl$_2$ (2.5 eq) was added at 0° C. to a 0.2M solution of (3R,7aR)-7a-[(benzyloxy)methyl]-3-(trichloromethyl)tetrahydro-1H-pyrrolo[1,2-c][1,3]oxazol-1-one in dry MeOH, and the mixture was stirred at RT for 20 min, then at reflux for 4 h. After removal of volatiles the residue was taken in EtOAc and washed with sat NaHCO$_3$, water and brine, dried and concentrated. A 0.2M solution in dry Et$_2$O of crude methyl 2-[(benzyloxy)methyl]-L-prolinate was added at 0° C. to a stirred mixture of LiBH$_4$ (1.6 eq.) and MeOH (1.6 eq.) in dry Et$_2$O (0.3M); the mixture was stirred for 2 h at RT, then quenched with water, diluted with EtOAc, washed with water and brine, dried and concentrated to afford {(2S)-2-[(benzyloxy)methyl]pyrrolidin-2-yl}methanol that was used as such. The material was dissolved in dry DCM (0.2M) and treated with carbonyl diimidazol (2.5 eq.) at RT overnight; after dilution with DCM the mixture was washed with 1N HCl, sat NaHCO$_3$ and brine, dried over Na$_2$SO$_4$ and concentrated. Flash chromatography (PE:EtOAc 2:1) afforded the title compound in 43% overall yield.

Step 3: [(7aS)-3-oxodihydro-1H-pyrrolo[1,2-c][1,3]oxazol-7a(5H)-yl]methyl 4-nitrobenzenesulfonate 10% Pd/C (0.12 eq.) was added to a 0.1M solution of (7aR)-7a-[(benzyloxy)methyl]tetrahydro-1H-pyrrolo[1,2-c][1,3]oxazol-3-one in MeOH, and the mixture was stirred under H$_2$-atmosphere overnight at RT; filtration on CELITE gave after removing the solvent a residue that was dissolved in dry DCM (0.1M) and treated at RT for 2 h with 4-nitrobenzenesulfonyl chloride (1.3 eq.) in the presence of TEA (2 eq.) and catalytic DMAP; the mixture was diluted with DCM and washed with 1N HCl, sat NaHCO$_3$ and brine, dried and concentrated to yield 84% of crude 4-nosylate that was used without further characterization.

Step 4: methyl 2-[2-(benzyloxy)phenyl]-3-cyclohexyl-1-{[(7aR)-3-oxodihydro-1H-pyrrolo[1,2-c][1,3]oxazol-7a(5H)-yl]methyl}-1H-indole-6-carboxylate A 0.1M solution of methyl 3-cyclohexyl-2-(2-hydroxyphenyl)-1H-indole-6-carboxylate (prepared as in WO2006/046030; Example 9, Step 1) in dry DMF was treated with solid K$_2$CO$_3$ (1.5 eq.) followed by neat benzyl bromide (1.0 eq.) via syringe. The resulting suspension was stirred overnight. 1N HCl was added and the mixture extracted into EtOAc. The organic layers were washed with water and brine, then dried over Na$_2$SO$_4$ and evaporated. The residue was triturated with small portions of pentane affording after drying methyl 2-[2-(benzyloxy)phenyl]-3-cyclohexyl-1H-indole-6-carboxylate as an off-white solid (93%). 60% NaH (2 eq.) was added to a 0.2M solution of this material (1.6 eq.) in dry DMF, after stirring for 20 min a 0.2M solution of [(7aS)-3-oxodihydro-1H-pyrrolo[1,2-c][1,3]oxazol-7a(5H)-yl]methyl 4-nitrobenzenesulfonate (1 eq.) in dry DMF was added and stirring was continued at 65° C. for 4 h. After quenching with sat NH$_4$Cl the mixture was extracted with EtOAc, washed with water and brine, dried over Na$_2$SO$_4$ and concentrated; flash chromatography (PE:EtOAc 2:1) afforded the title compound (48%).

Step 5: methyl 2-[2-(benzyloxy)phenyl]-1-{[(2R)-1-(tert-butoxycarbonyl)-2-(hydroxymethyl)pyrrolidin-2-yl]methyl}-3-cyclohexyl-1H-indole-6-carboxylate 1M aq. KOH (15 eq.) was added to a 0.08M solution of methyl 2-[2-(benzyloxy)phenyl]-3-cyclohexyl-1-{[(7aR)-3- oxodihydro-1H-pyrrolo[1,2-c][1,3]oxazol-7a(5H)-yl]methyl}-1H-indole-6-carboxylate in MeOH, and the mixture was refluxed for 2 days. After quenching with an equivalent amount of aq. HCl and evaporation of volatiles, the residue was taken in toluene:MeOH 4:1 (0.1M) and treated at RT with excess (2.5 eq.) TMS-diazomethane for 1 h; evaporation of solvents gave crude methyl 2-[2-(benzyloxy)phenyl]-3-cyclohexyl-1-{[(2R)-2-(hydroxymethyl)pyrrolidin-2-yl]methyl}-1H-indole-6-carboxylate. To a 0.1M solution of this material in dry DCM were added TEA (3 eq.) and Boc$_2$O (1.5 eq.) and the mixture was stirred at RT overnight, after quenching with sat NaHCO$_3$ the mixture was extracted with EtOAc, washed with brine, dried and concentrated; chromatography (PE/EtOAc 2:1) afforded the title compound (57%).

Step 6: 1'-tert-butyl 11-methyl (7R)-14-cyclohexyl-1'H-spiro[indolo[1,2-e][1,5]benzoxazocine-7,2'-pyrrolidine]-1',11-dicarboxylate 10% Pd/C (0.2 eq.) was added to a 0.03M solution of methyl 2-[2-(benzyloxy)phenyl]-1-{[(2R)-1-(tert-butoxycarbonyl)-2-(hydroxymethyl)pyrrolidin-2-yl]methyl}-3-cyclohexyl-1H-indole-6-carboxylate in MeOH, and the mixture was stirred under H$_2$-atmosphere at RT for 2.5 h; filtration on CELITE gave after removing the solvent a residue (methyl 1-{[(2R)-1-(tert-butoxycarbonyl)-2-(hydroxymethyl)pyrrolidin-2-yl]methyl}-3-cyclohexyl-2-(2-hydroxyphenyl)-1H-indole-6-carboxylate) that was dissolved in dry DCM (0.1M) and added at RT to a mixture of Ph$_3$P (2.2 eq.) and DIAD (2.2 eq.) in dry DCM (0.5M); after refluxing for 90 min all volatiles were evaporated in vacuo and the residue purified by chromatography (PE:EtOAc, 2:1) to afford the title compound (17%).

Step 7: (7R)-14-cyclohexyl-1'-methylspiro[indolo[1,2-e][1,5]benzoxazocine-7,2'-pyrrolidine]-11-carboxylic acid A 0.03M solution of 1'-tert-butyl 11-methyl (7R)-14-cyclohexyl-1'H-spiro[indolo[1,2-e][1,5]benzoxazocine-7,2'-pyrrolidine]-1',11-dicarboxylate in DCM:TFA 3:1 was stirred at RT for 2 h; the residue obtained after evaporation was dissolved in MeOH (0.05M), TEA (3 eq), AcOH (5 eq.) and NaCNBH$_3$ (1.5 eq.) were added; after addition of 37% aq. formaldehyde (2.7 eq.) the mixture was stirred at RT for 4 h. After evaporation of MeOH, the residue was taken in EtOAc and washed with sat NaHCO$_3$ and brine, dried over Na$_2$SO$_4$ and concentrated to give the methyl ester of the title compound (96%) that was hydrolysed with aq. 1N KOH:MeOH 2:1 (60° C., 2 h); evaporation to dryness gave a residue that was purified by RP-HPLC to afford the title compound (TFA salt, 36%). $^1$H NMR (400 MHz, DMSO-d$_6$, 330 K) δ 1.12-1.44 (m, 3H), 1.60-1.77 (m, 4H), 1.83-2.10 (m, 7H), 2.66-2.78 (m, 1H), 2.94 (s, 3H), 3.52 (bs, 1H), 3.76 (bs, 1H), 4.22-4.32 (m, 1H), 4.97 (bs, 1H), 7.23-7.24 (m, 3H), 7.49-7.52 (m, 1H), 7.69 (d, J 8.4, 1H), 7.89 (d, J 8.4, 1H), 8.35 (s, 1H); MS (ES$^+$) m/z 445 (M+H)$^+$.

EXAMPLE 12 rel-(3aS,14bS)-10-cyclohexyl-13-methoxy-1-methyl-1,2,3,3a,4,14b-hexahydroindolo[2,1-a]pyrrolo[3,2-d][2]benzazepine-7-carboxylic acid

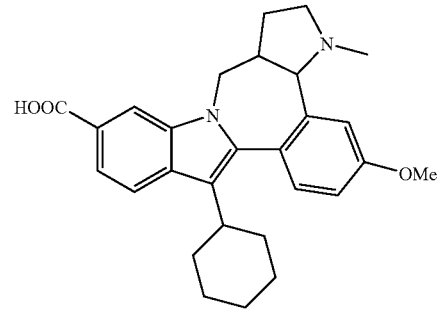

Step 1: (2-bromo-5-methoxyphenyl)methanol

2-Bromo-5-methoxy benzoic acid (1 eq.) was dissolved in anhydrous THF (0.55M solution) and borane dimethylsulfide complex (2M in THF, 1 eq.) was added dropwise to the solution. The mixture was left stirring overnight, then HCl in MeOH was added and the mixture was warmed to 60° C. All volatiles were evaporated and the residual material was dissolved in DCM. The solution was washed with 1N HCl and with brine, then dried over Na$_2$SO$_4$ and evaporated in vacuo. A colorless oil was obtained (94%), which was used without further characterization in the next reaction.

Step 2: [(2-bromo-5-methoxybenzyl)oxy](triisopropyl)silane (2-Bromo-5-methoxyphenyl)methanol (1 eq.) was dissolved in anhydrous DMF (1.1M solution) and imidazole (1.05 eq.) was added. To the stirred solution triisopropylsilyl chloride (1.1 eq.) was added and the resulting mixture was left stirring at RT for 8 h. All volatiles were evaporated in vacuo and the residual material was filtered with PE/EtOAc (9:1) over a pad of silica gel. After evaporation in vacuo the product was obtained as a colorless oil (94%), which was used without further characterization in the next reaction.

Step 3: (4-methoxy-2-{[(triisopropylsilyl)oxy]methyl}phenyl)boronic acid

[(2-bromo-5-methoxybenzyl)oxy](triisopropyl)silane (1 eq.) was dissolved in anhydrous THF (0.43M solution) and the solution was cooled to −78° C. A solution of n-BuLi (1.6M in hexanes, 1.05 eq.) was added and the resulting mixture was left stirring for 1 h at −78° C. Then triisopropyl borate (50% in THF, 1.3 eq.) was added dropwise and the mixture was allowed to warm to RT overnight. 1N HCl was added and the resulting mixture was left stirring at RT for 30 min. THF was removed in vacuo and replaced with Et$_2$O. The organic phase was washed with water and with brine, then dried over Na$_2$SO$_4$ and evaporated in vacuo. The product was obtained as a colorless oil (64% yield, 65% pure) which was used without further purification in the next reaction.

Step 4: methyl 3-cyclohexyl-2-(4-methoxy-2-{[(triisopropylsilyl)oxy]methyl}phenyl)-1H-indole-6-carboxylate 2-Bromo-3-cyclohexyl indole-6-carboxylic acid methyl ester (1 eq., prepared as described in WO2004/087714 from commercially available methyl indole-6-carboxylate) and (4-methoxy-2-{[(triisopropylsilyl)oxy]methyl}phenyl)boronic acid (1.1 eq.) were dissolved in dioxane (0.125M solution) and 2M aq. sodium carbonate solution (3.3 eq.) was added. The mixture was degassed and flushed with argon. Then bis(triphenylphosphine)palladium dichloride (0.1 eq.) was added and the mixture was heated under argon atmosphere to 110° C. After 5 h at this temperature all volatiles were evaporated in vacuo and the residual material was dissolved in EtOAc. The solution was extracted with water and with brine, then dried over $Na_2SO_4$ and evaporated in vacuo. The residual material was purified by flash chromatography (PE:EtOAc, 9:1). After evaporation of the solvents the product was obtained as an off-white foam (81%). The material was used without further characterization in the next reaction.

Step 5: methyl 1-allyl-3-cyclohexyl-2-(4-methoxy-2-{[(triisopropylsilyl)oxy]methyl}phenyl)-1H-indole-6-carboxylate Methyl 3-cyclohexyl-2-(4-methoxy-2-{[(triisopropylsilyl)oxy]methyl}phenyl)-1H-indole-6-carboxylate (1 eq.) was dissolved in DMF (0.34M solution) and the solution was degassed. NaH (1.1 eq.) was added and the mixture was left stirring for 5 min. Allyl bromide (1.2 eq.) was added and stirring was continued for 5 h. All volatiles were evaporated in vacuo and the residual material was dissolved in $Et_2O$. The solution was washed with 0.5N HCl, saturated aq. $NaHCO_3$ solution and with brine. After drying the organic phase over $Na_2SO_4$ all volatiles were evaporated in vacuo and the residual material was purified by flash chromatography (PE:EtOAc, 10:1). After evaporation of the solvents the product was obtained as a colorless sticky solid (84%). The material was used without further characterization in the next reaction.

Step 6: methyl 1-allyl-3-cyclohexyl-2-[2-(hydroxymethyl)-4-methoxyphenyl]-1H-indole-6-carboxylate Methyl 1-allyl-3-cyclohexyl-2-(4-methoxy-2-{[(triisopropylsilyl)oxy]methyl}phenyl)-1H-indole-6-carboxylate (1 eq.) was dissolved in THF (0.28M solution) and a 1M solution of tetrabutylammonium fluoride in THF (1 eq.) was added. The mixture was left stirring at RT for 2 h, then all volatiles were evaporated in vacuo and the residual material was dissolved in $Et_2O$. The solution was washed with 1N HCl, saturated aq. $NaHCO_3$ solution and with brine. The organic phase was dried over $Na_2SO_4$ and evaporated in vacuo. The residual material was purified by flash chromatography (PE:EtOAc, 8:2). After evaporation of the solvents the product was obtained as colorless foam (88%). MS ($ES^+$): 434.2 ($M+H^+$).

Step 7: methyl 1-allyl-3-cyclohexyl-2-(2-formyl-4-methoxyphenyl)-1H-indole-6-carboxylate DMSO (5 eq.) was dissolved in DCM and the solution was cooled to −78° C. To the stirred solution oxalylchloride (2.5 eq.) was added and the mixture was left stirring for 30 min. A solution of methyl 1-allyl-3-cyclohexyl-2-[2-(hydroxymethyl)-4-methoxyphenyl]-1H-indole-6-carboxylate (1 eq.) in DCM (0.25M solution) was added and the mixture was left stirring for 30 min at −78° C. $Et_3N$ (8 eq.) was added and the mixture was allowed to warm to 0° C. At this temperature stirring was continued for 2 h, and then stirring was continued at RT overnight. The mixture was diluted with DCM, and then washed with water, 1N HCl, saturated aq. $NaHCO_3$ solution and with brine. After drying over $Na_2SO_4$ all volatiles were evaporated in vacuo. The residual material was purified by flash chromatography (PE:EtOAc, 9:1). After evaporation of the solvents the product was obtained as a yellow foam (88%). MS ($ES^+$): 432.1 ($M+H^+$).

Step 8: methyl rel-(3aS,14bS)-10-cyclohexyl-13-methoxy-1-methyl-1,2,3,3a,4,14b-hexahydroindolo[2,1-a]pyrrolo[3,2-d][2]benzazepine-7-carboxylate Methyl 1-allyl-3-cyclohexyl-2-(2-formyl-4-methoxyphenyl)-1H-indole-6-carboxylate (1 eq.) was dissolved in toluene (0.05M solution) and sarcosine (1.1 eq.) was added. After heating to 110° C. for 90 min 20 vol-% DMF were added and heating was continued for 2 h. After cooling to RT the mixture was diluted with EtOAc and the resulting solution was extracted with 1N HCl, saturated aq. $NaHCO_3$ solution and with brine. After drying over $Na_2SO_4$ all volatiles were evaporated in vacuo. The residual material was purified by flash chromatography (PE:EtOAc, 8:2). The product was obtained as colorless foam (61%) which was used without further characterization in the next reaction.

Step 9: rel-(3aS,14bS)-10-cyclohexyl-13-methoxy-1-methyl-1,2,3,3a,4,14b-hexahydroindolo[2,1-a]pyrrolo[3,2-d][2]-benzazepine-7-carboxylic acid Methyl rel-(3aS,14bS)-10-cyclohexyl-13-methoxy-1-methyl-1,2,3,3a,4,14b-hexahydroindolo[2,1-a]pyrrolo[3,2-d][2]benzazepine-7-carboxylate (1 eq.) was dissolved in MeOH/THF (0.02M solution) and 2N NaOH solution (30 eq.) was added. The mixture was warmed to 50° C. overnight. All volatiles were evaporated in vacuo and the residual material was subjected to purification by mass-guided preparative HPLC. The product fractions were lyophilized and the product as obtained as a yellowish powder (TFA salt, 59%). $^1$H-NMR analysis indicated the cis-configuration. $^1$H NMR (400 MHz, DMSO-$d_6$, 300 K) δ 8.19 (s, 1H), 7.92 (d, 1H, J 8.48), 7.67 (d, 1H, J 8.44), 7.50 (d, 1H, J 8.59), 7.33 (dd, 1H, J 2.52+8.54), 7.26 (d, 1H, J 2.45), 4.70 (t, 1H, J 9.80), 4.55 (d, 1H, J 14.32), 3.90 (s, 3H), 3.72 (d, 1H, J 12.49), 3.39-3.37 (m, 1H), 2.94-2.92 (m, 2H), 2.63-2.61 (m, 2H), 2.08-1.74 (m, 7H), 1.60-1.16 (m, 4H); MS ($ES^+$): 445.4 ($M+H^+$).

EXAMPLE 13 rel-(3aS,14bS)-10-cyclohexyl-13-hydroxy-1-methyl-1,2,3,3a,4,14b-hexahydroindolo[2,1-a]pyrrolo[3,2-d][2]benzazepine-7-carboxylic acid

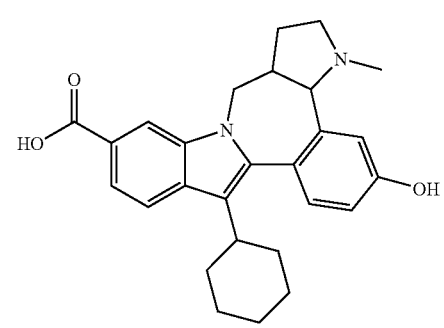

Methyl rel-(3aS,14bS)-10-cyclohexyl-13-methoxy-1-methyl-1,2,3,3a,4,14b-hexahydroindolo[2,1-a]pyrrolo[3,2-d][2]benzazepine-7-carboxylate (Example 12, Step 8, 1 eq.) was dissolved in DCM and the solution was cooled to −78° C. With stirring under argon atmosphere a 1M solution of boron tribromide (2 eq.) in hexanes was added. The mixture was left stirring at −78° C. for 3 h and then allowed to warm to RT overnight. LC-MS indicated a 2:1 mixture of mono-demethylated material and starting material. A further 5 eq. of BBr$_3$ in hexanes was added and stirring was continued at RT. After 3 h all material was transformed into bis-demethylated material. The mixture was diluted with DCM and extracted with 0.5 N HCl. The aq. solution was washed with DCM and with EtOAc. The aq. phase was lyophilized and the product obtained as a brownish powder. This material was purified by mass-guided preparative HPLC. After lyophilization the TFA salt was obtained as a colorless powder. (21%). $^1$H NMR (400 MHz, DMSO-d$_6$, 300 K) δ 7.90 (d, 1H, J 8.44), 7.67-7.65 (m, 2H), 7.39 (d, 1H, J 8.44), 7.12-7.10 (m, 1H), 7.03 (d, 1H, J 2.04), 4.64-4.50 (m, 2H), 3.82-3.35 (m, 2H), 3.18-2.80 (m, 3H), 2.59 (d, 2H, J 4.48), 2.08-1.76 (m, 8H), 1.59-1.24 (m, 4H), 3H hidden under water signal; MS (ES$^+$): 431.6 (M+H$^+$).

EXAMPLE 14 rel-(3aS,14bS)-10-cyclohexyl-1-methyl-13-(pyridin-3-ylmethoxy)-1,2,3,3a,4,14b-hexahydroindolo[2,1-a]pyrrolo[3,2-d][2]benzazepine-7-arboxylic acid

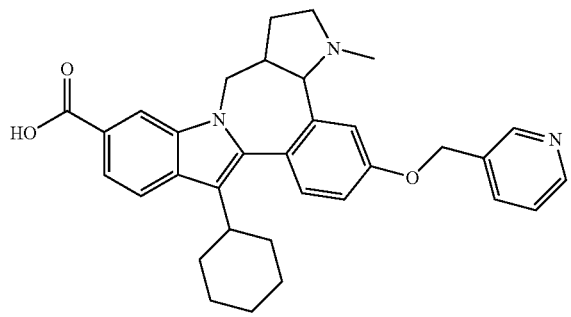

Step 1: rel-(3aS,14bS)-methyl 10-cyclohexyl-13-hydroxy-1-methyl-1,2,3,3a,4,14b-hexahydroindolo[2,1-a]pyrrolo[3,2-d][2]benzazepine-7-carboxylate Crude rel-(3aS,14bS)-10-cyclohexyl-13-hydroxy-1-methyl-1,2,3,3a,4,14b-hexahydroindolo[2,1-a]pyrrolo[3,2-d][2]benzazepine-7-carboxylic acid (Example 13, 1 eq.) was dissolved in toluene/MeOH/DCM and TMS-diazomethane (1.2 eq.) was added. The mixture was left stirring at RT. After 10 min the formation of a mono-methylated compound was observed. Additional TMS-diazomethane (3 eq.) was added and stirring was continued at RT. After 180 min 2N HCl in Et$_2$O was added and the mixture was left stirring for 5 min. All volatiles were evaporated in vacuo and the residual material was dissolved in DCM. The solution was washed with saturated aq. NaHCO$_3$ solution and with brine. After drying over Na$_2$SO$_4$ all volatiles were evaporated in vacuo. The residual material was lyophilized, giving a yellow amorphous powder which was used without further characterization in the next reaction.

Step 2: methyl rel-(3aS,14bS)-10-cyclohexyl-1-methyl-13-(pyridin-3-ylmethoxy)-1,2,3,3a,4,14b-hexahydroindolo[2,1-a]pyrrolo[3,2-d][2]benzazepine-7-carboxylate Methyl rel-(3aS,14bS)-10-cyclohexyl-13-hydroxy-1-methyl-1,2,3,3a,4,14b-hexahydroindolo[2,1-a]pyrrolo[3,2-d][2]benzazepine-7-carboxylate (1 eq.) was dissolved in DMF and NaH (2.2 eq.) was added. The dark brown mixture was left stirring for 15 min at RT, then 3-(chloromethyl)pyridine hydrochloride (1.1 eq.) was added and the mixture was left stirring overnight. All volatiles were evaporated in vacuo and the residual material was taken up in Et$_2$O. The solution was washed with aq. saturated NaHCO$_3$ solution and with brine. After drying over Na$_2$SO$_4$ all volatiles were evaporated in vacuo. The residual material was purified by flash chromatography (PE:EtOAc 1:1+2% MeOH). After evaporation of the solvents the residual material was taken into EtOAc and filtered. The product was obtained as a yellowish glassy solid; (42%).

Step 3: rel-(3aS,14bS)-10-cyclohexyl-1-methyl-13-(pyridin-3-ylmethoxy)-1,2,3,3a, 4,14b-hexahydroindolo[2,1-a]pyrrolo[3,2-d][2]-benzazepine-7-carboxylic acid Methyl rel-(3aS,14bS)-10-cyclohexyl-1-methyl-13-(pyridin-3-ylmethoxy)-1,2,3,3a,4,14b-hexahydroindolo[2,1-a]pyrrolo[3,2-d][2]benzazepine-7-carboxylate (1 eq.) was dissolved in THF/MeOH and a 1 M solution of KOH in water (5 eq.) was added. The mixture was warmed to 50° C. After 7 h the mixture was cooled to RT and left stirring overnight. Then all volatiles were evaporated and the residual material was purified by mass-guided preparative HPLC. After lyophilization the product was obtained as an amorphous yellowish solid. (TFA salt, 64%). $^1$H NMR (400 MHz, DMSO-d$_6$, 300 K) δ 8.84 (d, 1H, J 6.08), 8.68 (d, 1H, J 4.52), 8.31-8.10 (m, 2H), 7.93-7.88 (m, 1H), 7.68-7.61 (m, 2H), 7.53-7.35 (m, 3H), 5.34 (s, 2H), 4.75-4.54 (m, 2H), 3.83-3.71 (m, 1H), 3.37-3.26 (m, 1H), 2.95-2.79 (m, 3H), 2.62-2.61 (m, 2H), 2.07-1.76 (m, 7H), 1.57-1.24 (m, 4H), 2H hidden under DMSO signal; MS (ES$^+$): 522.4 (M+H$^+$).

EXAMPLE 15

(2E)-3-[4-({[1-({[rel-(3aS,14bS)-10-cyclohexyl-13-methoxy-1-methyl-1,2,3,3a,4,14b-hexahydroindolo[2,1-a]pyrrolo[3,2-d][2]benzazepin-7-yl]carbonyl}amino)cyclopentyl]carbonyl}amino)phenyl]acrylic acid

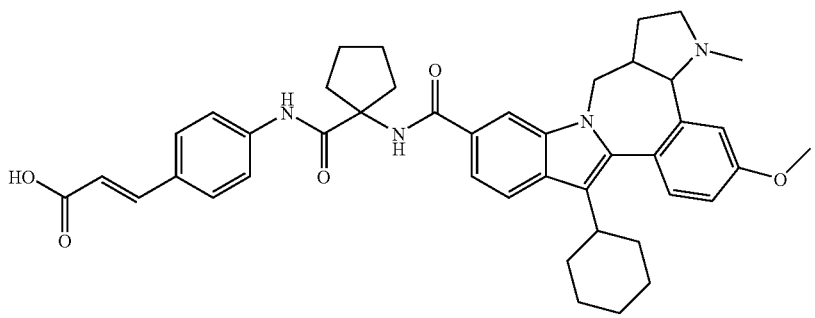

Step 1: ethyl (2E)-3-[4-({[1-({[rel-(3aS,14bS)-10-cyclohexyl-13-methoxy-1-methyl-1,2,3,3a,4,14b-hexahydroindolo[2,1-a]pyrrolo[3,2-d][2]benzazepin-7-yl]carbonyl}amino)cyclopentyl]carbonyl}amino)phenyl]acrylate rel-(3aS,14bS)-10-cyclohexyl-13-methoxy-1-methyl-1,2,3,3a,4,14b-hexahydroindolo[2,1-a]pyrrolo[3,2-d][2]benzazepine-7-carboxylic acid (Example 12, Step 9, 1 eq.) and ethyl (2E)-3-(4-{[(1-aminocyclopentyl)carbonyl]amino}phenyl)acrylate hydrochloride (2 eq., prepared as described in WO2006/029912) were dissolved in DMF and HATU (2 eq.) was added, followed by DIPEA (8 eq.). The mixture was left stirring at RT overnight. All volatiles were evaporated in vacuo and the residual material was dissolved in EtOAc. The solution was washed with 1N HCl, aq. saturated NaHCO$_3$ solution and with brine. After drying over Na$_2$SO$_4$ all volatiles were evaporated in vacuo. The product was obtained as a yellow glassy solid which was used without further characterization in the next reaction.

Step 2: (2E)-3-[4-({[1-({[rel-(3aS,14bS)-10-cyclohexyl-13-methoxy-1-methyl-1,2,3,3a,4,14b-hexahydroindolo[2,1-a]pyrrolo[3,2-d][2]benzazepin-7-yl]carbonyl}amino)cyclopentyl]carbonyl}amino)phenyl]acrylic acid Ethyl (2E)-3-[4-({[1-({[rel-(3aS,14bS)-10-cyclohexyl-13-methoxy-1-methyl-1,2,3,3a,4,14b-hexahydroindolo[2,1-a]pyrrolo[3,2-d][2]benzazepin-7-yl]carbonyl}amino)cyclopentyl]carbonyl}amino)phenyl]acrylate (1 eq.) was dissolved in THF/MeOH and 1M KOH solution (5 eq.) was added. The mixture was warmed overnight to 50° C. All volatiles were evaporated in vacuo and the residual material was purified by mass-guided preparative HPLC. After lyophilization the product was obtained as a yellowish amorphous solid. (TFA salt, 51%). $^1$H NMR (400 MHz, DMSO-d$_6$, 300 K) δ 9.68 (s, 1H), 8.36-8.29 (m, 1H), 8.21-8.18 (m, 1H), 7.88-7.83 (m, 1H), 7.67-7.58 (m, 5H), 7.54-7.48 (m, 2H), 7.34-7.29 (m, 2H), 6.39 (d, 1H, J 15.93), 4.75-4.70 (m, 1H), 4.55-4.51 (m, 1H), 3.91 (s, 3H), 3.78-3.75 (m, 1H), 3.45-3.39 (m, 1H), 2.93-2.65 (m, 4H), 2.38-2.34 (m, 2H), 2.11-1.62 (m, 14H), 1.42-1.15 (m, 4H), 2H hidden under DMSO signal; MS (ES$^+$): 701.5 (M+H$^+$).

EXAMPLE 16 rel-(3aS,14bS)-10-cyclohexyl-1-[(2-pyrrolidin-1-ylethoxy)carbonyl]-1,2,3,3a,4,14b-hexahydroindolo[2,1-a]pyrrolo[3,2-d][2]benzazepine-7-carboxylic acid

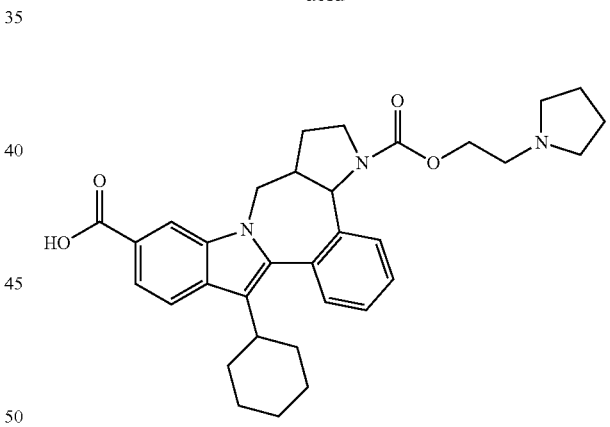

Step 1: Methyl 3-cyclohexyl-2-[2-(hydroxymethyl)phenyl]-1H-indole-6-carboxylate 2-bromo-3-cyclohexyl indole-6-carboxylic acid methyl ester (1 eq., prepared as described in WO2004/087714 from commercially available methyl indole-6-carboxylate) was mixed with [2-(hydroxymethyl)phenyl]boronic acid (1.5 eq.) and bis(triphenylphosphine)palladium dichloride (0.2 eq.) was added. The mixture was degassed and dioxane and 2M aq. Na$_2$CO$_3$ solution (2 eq.) were added. The mixture was heated under N$_2$-atmosphere to 110° C. for 1 h then diluted with EtOAc and washed with brine. The organic phase was dried over Na$_2$SO$_4$ and evaporated in vacuo. The residual material was subjected to flash chromatography (PE:EtOAc, 4:1). After evaporation of the solvents the product was obtained as orange solid (95%). MS (ES$^+$): 364.3 (M+H$^+$).

Step 2: Methyl 3-cyclohexyl-2-(2-{[(triisopropylsilyl)oxy]methyl}phenyl)-1H-indole-6-carboxylate To an ice-cooled solution of methyl 3-cyclohexyl-2-[2-(hydroxymethyl)phenyl]-1H-indole-6-carboxylate and imidazole (2 eq.) in DMF (0.4 M), chloro(triisopropyl)silane (2 eq.) was added dropwise. The mixture was stirred at RT for 7 h, diluted with EtOAc, washed with sat. aq. NH₄Cl and brine. The organic phase was dried over Na₂SO₄ and evaporated in vacuo. The residual material was subjected to flash chromatography (PE:EtOAc, 6:1). After evaporation of the solvents the product was obtained as colourless oil (97%). MS (ES⁻): 519.7 (M−H⁺).

Step 3: Methyl 1-allyl-3-cyclohexyl-2-(2-{[(triisopropylsilyl)oxy]methyl}phenyl)-1H-indole-6-carboxylate To a solution of methyl 3-cyclohexyl-2-(2-{[(triisopropylsilyl)oxy]methyl}phenyl)-1H-indole-6-carboxylate in DMF (0.13 M) NaH (2 eq.) was added. After 20 min. allyl bromide (1.5 eq.) was added and the mixture stirred at RT for 2 h, diluted with Et₂O, washed with sat aq. NH₄Cl and brine. The organic phase was dried over Na₂SO₄ and evaporated in vacuo. The residual material was subjected to flash chromatography (PE:EtOAc, 10:1). After evaporation of the solvents the product was obtained as yellow solid (67%).

Step 4: Methyl 1-allyl-3-cyclohexyl-2-[2-(hydroxymethyl)phenyl]-1H-indole-6-carboxylate Tetrabutylammonium fluoride (1.3 eq., 1M solution in THF) was added dropwise to an ice cooled solution of methyl 1-allyl-3-cyclohexyl-2-(2-{[(triisopropylsilyl)oxy]methyl}phenyl)-1H-indole-6-carboxylate in THF (0.036M). The mixture was stirred at RT for 1 h then diluted with EtOAc, washed with saturated aq. NH₄Cl, water and brine. The organic phase was dried over Na₂SO₄ and evaporated in vacuo. The residual material was subjected to flash chromatography (PE:EtOAc, 4:1). After evaporation of the solvent the product was obtained as colourless solid (95%). MS (ES⁺): 404.3 (M+H⁺).

Step 5: Methyl 1-allyl-3-cyclohexyl-2-(2-formylphenyl)-1H-indole-6-carboxylate Oxalyl chloride (2.5 eq., 2M solution in DCM) was added at −70° C. under nitrogen atmosphere to a solution of DMSO (5 eq.) in anhydrous DCM and the mixture was stirred for 30 min; a solution of methyl 1-allyl-3-cyclohexyl-2-[2-(hydroxymethyl)phenyl]-1H-indole-6-carboxylate in DCM was then added and stirring was continued at the same temperature for 30 min. before NEt₃ (8 eq.) was added. After stirring for 20 min. at 0° C. the mixture was diluted with DCM, then washed with water, 1N HCl, saturated aq. NaHCO₃ solution and brine. The organic phase was dried over Na₂SO₄ and evaporated in vacuo. The residual material was used in the next step without purification. MS (ES⁺): 402.2 (M+H⁺).

Step 6: methyl rel-(3aS,14bS)-10-cyclohexyl-1,2,3,3a,4,14b-hexahydroindolo[2,1-a]pyrrolo[3,2-d][2]benzazepine-7-carboxylate A DMF-solution (0.042 M) of methyl 1-allyl-3-cyclohexyl-2-(2-formylphenyl)-1H-indole-6-carboxylate, glycine (10 eq.) and NEt₃ (8 eq.) was heated under nitrogen atmosphere at 150° C. After 2 h all volatiles were removed in vacuo and the residual material was subjected to flash chromatography (EtOAc:PE 75:25, NEt₃ 0.5%). After evaporation of the solvents the product was obtained as a colourless solid (60%). MS (ES⁺): 415.3 (M+H⁺).

Step 7: 7-methyl rel-(3aS,14bS)-1-(2-pyrrolidin-1-ylethyl)-10-cyclohexyl-2,3,3a,14b-tetrahydroindolo[2,1-a]pyrrolo[3,2-d][2]benzazepine-1,7(4H)-dicarboxylate To a solution of methyl rel-(3aS,14bS)-10-cyclohexyl-1,2,3,3a,4,14b-hexahydroindolo[2,1-a]pyrrolo[3,2-d][2]benzazepine-7-carboxylate in DMF (0.1 M) 1-(2-chloroethyl)pyrrolidine hydrochloride (1.2 eq.) and K₂CO₃ (3 eq.) were added. After 2 h at 60° C. the solvent was removed in vacuo and the residual material was purified by flash chromatography (EtOAc:PE:MeOH:NEt₃ 70:25:3:2). After evaporation of the solvent the product was obtained with 77% yield. MS (ES⁺): 556.4 (M+H⁺).

Step 8: rel-(3aS,14bS)-10-cyclohexyl-1-[(2-pyrrolidin-1-ylethoxy)carbonyl]-1,2,3,3a,4,14b-hexahydroindolo[2,1-a]pyrrolo[3,2-d][2]benzazepine-7-carboxylic acid To a 0.05M solution of methyl rel-(3aS,14bS)-7-methyl 1-(2-pyrrolidin-1-ylethyl)-10-cyclohexyl-2,3,3a,14b-tetrahydroindolo[2,1-a]pyrrolo[3,2-d][2]benzazepine-1,7(4H)-dicarboxylate in dioxane, 1M aq. KOH solution (10 eq.) was added and the mixture was heated to 70° C. After 1.5 h the mixture was neutralized by addition of 1N HCl (10 eq.) and then all volatiles were removed in vacuo. The product was isolated by prep. RP-HPLC (Waters X-Terra column). After lyophilisation a yellow solid was obtained (TFA salt, 19%). ¹H NMR (400 MHz, DMSO-d₆, TFA-d, 300 K) δ 8.19-8.18 (m, 2H), 7.90-7.87 (m, 2H), 7.62 (d, 2H, J 7.8), 7.51-7.48 (m, 4H), 7.41-7.39 (m, 2H), 7.26-7.24 (m, 2H), 4.80-4.74 (m, 2H), 4.70 (d, 2H, J 8.0), 4.57 (d, 2H, J 8.0), 4.27-4.26 (m, 2H), 4.16-4.09 (m, 2H), 3.82-3.71 (m, 2H), 3.58-3.45 (m, 6H), 3.29-3.22 (m, 4H), 3.18-3.08 (m, 4H), 2.87-2.86 (m, 2H), 2.07-1.86 (m, 14H), 1.79-1.52 (m, 14H), 1.37-1.13 (m, 6H). MS (ES⁺): 542.4 (M+H⁺).

EXAMPLE 17 rel-(3aS,14bS)-10-cyclohexyl-1-[(dimethylamino)acetyl]-1,2,3,3a,4,14b-hexahydroindolo[2,1-a]pyrrolo[3,2-d][2]benzazepine-7-carboxylic acid

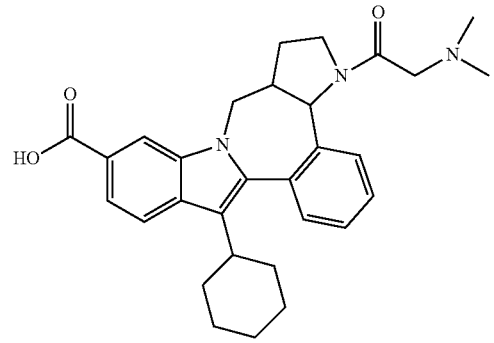

Step 1: methyl rel-(3aS,14bS)-10-cyclohexyl-1-[(dimethylamino)acetyl]-1,2,3,3a,4,14b-hexahydroindolo[2,1-a]pyrrolo[3,2-d][2]-benzazepine-7-carboxylate To a 0.1 M solution of methyl rel-(3aS,14bS)-10-cyclohexyl-1,2,3,3a,4,14b-hexahydroindolo[2,1-a]pyrrolo[3,2-d][2]benzazepine-7-carboxylate (Example 16, Step 6) in DCM, N,N-dimethylglycine (0.7 eq.), HATU (1 eq.) and DIPEA (2.5 eq.) were added and the mixture was stirred at RT for 18 h. The solvent was removed in vacuo and the residual material was purified by flash chromatography (PE:EtOAc, 4:1, NEt$_3$ 1%). After evaporation of the solvent the product was obtained with 73% yield as a white solid. MS (ES$^+$): 500.5 (M+H$^+$).

Step 2: rel-(3aS,14bS)-10-cyclohexyl-1-[(dimethylamino)acetyl]-1,2,3,3a,4,14b-hexahydroindolo[2,1-a]pyrrolo[3,2-d][2]benzazepine-7-carboxylic acid To a 0.05M solution of methyl rel-(3aS,14bS)-10-cyclohexyl-1-[(dimethylamino)acetyl]-1,2,3,3a,4,14b-hexahydroindolo[2,1-a]pyrrolo[3,2-d][2]benzazepine-7-carboxylate in dioxane, 1M KOH solution (10 eq.) was added and the mixture was heated to 70° C. After 3 h the mixture was neutralized by addition of 1N HCl (10 eq.) and then all volatiles were removed in vacuo. The product was isolated by prep. RP-HPLC (WATERS X-TERRA column). After lyophilisation a white solid was obtained (TFA salt, 26% yield, mixture of two atropisomers in a ratio 3/1). $^1$H NMR (400 MHz, DMSO-d$_6$+TFA-d, 300 K, major atropisomer) δ 8.20 (s, 1H), 7.91-7.89 (m, 1H), 7.64-7.63 (m, 1H), 7.57-7.42 (m, 3H), 7.27-7.19 (m, 1H), 4.84-4.77 (m, 2H), 4.41 (d, 1H, J 16.2), 4.23 (d, 1H, J 16.2), 3.90-3.82 (m, 1H), 3.58-3.56 (m, 1H), 3.06-3.04 (m, 1H), 2.83-2.79 (m, 6H), 2.17-2.14 (m, 1H), 2.03-1.87 (m, 5H), 1.73-1.55 (m, 4H), 1.39-1.24 (m, 4H); MS (ES$^+$): 486.5 (M+H$^+$).

EXAMPLE 18 rel-(3aS,14bR)-10-cyclohexyl-1-[2-(dimethylamino)ethyl]-1,2,3,3a,4,14b-hexahydroindolo[2,1-a]pyrrolo[3,2-d][2]-benzazepine-7-carboxylic acid

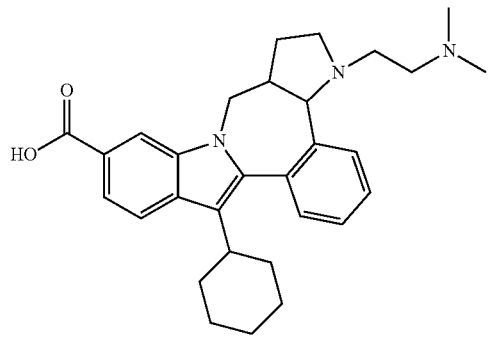

Step 1: Methyl 3-cyclohexyl-1-prop-2-yn-1-yl-2-(2-{[(triisopropylsilyl)oxy]methyl}phenyl)-1H-indole-6-carboxylate To an ice cooled solution of methyl 3-cyclohexyl-2-(2-{[(triisopropylsilyl)oxy]methyl}phenyl)-1H-indole-6-carboxylate in DMF (0.13 M) NaH (2 eq.) was added. After 20 min. propargyl bromide (80% solution in toluene) (1.5 eq.) was added and the mixture stirred at 0° C. for 1 h, diluted with Et$_2$O, washed with sat aq. NH$_4$Cl and brine. The organic phase was dried over Na$_2$SO$_4$ and evaporated in vacuo. The residual material was subjected to flash chromatography (PE:EtOAc, 20:1). After evaporation of the solvents the product was obtained as yellow oil (67%). MS (ES$^+$): 558.7 (M+H$^+$).

Step 2: Methyl 3-cyclohexyl-2-[2-(hydroxymethyl)phenyl]-1-prop-2-yn-1-yl-1H-indole-6-carboxylate Tetrabutylammonium fluoride (1.3 eq., 1M solution in THF) was added dropwise to an ice cooled solution of methyl 3-cyclohexyl-1-prop-2-yn-1-yl-2-(2-{[(triisopropylsilyl)oxy]methyl}phenyl)-1H-indole-6-carboxylate in THF (0.036M). The mixture was stirred at 0° C. for 1 h then diluted with EtOAc, washed with saturated aq. NH$_4$Cl, water and brine. The organic phase was dried over Na$_2$SO$_4$ and evaporated in vacuo. The residual material was subjected to flash chromatography (PE:EtOAc, 3:1). After evaporation of the solvents the product was obtained as white solid (63%). MS (ES$^+$): 402.6 (M+H$^+$).

Step 3: Methyl 3-cyclohexyl-2-(2-formylphenyl)-1-prop-2-yn-1-yl-1H-indole-6-carboxylate Oxalyl chloride (2.5 eq., 2M solution in DCM) was added at −70° C. under N$_2$— atmosphere to a solution of DMSO (5 eq.) in anhydrous DCM and the mixture was stirred for 30 min; a solution of methyl 3-cyclohexyl-2-[2-(hydroxymethyl)phenyl]-1-prop-2-yn-1-yl-1H-indole-6-carboxylate in DCM was then added and stirring was continued at the same temperature for 30 min. before NEt$_3$ (8 eq.) was added. After stirring at 0° C. for 20 min. the mixture was diluted with DCM, washed with water, 1N HCl, saturated aq. NaHCO$_3$ solution and brine. The organic phase was dried over Na$_2$SO$_4$ and evaporated in vacuo. The obtained yellow solid was used in the next step without purification. MS (ES$^+$): 400.5 (M+H$^+$).

Step 4: Methyl 1-{2-[(tert-butoxycarbonyl)amino]ethyl}-10-cyclohexyl-1,4 dihydroindolo[2,1-a]pyrrolo[3,2-d][2]benzazepine-7-carboxylate and methyl rel-(3aS,14bR)-1-{2-[(tert-butoxycarbonyl)amino]ethyl}-10-cyclohexyl-1,2,3,3a,4,14b-hexahydroindolo[2,1-a]pyrrolo[3,2-d][2]benzazepine-7-carboxylate A toluene solution (0.042 M) of methyl-3-cyclohexyl-2-(2formylphenyl)-1-prop-2-yn-1-yl-1H-indole-6-carboxylate and ({2-[(tert-butoxycarbonyl)amino]ethyl}amino)acetic acid (1.5 eq., prepared according to J. Org. Chem. 2001, 66, 4915) was heated under N$_2$— atmosphere at 140° C. using a Dean Stark trap. After 6 h all volatiles were removed in vacuo and the residual material was subjected to flash chromatography (PE:EtOAc, 5:1). After evaporation of the solvent methyl-1-{2-[(tert-butoxycarbonyl)amino]ethyl}-10-cyclohexyl-1,4-dihydroindolo[2,1-a]pyrrolo[3,2-d][2]benzazepine-7-carboxylate (MS (ES$^+$): 554.3 (M+H$^+$)) and methyl-1-{2-[(tert-butoxycarbonyl)amino]ethyl}-10-cyclohexyl-1,2,4,14b-tetrahydroindolo[2,1-a]pyrrolo[3,2-d][2]benzazepine-7-carboxylate (MS (ES$^+$): 556.3 (M+H$^+$)) were obtained as a mixture in a ratio 1/1.4 with an overall yield of 92%. To a 0.05M solution of that mixture in EtOAc, Pd/C (10 wt. %, 0.15 eq.) was added and the mixture was left stirring under H₂-atmosphere for 4 h at RT. After filtration on a CELITE pad the crude was purified by flash chromatography (PE: EtOAc, 1:1) to give methyl 1-{2-[(tert-butoxycarbonyl) amino]ethyl}-10-cyclohexyl -1,4-dihydroindolo[2,1-a]pyrrolo[3,2-d][2]benzazepine-7-carboxylate (32%) and methyl rel-(3aS,14bR)-1-{2-[(tert-butoxycarbonyl)amino]ethyl}-10-cyclohexyl-1,2,3,3a,4,14b -hexahydroindolo[2,1-a]pyrrolo[3,2-d][2]benzazepine-7-carboxylate (22%), MS (ES⁺): 558.6 (M+H⁺).

Step 5: methyl rel-(3aS,14bR)-1-(2-aminoethyl)-10-cyclohexyl-1,2,3,3a,4,14b-hexahydroindolo[2,1-a] pyrrolo[3,2-d][2]-benzazepine-7-carboxylate A solution of methyl rel-(3aS,14bR)-1-{2-[(tert-butoxycarbonyl)amino]ethyl}-10-cyclohexyl-1,2,3,3a,4,14b-hexahydroindolo[2,1-a]pyrrolo[3,2-d][2]benzazepine-7-carboxylate in DCM (0.15M) and TFA (22 eq.) was stirred at RT for 1 h. All volatiles were removed in vacuo and the residual material was used in the next step without purification. MS (ES⁺): 458.6 (M+H⁺).

Step 6: methyl rel-(3aS,14bR)-10-cyclohexyl-1-[2-(dimethylamino)ethyl]-1,2,3,3a,4,14b-hexahydroindolo[2,1-a]pyrrolo[3,2-d][2]-benzazepine-7-carboxylate Methyl rel-(3aS,14bR)-1-(2-aminoethyl)-10-cyclohexyl-1,2,3,3a,4,14b-hexahydroindolo[2,1-a]pyrrolo[3,2-d][2] benzazepine-7-carboxylate (as TFA salt) was dissolved in MeOH (0.1 M) and AcOH (5 eq.) followed by NEt₃ (3 eq.) were added. A solution of formaldehyde in water (37%, 3 eq.) was added and the mixture was left stirring for 10 min. NaCNBH₃ (2 eq.) was added and the mixture was left stirring at RT for 3 h. All volatiles were evaporated and the residual material was dissolved in EtOAc, washed with water, dried over Na₂SO₄ and evaporated in vacuo. The crude material was used in the next step without purification. MS (ES⁺): 486.6 (M+H⁺).

Step 7: rel-(3aS,14bR)-10-cyclohexyl-1-[2-(dimethylamino)ethyl]-1,2,3,3a,4,14b-hexahydroindolo[2,1-a] pyrrolo[3,2-d][2]benzazepine-7-carboxylic acid To a 0.05M solution of methyl rel-(3aS,14bR)-10-cyclohexyl-1-[2-(dimethylamino) ethyl]-1,2,3,3a,4,14b-hexahydroindolo[2,1-a]pyrrolo[3,2-d][2]benzazepine-7-carboxylate in a mixture of MeOH/dioxane 1:1, an aq. KOH solution 1M (10 eq.) was added and the mixture was heated to 70° C. After 1.5 h the mixture was neutralized with 1N HCl (10 eq.) and then the volatiles were removed in vacuo. The product was isolated by prep. RP-HPLC (WATERS X-TERRA column). After lyophilisation a white solid was obtained (TFA salt, 30% yield over three steps). ¹H NMR (400 MHz, DMSO-d₆, TFA-d, 300 K) δ 8.21 (s, 1H), 7.92 (d, 1H, J 8.6), 7.66 (d, 1H, J 8.6), 7.63-7.55 (m, 4H), 4.76 (d, 1H, J 14.9), 4.09 (d, 1H, J 12.4), 3.88-3.77 (m, 2H), 3.59-3.38 (m,4H), 2.77-2.71 (m, 7H), 2.39-2.37 (m, 1H), 2.02-1.88 (m, 4H), 1.76-1.71 (m, 2H), 1.57-1.54 (m, 2H), 1.38-1.13 (m, 5H). MS (ES⁺): 472.5 (M+H⁺).

EXAMPLE 19 rel-(3aS,14bR)-10-cyclohexyl-1-[2-(dimethylamino) ethyl]-13-methoxy-1,2,3,3a,4,14b-hexahydroindolo [2,1-a]pyrrolo[3,2-d][2]benzazepine-7-carboxylic acid

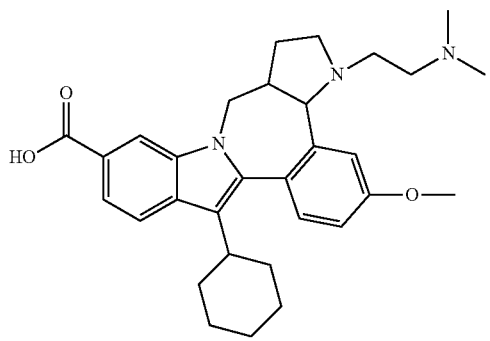

Step 1: Methyl-3-cyclohexyl-2-(4-methoxy-2-{[(triisopropylsilyl)oxy]methyl}phenyl)-1-prop-2-yn-1-yl-1H-indole-6-carboxylate To an ice cooled solution of methyl-3-cyclohexyl-2-(4-methoxy-2-{[(triisopropylsilyl) oxy]methyl}phenyl)-1H-indole-6-carboxylate (Example 12, Step 4) in DMF (0.13 M) 60% NaH (2 eq.) was added. After 20 min. propargyl bromide (solution 80% in toluene) (1.5 eq.) was added and the mixture stirred at 0° C. for 1 h, diluted with Et₂O, washed with sat aq. NH₄Cl and brine. The organic phase was dried over Na₂SO₄ and evaporated in vacuo. The residual material was subjected to flash chromatography (PE:EtOAc, 20:1). After evaporation of the solvents the product was obtained as a white solid (96%). MS (ES⁺): 588.7 (M+H⁺).

Step 2: Methyl 3-cyclohexyl-2-[2-(hydroxymethyl)-4-methoxyphenyl]-1-prop-2-yn-1-yl-1H-indole-6-carboxylate Tetrabutylammonium fluoride (1.3 eq., 1M solution in THF) was added dropwise to an ice cooled solution of methyl 3-cyclohexyl-2-(4-methoxy-2-{[(triisopropylsilyl)oxy] methyl}phenyl)-1-prop-2-yn-1-yl-1H-indole-6-carboxylate in THF (0.036M). The mixture was stirred at 0° C. for 1 h then diluted with EtOAc, washed with saturated aq. NH₄Cl, water and brine. The organic phase was dried over Na₂SO₄ and evaporated in vacuo. The residual material was subjected to flash chromatography (PE:EtOAc, 3:1). After evaporation of the solvent the product was obtained as white solid (64%). MS (ES⁺): 432.5 (M+H⁺).

Step 3: Methyl 3-cyclohexyl-2-(2-formyl-4-methoxyphenyl)-1-prop-2-yn-1-yl-1H-indole-6-carboxylate Oxalyl chloride (2.5 eq., 2M solution in DCM) was added at −70° C. under nitrogen atmosphere over a solution of DMSO (5 eq.) in anhydrous DCM and the mixture was stirred for 30 min; a solution of methyl 3-cyclohexyl-2-[2-(hydroxymethyl)-4-methoxyphenyl]-1-prop-2-yn-1-yl-1H-indole-6-carboxylate in DCM was then added and stirring was continued at the same temperature for 30 min. before NEt₃ (8 eq.) was added. After stirring at 0° C. for 20 min. the mixture was diluted with DCM, washed with water, 1N HCl, saturated aq. NaHCO₃ solution and brine. The organic phase was dried over Na₂SO₄ and evaporated in vacuo. The obtained yellow solid was used in the next step without purification. MS (ES⁺): 430.5 (M+H⁺).

Step 4: rel-(3aS,14bR)-methyl-10-cyclohexyl-13-methoxy-1,2,3,3a,4,14b-hexahydroindolo[2,1-a]pyrrolo[3,2-d][2]benzazepine-7-carboxylate A solution (0.042 M) of methyl-3-cyclohexyl-2-(2-formyl-4-methoxyphenyl)-1-prop-2-yn-1-yl-1H-indole-6-carboxylate, glycine (10 eq.) and NEt₃ (8 eq.) in DMF was heated under N₂-atmosphere at 140° C. After 1 h all volatiles were removed in vacuo and the crude was taken up with water and extracted with EtOAc. The organic phase was dried over Na₂SO₄ and evaporated in vacuo. Pd/C (10 wt. %, 0.15 eq.) was added to a 0.05M solution of the crude material in EtOAc and the mixture was left stirring under H₂-atmosphere for 4 h at RT. After filtration on a CELITE pad the crude was purified by flash chromatography (PE:EtOAc, 1:1, NEt₃₁%) to give methyl rel-(3aS,14bR)-10-cyclohexyl-13-methoxy-1,2,3,3a,4,14b-hexahydroindolo[2,1-a]pyrrolo[3,2-d][2]benzazepine-7-carboxylate (43%), MS (ES⁺): 445.4 (M+H⁺).

Step 5: methyl rel-(3aS,14bR)-1-{2-[(tert-butoxycarbonyl)amino]ethyl}-10-cyclohexyl-13-methoxy-1,2,3,3a,4,14b-hexahydroindolo[2,1-a]pyrrolo[3,2-d][2]-benzazepine-7-carboxylate Methyl rel-(3aS,14bR)-10-cyclohexyl-13-methoxy-1,2,3,3a,4,14b-hexahydroindolo[2,1-a]pyrrolo[3,2-d][2]benzazepine-7-carboxylate was dissolved in MeOH (0.1 M) and AcOH (5 eq.) followed by NEt₃ (3 eq.) were added. A solution of N-Boc-aminoacetaldehyde (3 eq.) was added and the mixture was left stirring for 10 min. NaCNBH₃ (2 eq.) was added and the mixture was left stirring at RT for 2 h. All volatiles were evaporated and the residual material was dissolved in EtOAc, washed with water, dried over Na₂SO₄ and evaporated in vacuo. The crude material was used in the next step without purification. MS (ES⁺): 588.7 (M+H⁺).

Step 6: methyl rel-(3aS,14bR)-1-(2-aminoethyl)-10-cyclohexyl-13-methoxy-1,2,3,3a,4,14b-hexahydroindolo[2,1-a]pyrrolo[3,2-d][2]benzazepine-7-carboxylate A solution of methyl rel-(3aS,14bR)-1-{2-[(tert-butoxycarbonyl)amino]ethyl}-10-cyclohexyl-13-methoxy-1,2,3,3a,4,14b-hexahydroindolo[2,1-a]pyrrolo[3,2-d][2]benzazepine-7-carboxylate in DCM (0.15M) and TFA (22 eq.) was stirred at RT for 3 h. All volatiles were removed in vacuo and the residual material was used in the next step without purification. MS (ES⁺): 488.6 (M+H⁺).

Step 7: methyl rel-(3aS,14bR)-10-cyclohexyl-1-[2-(dimethylamino)ethyl]-13-methoxy-1,2,3,3a,4,14b-hexahydroindolo[2,1-a]pyrrolo[3,2-d][2]benzazepine-7-carboxylate Methyl rel-(3aS,14bR)-1-(2-aminoethyl)-10-cyclohexyl-13-methoxy-1,2,3,3a,4,14b-hexahydroindolo[2,1-a]pyrrolo[3,2-d][2]benzazepine-7-carboxylate (as TFA salt) was dissolved in MeOH (0.1 M) and AcOH (5 eq.) followed by NEt₃ (3 eq.) were added. A solution of formaldehyde in water (37%, 3 eq.) was added and the mixture was left stirring for 10 min. NaCNBH₃ (2 eq.) was added and the mixture was left stirring at RT for 5 h. All volatiles were evaporated and the residual material was dissolved in EtOAc, washed with water, dried over Na₂SO₄ and evaporated in vacuo. The crude material was used in the next step without purification. MS (ES⁺): 516.6 (M+H⁺).

Step 8: rel-(3aS,14bR)-10-cyclohexyl-1-[2-(dimethylamino)ethyl]-3-methoxy-1,2,3,3a,4,14b-hexahydroindolo[2,1-a]pyrrolo[3,2-d][2]-benzazepine-7-carboxylic acid To a 0.05M solution of methyl rel-(3aS,14bR)-10-cyclohexyl-1-[2-(dimethylamino)ethyl]-13-methoxy-1,2,3,3a,4,14b-hexahydroindolo[2,1-a]pyrrolo[3,2-d][2]benzazepine-7-carboxylate in a mixture of MeOH/dioxane 1:1, an aq. KOH solution 1M (5 eq.) was added and the mixture was heated to 70° C. After 2 h the mixture was neutralized with an aq. solution of 1N HCl (5 eq.) and then all volatiles were removed in vacuo. The product was isolated by prep. RP-HPLC (WATERS X-TERRA column). After lyophilisation a white solid was obtained (TFA salt, 12% yield over three steps). ¹H NMR (400 MHz, CDCl₃+TFA-d, 300 K) δ 8.09 (s, 1H), 7.94 (d, 1H, J 8.6), 7.83 (d, 1H, J 8.6), 7.51 (d, 1H, J 8.3), 7.12-7.09 (m, 2H), 4.51 (d, 1H, J 15.7), 4.26-4.23 (m, 1H), 4.00-3.95 (m, 3H), 3.88 (s, 3H), 3.75-3.73 (m, 1H), 3.49-3.41 (m, 2H), 2.98 (s, 6H), 2.94-2.92 (m, 1H), 2.86-2.76 (m, 1H), 2.52-2.51 (m, 1H), 2.06-1.93 (m, 5H), 1.79-1.77 (m, 2H), 1.55-1.19 (m, 5H). MS (ES⁺): 502.6 (M+H⁺).

EXAMPLE 20 cis-(3a,14b)-10-cyclohexyl-3-methyl-1,2,3,3a,4,14b-hexahydroindolo[2,1-a]pyrrolo[2,3-d][2]benzazepine-7-carboxylic acid

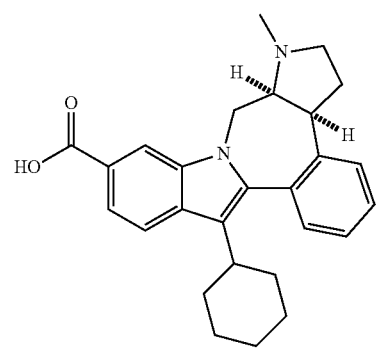

Step 1: Methyl 3-cyclohexyl-2-(2-vinylphenyl)-1H-indole-6-carboxylate

Following the procedure described in Example 12, Step 4, the title compound was obtained from 2-bromo-3-cyclohexyl indole-6-carboxylic acid methyl ester (1 eq., prepared as described in WO2004/087714 from commercially available methyl indole-6-carboxylate) in dioxane and vinylboronic acid (1.5 eq.). Flash chromatography (PE:EtOAc, 12:1) gave the product (69%) as an off-white foam. MS (ES$^+$): 360.4 (M+H)$^+$.

Step 2: Methyl 3-cyclohexyl-1-(2,2-dimethoxy-ethyl)-2-(2-vinylphenyl)-1H-indole-6-carboxylate To a solution of the foregoing product (1 eq.) in anhydrous DMF (0.16 M) was added portionwise NaH (1.5 eq., 60% in mineral oil). The resulting mixture was stirred for 40 min at RT and the heated for 10 min at 60° C. The resulting yellow solution was cooled to RT, and at this point KI (0.1 eq.) and 2-bromo-1,1-dimethoxyethane (2 eq.) were added. The reaction mixture was heated to 90° C. After 3 h the reaction was cooled to RT, most of the DMF was removed and the residue taken into EtOAc. The organic phase was washed with water and brine, dried over Na$_2$SO$_4$ and was concentrated to give the crude product which was purified by flash chromatography (PE/EtOAc 9.1). The product (71%) was obtained as colorless foam. MS (ES$^+$): 448.3 (M+H)$^+$.

Step 3: Methyl 10-cyclohexyl-3-methyl-1,2,3,3a,4,14b-hexahydroindolo[2,1-a]pyrrolo[2,3-d][2]-benzazepine-7-carboxylate The foregoing compound (1 eq.) was dissolved in THF (0.28 M) and the resulting solution was cooled to 0° C. Concentrated hydrochloric acid (25 eq.) was added, the ice-bath was removed and the reaction mixture was stirred at RT. After 2 h the temperature was raised to 50° C. and stirred at this temperature for 1 h. After cooling to RT, some of the THF was removed in vacuo and the remaining residue was taken into EtOAc. The organic phase was washed with aq. sat. NaHCO$_3$, water and brine and dried over Na$_2$SO$_4$. Evaporation gave the crude aldehyde and its hydrate as an orange oil, which was used without further purification. MS (ES$^+$): 402.6 (M+H)$^+$. The foregoing crude aldehyde (1 eq.) was dissolved in a mixture of toluene and DMF (4:1, 0.4M) and sarcosine (1 eq.) was added. The solution was heated under reflux on a Dean-Stark trap overnight. The reaction was then cooled to RT, taken into EtOAc and washed with aqueous HCl (1 N), water and brine and dried over Na$_2$SO$_4$. Removal of the volatiles gave a dark red residue, which was purified by flash chromatography (PE/EtOAc 10:1, then 5:1+0.4% NEt$_3$) to give the product as a yellow oil (7%). MS (ES$^+$): 429.4 (M+H)$^+$.

Step 4: cis-(3a, 14b)-10-cyclohexyl-3-methyl-1,2,3,3a,4,14b-hexahydroindolo[2,1-a]pyrrolo[2,3-d][2]benzazepine-7-carboxylic acid The foregoing compound (1 eq.) was dissolved in THF (0.05 M), KOH (1 N, 10 eq.) was added and the resulting mixture was stirred overnight at RT. The reaction was brought to pH 4 by the addition of aqueous HCl (2N) and the resulting mixture was extracted with EtOAc. The combined organic phases were dried over Na$_2$SO$_4$. The solvent was removed in vacuo and the residue was purified by mass-guided preparative RP-HPLC. Lyophilisation of fractions containing the product gave the title compound as its TFA salt (52%, mixture of two atropisomers in a ratio 1.5:1*). $^1$H NMR (400 MHz, DMSO-d$_6$ 300 K) δ 9.97, 9.28 (bs, 1H), 8.40 (s, 1H), 7.92*, 7.90 (d, 1H, J 8.8), 7.69*, 7.67 (d, 1H, J 8.8), 7.64-7.39 (m, 4H), 5.25 (dd, 1H, J 5.9, 14.0), 5.00* (d, 1H, J 16.4), 4.42-3.94 (m, 3H), 3.64 (m, 2H, part of signal under water peak), 3.01 (s, 3H), 2.94-2.72 (m, 2H), 2.68-2.35 (m, 1H), 2.15-1.92 (m, 3H), 1.91-1.81 (m, 1H), 1.79-1.64 (m, 2H), 1.61-1.48 (m, 1H), 1.47-1.29 (m, 2H), 1.21-1.07 (m, 1H); MS (ES$^+$): 415.7 (M+H$^+$).

The following tables list specific compounds of the present invention. The tables provide the structure and name of each compound and the mass of its molecular ion plus 1 (M+1) as determined via ES-MS. The synthetic scheme employed to prepare the compound is indicated in the last column.

TABLE 1

| | Hexahydrocyclopenta[d]indolo[2,1-a][2]benzazepine inhibitors | | | |
|---|---|---|---|---|
| Example no. | Structure | Chemical name, free base | ES-MS (M + H$^+$) | Synthetic scheme |
| 101 | 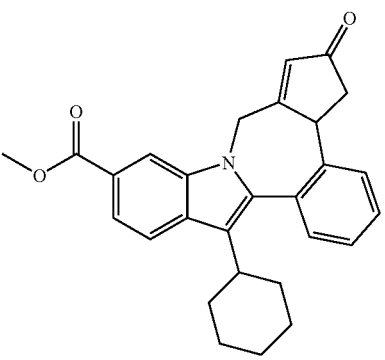 | methyl 10-cyclohexyl-2-oxo-1,2,4,14b-tetrahydrocyclopenta[d]indolo[2,1-a][2]benzazepine-7-carboxylate | 426.4 | A |

TABLE 1-continued

Hexahydrocyclopenta[d]indolo[2,1-a][2]benzazepine inhibitors

| Example no. | Structure | Chemical name, free base | ES-MS (M + H+) | Synthetic scheme |
|---|---|---|---|---|
| 102 | 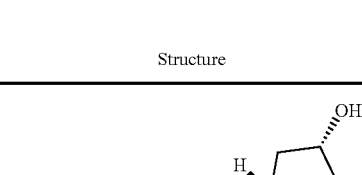 | rel-(2R,3aR,14bS)-10-cyclohexyl-2-hydroxy-1,2,3,3a,4,14b-hexahydrocyclopenta[d]indolo[2,1-a][2]benzazepine-7-carboxylic acid | 416.3 | A |

TABLE 2

Cis-annulated hexahydroindolo[2,1-a]pyrrolo[2,3-d][2]benzazepine inhibitors

| Example no. | Structure | Chemical name, free base | ES-MS (M + H+) | Synthetic scheme |
|---|---|---|---|---|
| 201 | 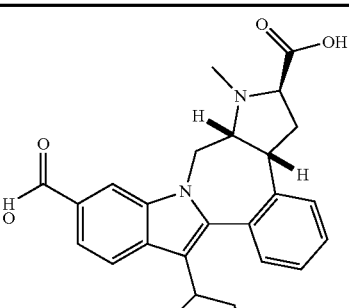 | rel-(2R,3aR,14bR)-10-cyclohexyl-3-methyl-1,2,3,3a,4,14b-hexahydroindolo[2,1-a]pyrrolo[2,3-d][2]benzazepine-2,7-dicarboxylic acid | 459.4 | F |

TABLE 3

Cis-annulated hexahydroindolo[2,1-a]pyrrolo[3,2-d][2]benzazepine inhibitors

| Example no. | Structure | Chemical Name, free base | ES-MS (M + H+) | Synthetic scheme |
|---|---|---|---|---|
| 301 | 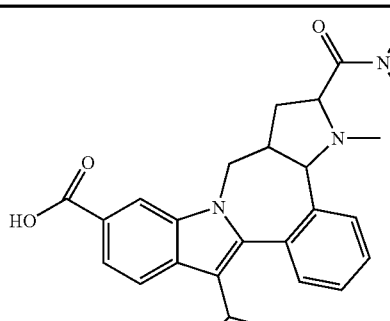 | rel-(3aS,14bS)-7-carboxy-10-cyclohexyl-2-[(dimethylamino)carbonyl]-1-methyl-1,2,3,3a,4,14b-hexahydroindolo[2,1-a]pyrrolo[3,2-d][2]benzazepine | 486.3 | F |

TABLE 3-continued

Cis-annulated hexahydroindolo[2,1-a]pyrrolo[3,2-d][2]benzazepine inhibitors

| Example no. | Structure | Chemical Name, free base | ES-MS (M + H+) | Synthetic scheme |
|---|---|---|---|---|
| 302 | 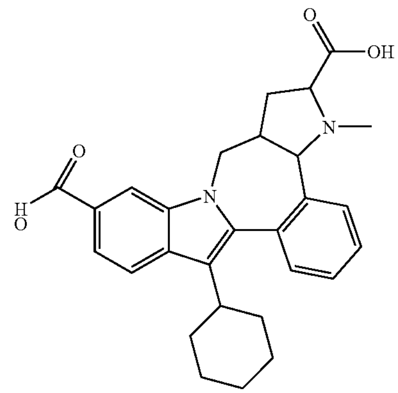 | rel-(3aS,14bS)-2,7-dicarboxy-10-cyclohexyl-1-methyl-1,2,3,3a,4,14b-hexahydroindolo[2,1-a]pyrrolo[3,2-d][2]benzazepine | 459.3 | F |
| 303 | 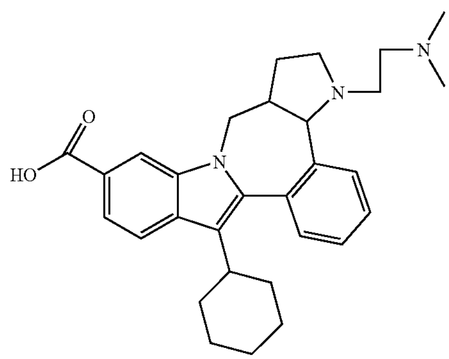 | rel-(3aS,14bS)-7-carboxy-10-cyclohexyl-1-[2-(dimethylamino)ethyl]-1,2,3,3a,4,14b-hexahydroindolo[2,1-a]pyrrolo[3,2-d][2]benzazepine | 472.5 | F |
| 304 | 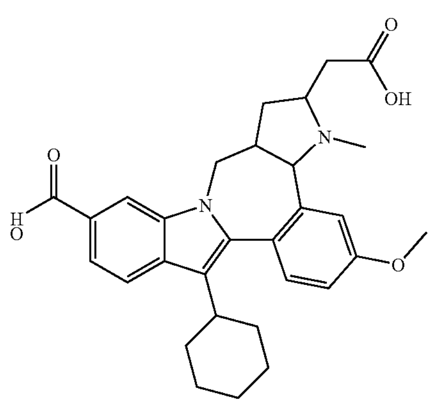 | rel-(3aS,14bS)-2-(carboxymethyl)-10-cyclohexyl-13-methoxy-1-methyl-1,2,3,3a,4,14b-hexahydroindolo[2,1-a]pyrrolo[3,2-d][2]benzazepine-7-carboxylic acid | 503.3 | F |
| 305 | 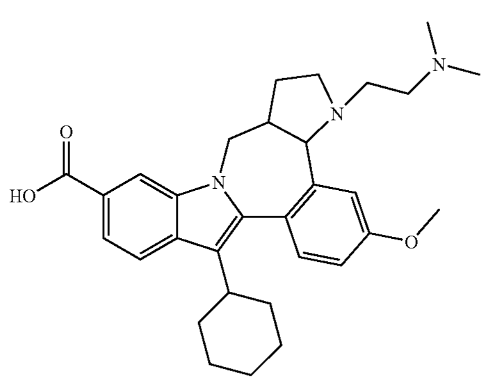 | rel-(3aS,14bS)-7-carboxy-10-cyclohexyl-1-[2-(dimethylamino)ethyl]-13-methoxy-1,2,3,3a,4,14b-hexahydroindolo[2,1-a]pyrrolo[3,2-d][2]benzazepine | 502.5 | F |

TABLE 3-continued

Cis-annulated hexahydroindolo[2,1-a]pyrrolo[3,2-d][2]benzazepine inhibitors

| Example no. | Structure | Chemical Name, free base | ES-MS (M + H⁺) | Synthetic scheme |
|---|---|---|---|---|
| 306 | 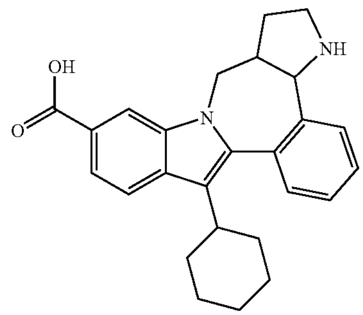 | rel-(3aS,14bS)-7-carboxy-10-cyclohexyl-1,2,3,3a,4,14b-hexahydroindolo[2,1-a]pyrrolo[3,2-d][2]benzazepine | 401.5 | F |
| 307 | 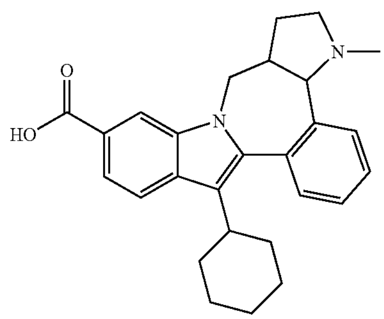 | rel-(3aS,14bS)-7-carboxy-10-cyclohexyl-1-methyl-1,2,3,3a,4,14b-hexahydroindolo[2,1-a]pyrrolo[3,2-d][2]benzazepine | 415.7 | F |
| 308 | 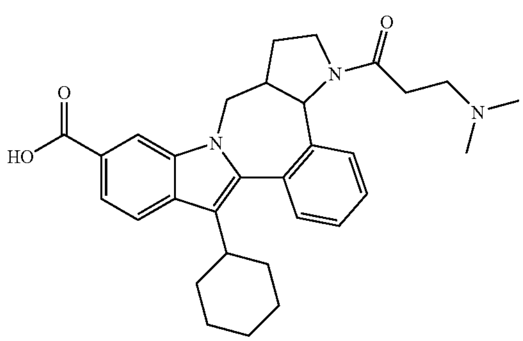 | 3-[rel-(3aS,14bS)-7-carboxy-10-cyclohexyl-2,3,3a,14b-tetrahydroindolo[2,1-a]pyrrolo[3,2-d][2]benzazepin-1(4H)-yl]-N,N-dimethyl-3-oxopropan-1-amine | 500.5 | F |
| 309 | 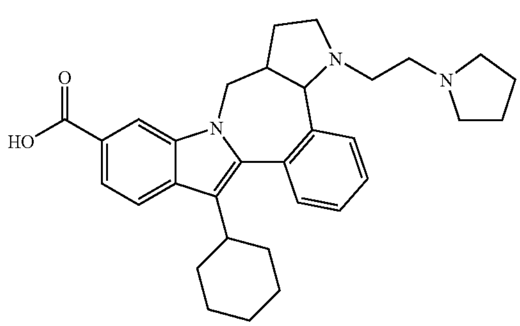 | rel-(3aS,14bS)-7-carboxy-10-cyclohexyl-13-methoxy-1-(2-pyrrolidin-1-ylethyl)-1,2,3,3a,4,14b-hexahydroindolo[2,1-a]pyrrolo[3,2-d][2]benzazepine | 498.5 | F |

TABLE 3-continued

Cis-annulated hexahydroindolo[2,1-a]pyrrolo[3,2-d][2]benzazepine inhibitors

| Example no. | Structure | Chemical Name, free base | ES-MS (M + H+) | Synthetic scheme |
|---|---|---|---|---|
| 310 | 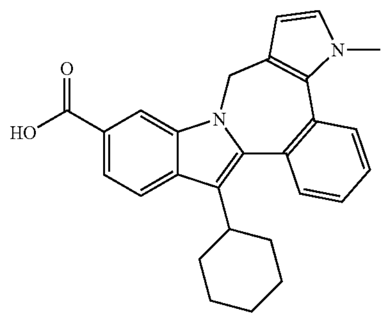 | 10-cyclohexyl-1-methyl-1,4-dihydroindolo[2,1-a]pyrrolo[3,2-d][2]benzazepine-7-carboxylic acid | 411.6 | F |
| 311 | 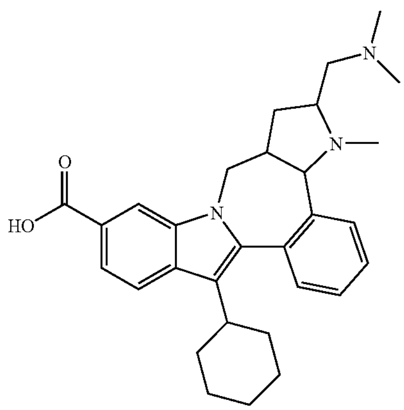 | rel-(3aS,14bS)-7-carboxy-10-cyclohexyl-2-[(dimethylamino)methyl]-13-methoxy-1-methyl-1,2,3,3a,4,14b-hexahydroindolo[2,1-a]pyrrolo[3,2-d][2]benzazepine | 472.6 | F |
| 312 | 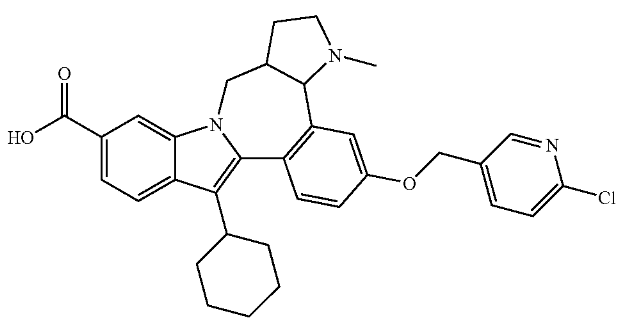 | rel-(3aS,14bS)-7-carboxy-13-[(6-chloropyridin-3-yl)methoxy]-10-cyclohexyl-1-methyl-1,2,3,3a,4,14b-hexahydroindolo[2,1-a]pyrrolo[3,2-d][2]benzazepine | 556.4 | F |
| 313 | 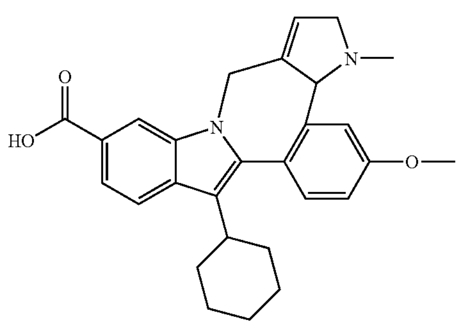 | 7-carboxy-10-cyclohexyl-13-methoxy-1-methyl-1,2,4,14b-tetrahydroindolo[2,1-a]pyrrolo[3,2-d][2]benzazepine | 443.6 | F |

TABLE 3-continued

Cis-annulated hexahydroindolo[2,1-a]pyrrolo[3,2-d][2]benzazepine inhibitors

| Example no. | Structure | Chemical Name, free base | ES-MS (M + H+) | Synthetic scheme |
|---|---|---|---|---|
| 314 | 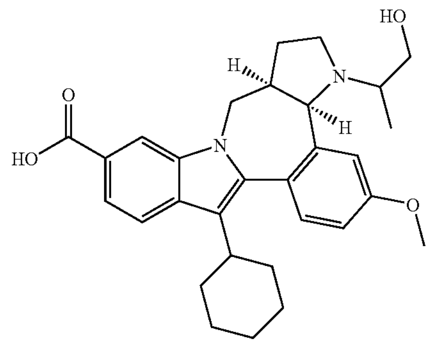 | rel-(3aR,14bR)-10-cyclohexyl-1-(2-hydroxy-1-methylethyl)-13-methoxy-1,2,3,3a,4,14b-hexahydroindolo[2,1-a]pyrrolo[3,2-d][2]benzazepine-7-carboxylic acid | 489.4 | F |

TABLE 4

Trans-annulated hexahydroindolo[2,1-a]pyrrolo[3,2-d][2]benzazepine

| Example no. | Structure | Chemical Name, free base | ES-MS (M + H+) | Synthetic scheme |
|---|---|---|---|---|
| 401 | 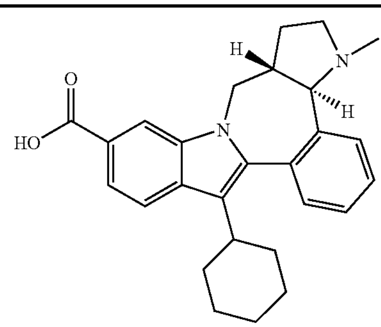 | rel-(3aR,14bS)-7-carboxy-10-cyclohexyl-1-methyl-1,2,3,3a,4,14b-hexahydroindolo[2,1-a]pyrrolo[3,2-d][2]benzazepine | 415.6 | F |
| 402 | 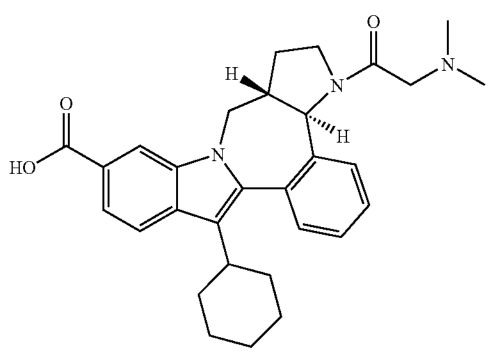 | 2-[rel-(3aR,14bS)-7-carboxy-10-cyclohexyl-2,3,3a,14b-tetrahydroindolo[2,1-a]pyrrolo[3,2-d][2]benzazepin-1(4H)-yl]-N,N-dimethyl-2-oxoethanamine | 486.4 | F |
| 403 | 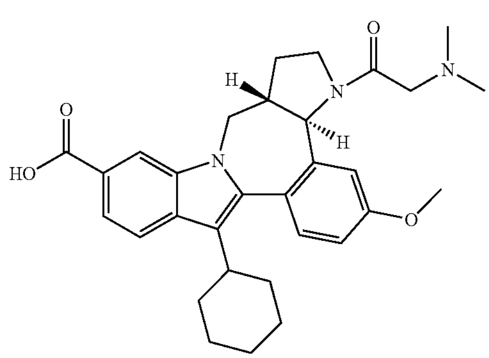 | 2-[rel-(3aR,14bS)-7-carboxy-10-cyclohexyl-13-methoxy-2,3,3a,14b-tetrahydroindolo[2,1-a]pyrrolo[3,2-d][2]benzazepin-1(4H)-yl]-N,N-dimethyl-2-oxoethanamine | 516.6 | F |

TABLE 4-continued

Trans-annulated hexahydroindolo[2,1-a]pyrrolo[3,2-d][2]benzazepine

| Example no. | Structure | Chemical Name, free base | ES-MS (M + H⁺) | Synthetic scheme |
|---|---|---|---|---|
| 404 | 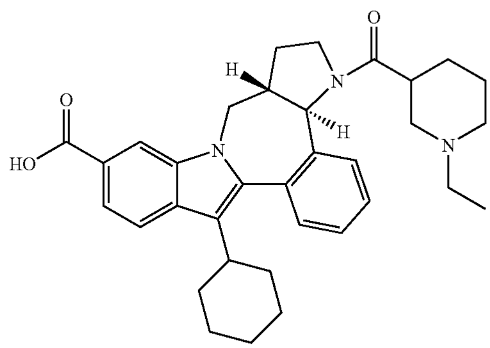 | 3-{[rel-(3aR,14bS)-7-carboxy-10-cyclohexyl-2,3,3a,14b-tetrahydroindolo[2,1-a]pyrrolo[3,2-d][2]benzazepin-1(4H)-yl]carbonyl}-1-ethylpiperidine | 540.6 | F |
| 405 | 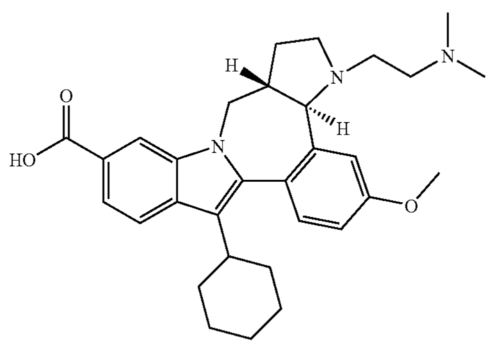 | rel-(3aR,14bS)-10-cyclohexyl-1-[2-(dimethylamino)ethyl]-13-methoxy-1,2,3,3a,4,14b-hexahydroindolo[2,1-a]pyrrolo[3,2-d][2]benzazepine-7-carboxylic acid, enantiomer A | 502.6 | F |
| 406 | 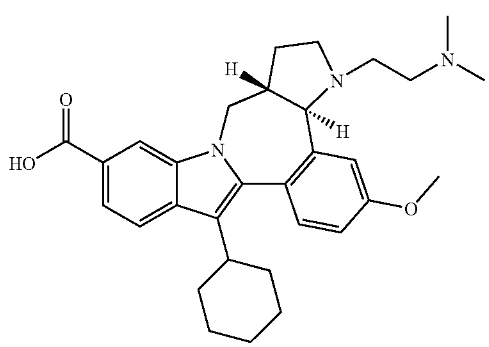 | rel-(3aR,14bS)-10-cyclohexyl-1-[2-(dimethylamino)ethyl]-13-methoxy-1,2,3,3a,4,14b-hexahydroindolo[2,1-a]pyrrolo[3,2-d][2]benzazepine-7-carboxylic acid, enantiomer B | 502.6 | F |
| 407 | 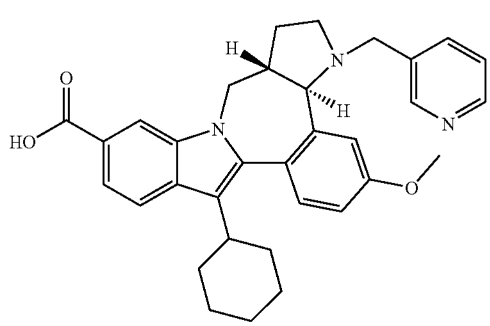 | rel-(3aR,14bS)-7-carboxy-10-cyclohexyl-13-methoxy-1-(pyridin-3-ylmethyl)-1,2,3,3a,4,14b-hexahydroindolo[2,1-a]pyrrolo[3,2-d][2]benzazepine | 522.5 | F |

TABLE 4-continued

Trans-annulated hexahydroindolo[2,1-a]pyrrolo[3,2-d][2]benzazepine

| Example no. | Structure | Chemical Name, free base | ES-MS (M + H$^+$) | Synthetic scheme |
|---|---|---|---|---|
| 408 | 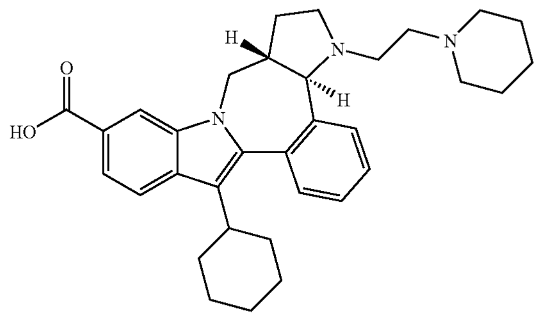 | rel-(3aS,14bR)-10-cyclohexyl-1-(2-piperidin-1-ylethyl)-1,2,3,3a,4,14b-hexahydroindolo[2,1-a]pyrrolo[3,2-d][2]benzazepine-7-carboxylic acid | 512.5 | F |
| 409 | 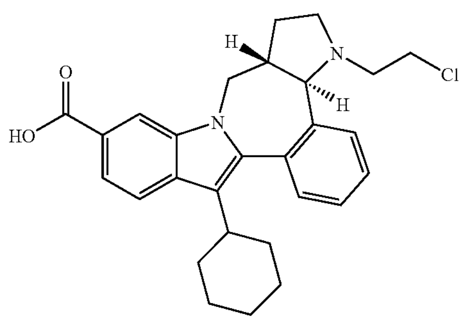 | trans-1-(2-chloroethyl)-10-cyclohexyl-1,2,3,3a,4,14b-hexahydroindolo[2,1-a]pyrrolo[3,2-d][2]benzazepine-7-carboxylic acid | 463.3 | F |
| 410 | 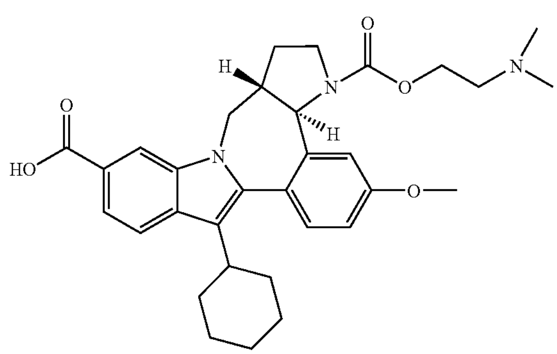 | rel-(3aS,14bR)-10-cyclohexyl-1-{[2-(dimethylamino)ethoxy]carbonyl}-13-methoxy-1,2,3,3a,4,14b-hexahydroindolo[2,1-a]pyrrolo[3,2-d][2]benzazepine-7-carboxylic acid | 546.5 | F |
| 411 | 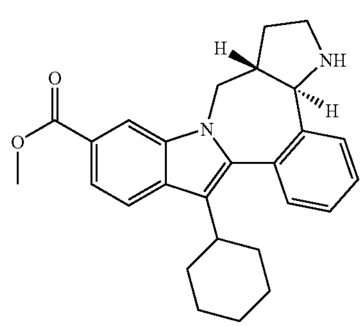 | methyl rel-(3aS,14bR)-10-cyclohexyl-1,2,3,3a,4,14b-hexahydroindolo[2,1-a]pyrrolo[3,2-d][2]benzazepine-7-carboxylate (racemic mixture) | 415.4 | F |

TABLE 4-continued

Trans-annulated hexahydroindolo[2,1-a]pyrrolo[3,2-d][2]benzazepine

| Example no. | Structure | Chemical Name, free base | ES-MS (M + H+) | Synthetic scheme |
|---|---|---|---|---|
| 412 | 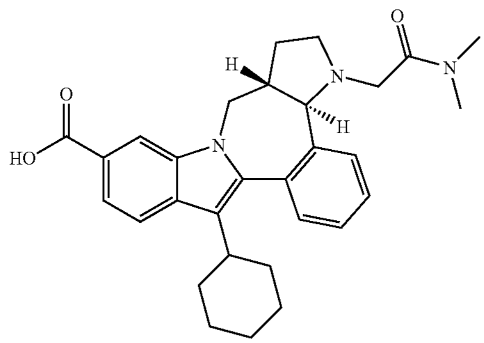 | rel-(3aS,14bR)-10-cyclohexyl-1-[2-(dimethylamino)-2-oxoethyl]-1,2,3,3a,4,14b-hexahydroindolo[2,1-a]pyrrolo[3,2-d][2]benzazepine-7-carboxylic acid | 486.4 | F |
| 413 | 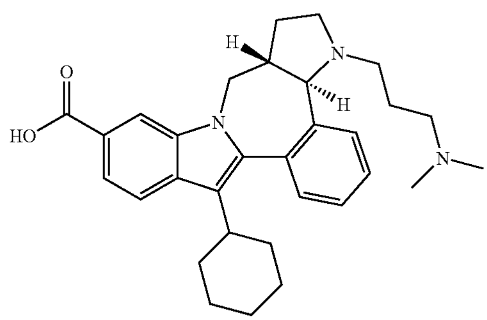 | rel-(3aS,14bR)-10-cyclohexyl-1-[3-(dimethylamino)propyl]-1,2,3,3a,4,14b-hexahydroindolo[2,1-a]pyrrolo[3,2-d][2]benzazepine-7-carboxylic acid | 486.5 | F |
| 414 | 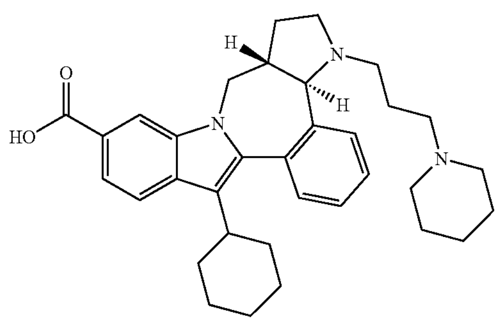 | rel-(3aS,14bR)-10-cyclohexyl-1-(3-piperidin-1-ylpropyl)-1,2,3,3a,4,14b-hexahydroindolo[2,1-a]pyrrolo[3,2-d][2]benzazepine-7-carboxylic acid | 526.6 | F |
| 415 | 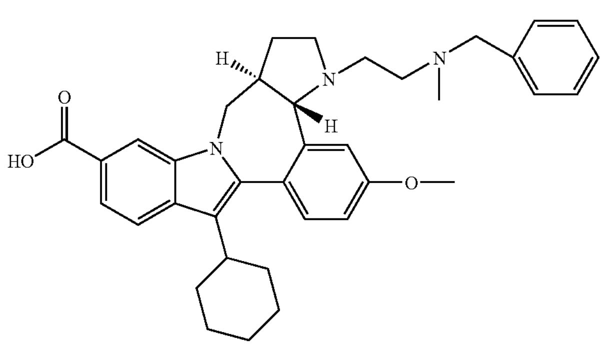 | rel-(3aR,14bS)-1-{2-[benzyl(methyl)amino]ethyl}-10-cyclohexyl-13-methoxy-1,2,3,3a,4,14b-hexahydroindolo[2,1-a]pyrrolo[3,2-d][2]benzazepine-7-carboxylic acid | 578.5 | F |

TABLE 4-continued

Trans-annulated hexahydroindolo[2,1-a]pyrrolo[3,2-d][2]benzazepine

| Example no. | Structure | Chemical Name, free base | ES-MS (M + H+) | Synthetic scheme |
|---|---|---|---|---|
| 416 | 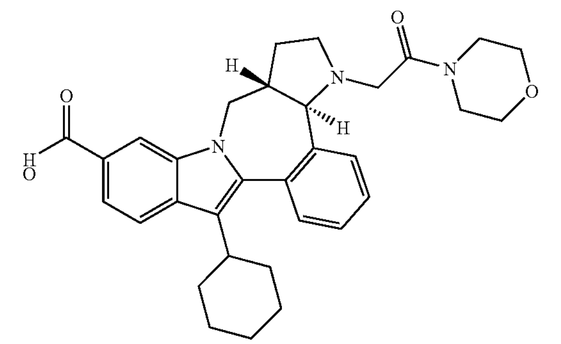 | rel-(3aS,14bR)-10-cyclohexyl-1-(2-morpholin-4-yl-2-oxoethyl)-1,2,3,3a,4,14b-hexahydroindolo[2,1-a]pyrrolo[3,2-d][2]benzazepine-7-carboxylic acid | 528.4 | |
| 417 | 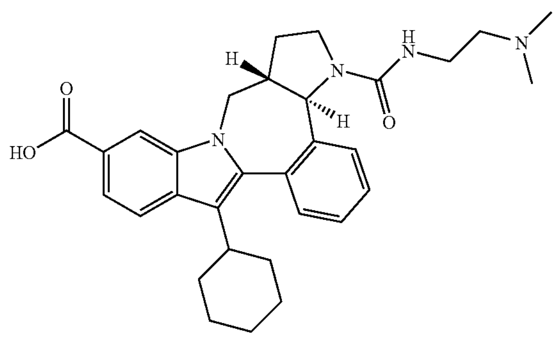 | rel-(3aS,14bR)-10-cyclohexyl-1-({[2-(dimethylamino)ethyl]amino}-carbonyl)-1,2,3,3a,4,14b-hexahydroindolo[2,1-a]pyrrolo[3,2-d][2]benzazepine-7-carboxylic acid | 515.3 | F |
| 418 | 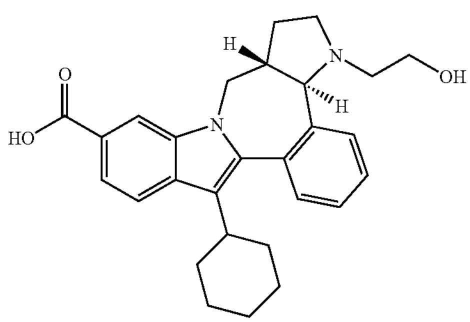 | rel-(3aS,14bR)-10-cyclohexyl-1-(2-hydroxyethyl)-1,2,3,3a,4,14b-hexahydroindolo[2,1-a]pyrrolo[3,2-d][2]benzazepine-7-carboxylic acid | 445.4 | F |
| 419 | 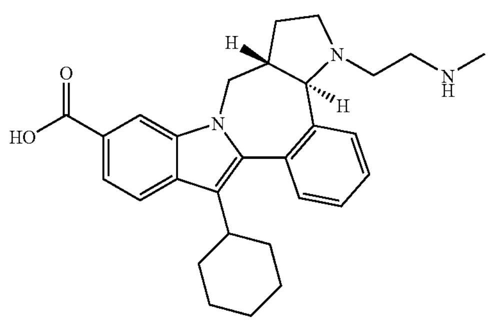 | rel-(3aS,14bR)-10-cyclohexyl-1-[2-(methylamino)ethyl]-1,2,3,3a,4,14b-hexahydroindolo[2,1-a]pyrrolo[3,2-d][2]benzazepine-7-carboxylic acid | 458.4 | F |

TABLE 4-continued

Trans-annulated hexahydroindolo[2,1-a]pyrrolo[3,2-d][2]benzazepine

| Example no. | Structure | Chemical Name, free base | ES-MS (M + H$^+$) | Synthetic scheme |
|---|---|---|---|---|
| 420 | 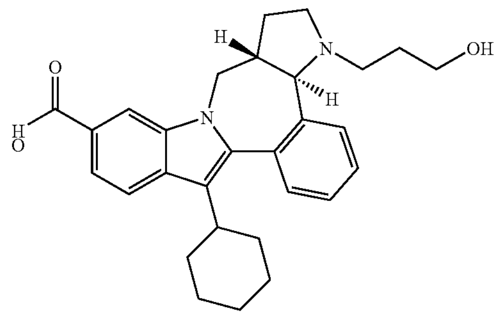 | rel-(3aS,14bR)-10-cyclohexyl-1-(3-hydroxypropyl)-1,2,3,3a,4,14b-hexahydroindolo[2,1-a]pyrrolo[3,2-d][2]benzazepine-7-carboxylic acid | 459.5 | F |

TABLE 5

Spirocyclic Inhibitors

| Example no. | Structure | Chemical Name, free base | ES-MS (M + H$^+$) | Synthetic scheme |
|---|---|---|---|---|
| 501 | 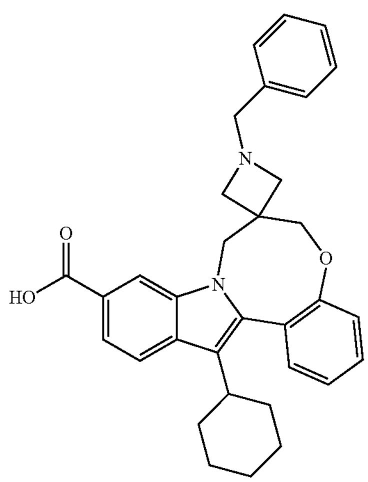 | 1-benzyl-14'-cyclohexylspiro[azetidine-3,7'-indolo[1,2-e][1,5]benzoxazocine]-11'-carboxylic acid | 507 | B |
| 502 | 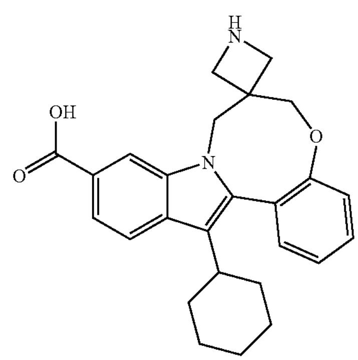 | 14'-cyclohexylspiro[azetidine-3,7'-indolo[1,2-e][1,5]benzoxazocine]-11'-carboxylic acid | 417 | B |

TABLE 5-continued

Spirocyclic Inhibitors

| Example no. | Structure | Chemical Name, free base | ES-MS (M + H+) | Synthetic scheme |
|---|---|---|---|---|
| 503 | 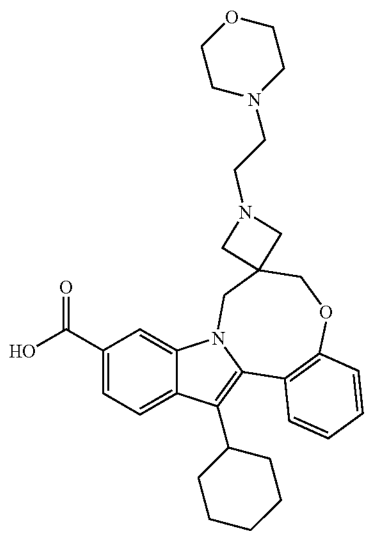 | 14'-cyclohexyl-1-(2-morpholin-4-ylethyl)spiro[azetidine-3,7'-indolo[1,2-e][1,5]benzoxazocine]-11'-carboxylic acid | 530 | B |
| 504 | 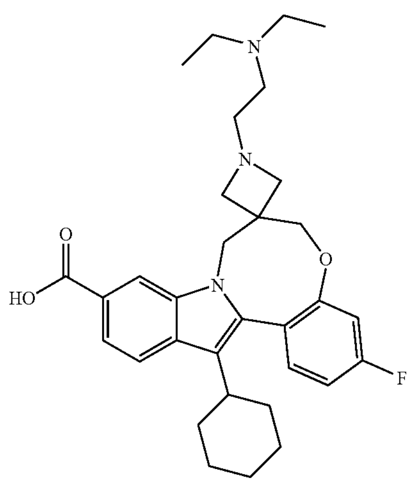 | 14'-cyclohexyl-1-[2-(diethylamino)ethyl]-3'-fluorospiro[azetidine-3,7'-indolo[1,2-e][1,5]benzoxazocine]-11'-carboxylic acid | 534 | B |
| 505 | 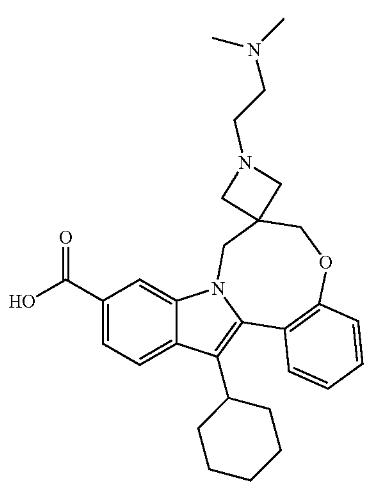 | 14'-cyclohexyl-1-[2-(dimethylamino)ethyl]spiro[azetidine-3,7'-indolo[1,2-e][1,5]benzoxazocine]-11'-carboxylic acid | 488 | B |

TABLE 5-continued

Spirocyclic Inhibitors

| Example no. | Structure | Chemical Name, free base | ES-MS (M + H+) | Synthetic scheme |
|---|---|---|---|---|
| 506 | 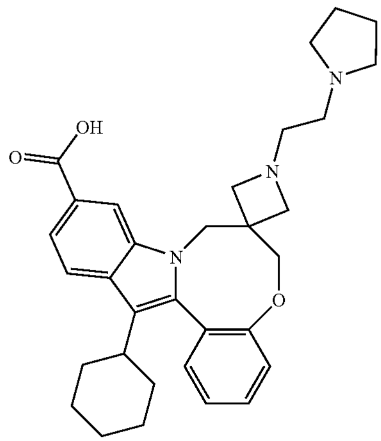 | 14'-cyclohexyl-1-(2-pyrrolidin-1-ylethyl)spiro[azetidine-3,7'-indolo[1,2-e][1,5]benzoxazocine]-11'-carboxylic acid | 514 | B |
| 507 | 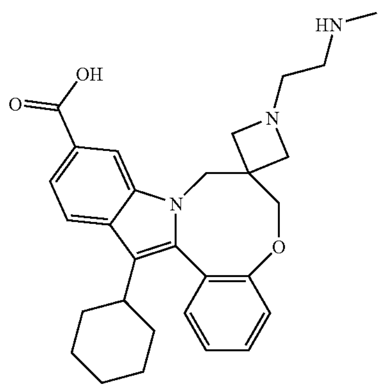 | 14'-cyclohexyl-1-[2-(methylamino)ethyl]spiro[azetidine-3,7'-indolo[1,2-e][1,5]benzoxazocine]-11'-carboxylic acid | 474 | B |
| 508 | 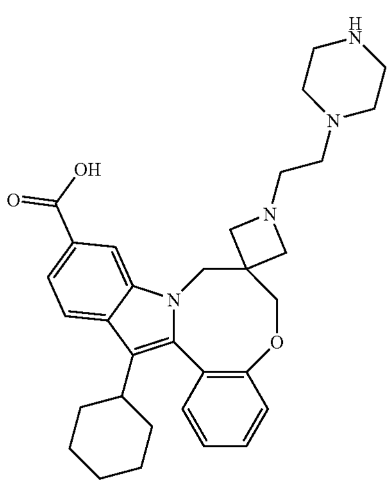 | 14'-cyclohexyl-1-(2-piperazin-1-ylethyl)spiro[azetidine-3,7'-indolo[1,2-e][1,5]benzoxazocine]-11'-carboxylic acid | 529 | B |

TABLE 5-continued

Spirocyclic Inhibitors

| Example no. | Structure | Chemical Name, free base | ES-MS (M + H⁺) | Synthetic scheme |
|---|---|---|---|---|
| 509 | 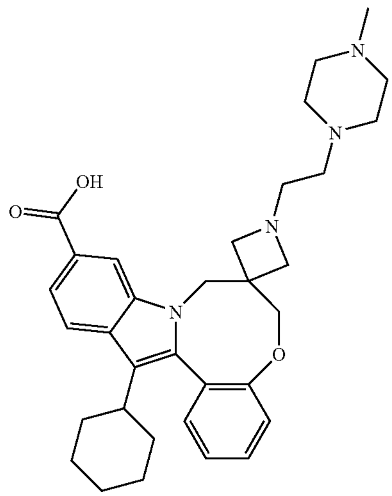 | 14'-cyclohexyl-1-[2-(4-methylpiperazin-1-yl)ethyl]spiro[azetidine-3,7'-indolo[1,2-e][1,5]benzoxazocine]-11'-carboxylic acid | 543 | B |
| 510 | 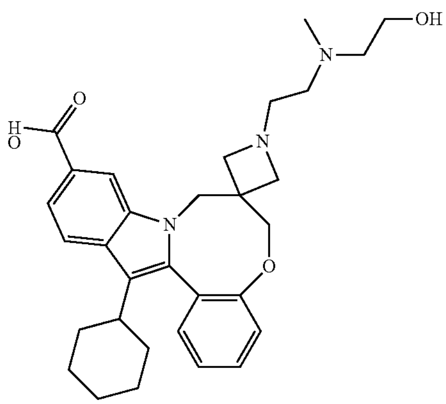 | 11'-carboxy-14'-cyclohexyl-1-{2-[(2hydroxyethyl)(methyl)-amino]-ethyl}-spiro[azetidine-3,7'-indolo[1,2-e][1,5]benzoxazocine] | 518 | B |
| 511 | 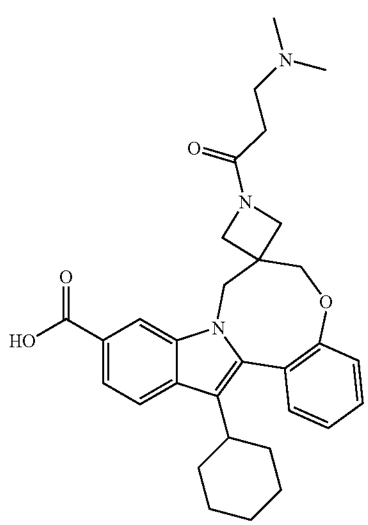 | 14'-cyclohexyl-1-(N,N-dimethyl-beta-alanyl)spiro[azetidine-3,7'-indolo[1,2-e][1,5]benzoxazocine]-11'-carboxylic acid | 516 | B |

TABLE 5-continued

Spirocyclic Inhibitors

| Example no. | Structure | Chemical Name, free base | ES-MS (M + H+) | Synthetic scheme |
|---|---|---|---|---|
| 512 | 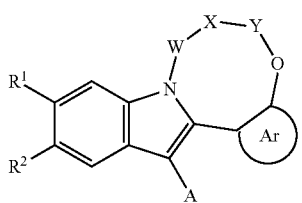 | 14'-cyclohexyl-1-(N,N-dimethylglycyl)spiro[azetidine-3,7'-indolo[1,2-e][1,5]benzoxazocine]-11'-carboxylic acid | 502 | B |

The invention claimed is:
1. A compound of formula (I):

(I)

or a pharmaceutically acceptable salt thereof,
wherein
A is $C_{3-8}$cycloalkyl, optionally substituted by halogen, hydroxy, $C_{1-4}$alkyl or $C_{1-4}$alkoxy;
Ar is a moiety containing at least one aromatic ring and possesses 5, 6, 9 or 10 ring atoms, optionally containing 1, 2 or 3 heteroatoms independently selected from N, O and S, which ring is optionally substituted by groups $Q^1$ and $Q^2$;
$Q^1$ is halogen, hydroxy, $C_{1-6}$alkyl, $C_{1-6}$alkoxy, $(CH_2)_{0-3}$aryl, $(CH_2)_{0-3}$heteroaryl, $CONR^cR^d$, $(CH_2)_{0-3}NR^cR^d$, $O(CH_2)_{0-3}C_{3-8}$cycloalkyl, $O(CH_2)_{1-3}NR^cR^d$, $O(CH_2)_{0-3}$ $CONR^cR^d$, $O(CH_2)_{0-3}CO_2H$, $O(CH_2)_{0-3}$aryl, $O(CH_2)_{0-3}$heteroaryl, $OCHR^eR^f$ or $O(CH_2)_{0-3}S(O)_2$ $(CH_2)_{0-3}NR^cR^d$, where heteroaryl is optionally substituted by halogen or hydroxy;
$R^c$ and $R^d$ are independently selected from hydrogen, $C_{1-6}$alkyl and $C(O)C_{1-6}$alkyl;
or $R^c$ and $R^d$, together with the nitrogen atom to which they are attached, form a heteroaliphatic ring of 4 to 7 ring atoms, optionally containing 1 or 2 more heteroatoms independently selected from O and S and/or 1 or 2 groups independently selected from NH and $NC_{1-4}$alkyl, where said ring is optionally substituted by halogen, hydroxy, $C_{1-4}$alkyl or $C_{1-4}$alkoxy;
$R^e$ and $R^f$ are independently selected from hydrogen, $C_{1-4}$alkyl and $C_{1-4}$alkoxy;
or $R^e$ and $R^f$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;
and where said $C_{1-4}$alkyl, $C_{1-4}$alkoxy and aryl groups are optionally substituted by halogen or hydroxy;
$Q^2$ is halogen, hydroxy, $C_{1-4}$alkyl or $C_{1-4}$alkoxy, where said $C_{1-4}$alkyl and $C_{1-4}$alkoxy groups are optionally substituted by halogen or hydroxy;
or $Q^1$ and $Q^2$ may be linked to form a ring of 4 to 7 atoms, where said ring optionally contains 1 or 2 heteroatoms independently selected from N, O and S, and is optionally substituted by halogen, hydroxy, $C_{1-4}$alkyl or $C_{1-4}$alkoxy;
one of $R^1$ and $R^2$ is $CO_2H$, $CO_2C_{1-6}$alkyl, $C(O)NHS(O)_2$ $NR^aR^b$, $C(O)NHS(O)_2C_{1-6}$alkyl, $C(O)NHS(O)_2$ $(CH_2)_{0-3}CO_2R^e$, $C(O)NHS(O)_2(CH_2)_{0-3}$aryl, tetrazolyl or hydroxyoxadiazolyl,
and the other of $R^1$ and $R^2$ is hydrogen;
$R^a$ and $R^b$ are independently selected from hydrogen and $C_{1-6}$alkyl,
or $R^a$ and $R^b$, together with the nitrogen atom to which they are attached, form a heteroaliphatic ring of 4 to 7 ring atoms, which ring may optionally contain 1 or 2 more heteroatoms independently selected from O and S and/ or 1 or 2 groups independently selected from S(O), $S(O)_2$, NH and $NC_{1-4}$alkyl;
W is $—CH_2—$ or $—CH_2CH_2—$;
Z is a bond, O or $—CH_2—$;
X is $—CR^{14}R^{15}$;
Y is $—CH_2—$ or $—CH_2CH_2—$;
$R^{14}$ and $R^{15}$, together with the carbon atom to which they are attached, form a heteroaliphatic ring of 4 to 7 ring atoms, which ring contains 1 or 2 heteroatoms selected from O and S, and/or 1 or 2 groups independently selected from S(O), $S(O)_2$ and $NR^{16}$ and which ring is optionally substituted by halogen, hydroxy, $C_{1-4}$alkyl or $C_{1-4}$alkoxy;
$R^{16}$ is hydrogen, $C_{1-6}$alkyl, $C_{2-6}$alkenyl, $C_{2-6}$alkynyl, $(CH_2)_{0-3}$-phenyl, $(CH_2)_{1-3}NR^{17}R^{18}$ or $C(O)(CH_2)_{1-3}$ $NR^{17}R^{18}$; and $R^{17}$ and $R^{18}$ are independently selected from hydrogen, $C_{1-4}$alkyl or $(CH_2)_{1-3}OH$, or $R^{17}$ and $R^{18}$, together with the nitrogen atom to which they are attached, form a heteroaliphatic ring of 4 to 7 atoms, which ring may optionally contain 1 or 2 more heteroatoms selected from O and S and/or 1 or 2 groups independently selected from $S(O)$, $S(O)_2$, NH or $NC_{1-4}$alkyl, and which ring is optionally substituted by halogen, hydroxy, $C_{1-4}$alkyl or $C_{1-4}$alkoxy.

2. The compound as claimed in claim 1, wherein the compound is a compound of formula (Io):

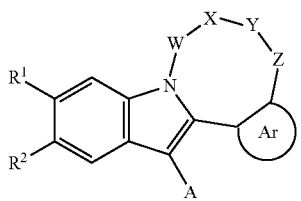

(Io)

or a pharmaceutically acceptable salt thereof,
wherein
A is $C_{3-8}$cycloalkyl, optionally substituted by halogen, hydroxy, $C_{1-4}$alkyl or $C_{1-4}$alkoxy;
Ar is a moiety containing at least one aromatic ring and possesses 5, 6, 9 or 10 ring atoms, optionally containing 1, 2 or 3 heteroatoms independently selected from N, O and S, which ring is optionally substituted by groups $Q^1$ and $Q^2$;
$Q^1$ is halogen, hydroxy, $C_{1-6}$alkyl, $C_{1-6}$alkoxy, $(CH_2)_{0-3}$aryl, $(CH_2)_{0-3}$heteroaryl, $CONR^cR^d$, $(CH_2)_{0-3}NR^cR^d$, $O(CH_2)_{0-3}C_{3-8}$cycloalkyl, $O(CH_2)_{1-3}NR^cR^d$, $O(CH_2)_{0-3} CONR^cR^d$, $O(CH_2)_{0-3}CO_2H$, $O(CH_2)_{0-3}$aryl, $O(CH_2)_{0-3}$heteroaryl, $OCHR^eR^f$ or $O(CH_2)_{0-3}S(O)_2(CH_2)_{0-3}NR^cR^d$;
$R^c$ and $R^d$ are independently selected from hydrogen, $C_{1-6}$alkyl and $C(O)C_{1-6}$alkyl;
or $R^c$ and $R^d$, together with the nitrogen atom to which they are attached, form a heteroaliphatic ring of 4 to 7 ring atoms, optionally containing 1 or 2 more heteroatoms independently selected from O and S and/or 1 or 2 groups independently selected from NH and $NC_{1-4}$alkyl, where said ring is optionally substituted by halogen, hydroxy, $C_{1-4}$alkyl or $C_{1-4}$alkoxy;
$R^e$ and $R^f$ are independently selected from hydrogen, $C_{1-4}$alkyl and $C_{1-4}$alkoxy;
or $R^e$ and $R^f$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy, wherein said $C_{1-4}$alkyl, $C_{1-4}$alkoxy and aryl groups are optionally substituted by halogen or hydroxy;
$Q^2$ is halogen, hydroxy, $C_{1-4}$alkyl or $C_{1-4}$alkoxy, where said $C_{1-4}$alkyl and $C_{1-4}$alkoxy groups are optionally substituted by halogen or hydroxy;
or $Q^1$ and $Q^2$ may be linked to form a ring of 4 to 7 atoms, where said ring optionally contains 1 or 2 heteroatoms independently selected from N, O and S, and is optionally substituted by halogen, hydroxy, $C_{1-4}$alkyl or $C_{1-4}$alkoxy;
one of $R^1$ and $R^2$ is $CO_2H$, $CO_2C_{1-6}$alkyl, $C(O)NHS(O)_2NR^aR^b$, $C(O)NHS(O)_2C_{1-6}$alkyl, $C(O)NHS(O)_2(CH_2)_{0-3}CO_2R^c$, $C(O)NHS(O)_2(CH_2)_{0-3}$aryl, tetrazolyl or hydroxyoxadiazolyl, and the other of $R^1$ and $R^2$ is hydrogen;
$R^a$ and $R^b$ are independently selected from hydrogen and $C_{1-6}$alkyl,
or $R^a$ and $R^b$, together with the nitrogen atom to which they are attached, form a heteroaliphatic ring of 4 to 7 ring atoms, which ring may optionally contain 1 or 2 more heteroatoms independently selected from O and S and/or 1 or 2 groups independently selected from $S(O)$, $S(O)_2$, NH and $NC_{1-4}$alkyl;
W is $—CH_2—$ or $—CH_2CH_2—$;
Z is a bond, O or $—CH_2—$;
or Z and $Q^1$ are joined to form a non-aliphatic 5- or 6-membered ring optionally containing 1, 2 or 3 heteroatoms selected from N, O and S, which ring is optionally substituted by $C_{1-6}$alkyl;
X is $—CR^{14}R^{15}$;
Y is $—CH_2—$ or $—CH_2CH_2—$;
$R^{14}$ and $R^{15}$, together with the carbon atom to which they are attached, form a heteroaliphatic ring of 4 to 7 ring atoms, which ring contains 1 or 2 heteroatoms selected from O and S, and/or 1 or 2 groups independently selected from $S(O)$, $S(O)_2$ and $NR^{16}$ and which ring is optionally substituted by halogen, hydroxy, $C_{1-4}$alkyl or $C_{1-4}$alkoxy;
$R^{16}$ is hydrogen, $C_{1-6}$alkyl, $C_{2-6}$alkenyl, $C_{2-6}$alkynyl, $(CH_2)_{0-3}$-phenyl or $(CH_2)_{1-3}NR^{17}R^{18}$;
$R^{17}$ and $R^{18}$ are independently selected from hydrogen, $C_{1-4}$alkyl or $(CH_2)_{1-3}OH$;
or $R^{17}$ and $R^{18}$, together with the nitrogen atom to which they are attached, form a heteroaliphatic ring of 4 to 7 atoms, which ring may optionally contain 1 or 2 more heteroatoms selected from O and S and/or 1 or 2 groups independently selected from $S(O)$, $S(O)_2$, NH or $NC_{1-4}$alkyl, and which ring is optionally substituted by halogen, hydroxy, $C_{1-4}$alkyl or $C_{1-4}$alkoxy.

3. The compound as claimed in claim 1, wherein A is $C_{3-8}$cycloalkyl.

4. The compound as claimed in claim 1, wherein Ar is a 5- or 6-membered aromatic ring optionally containing 1 or 2 heteroatoms independently selected from N, O and S, which ring is optionally substituted by $Q^1$.

5. The compound as claimed in claim 1, wherein one of $R^1$ and $R^2$ is $CO_2H$ or $CO_2C_{1-6}$alkyl and the other of $R^1$ and $R^2$ is hydrogen.

6. The compound as claimed in claim 1, wherein W is $—CH_2—$.

7. The compound as claimed in claim 1, wherein Z is a bond or O.

8. The compound as claimed in claim 1, wherein Y is $—CH_2—$.

9. The compound as claimed in claim 1, wherein said compound is a compound of formula (Ia):

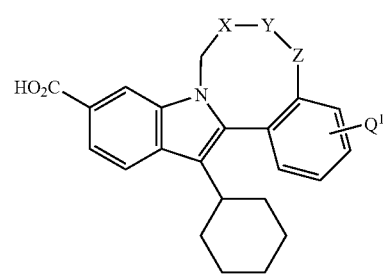

(Ia)

or a pharmaceutically acceptable salt thereof.

10. The compound as claimed in claim 1, wherein the compound is selected from the group consisting of:
14'-cyclohexyl-1-isopropylspiro[azetidine-3,7'-indolo[1,2-e][1,5]benzoxazocine]-11'-carboxylic acid,
14-cyclohexylspiro[indolo[1,2-e][1,5]benzoxazocine-7,3'-oxetane]-11-carboxylic acid,
14'-cyclohexyl-1-[2-(diethylamino)ethyl]spiro[azetidine-3,7'-indolo[1,2-e][1,5]benzoxazocine]-11'-carboxylic acid,
14'-cyclohexyl-1-(N,N-dimethyl-β-alanyl)spiro[azetidine-3,7'-indolo[1,2-e][1,5]benzoxazocine]-11'-carboxylic acid,
(7R)-14-cyclohexyl-1'-methylspiro[indolo[1,2-e][1,5]benzoxazocine-7,2'-pyrrolidine]-11-carboxylic acid,
1-benzyl-14'-cyclohexylspiro[azetidine-3,7'-indolo[1,2-e][1,5]benzoxazocine]-11'-carboxylic acid,
14'-cyclohexylspiro[azetidine-3,7'-indolo[1,2-e][1,5]benzoxazocine]-11'-carboxylic acid
14'-cyclohexyl-1-(2-morpholin-4-ylethyl)spiro[azetidine-3,7'-indolo[1,2-e][1,5]benzoxazocine]-11'-carboxylic acid,
14'-cyclohexyl-1-[2-(diethylamino)ethyl]-3'-fluorospiro[azetidine-3,7'-indolo[1,2-e][1,5]benzoxazocine]-11'-carboxylic acid,
14'-cyclohexyl-1-[2-(dimethylamino)ethyl]spiro[azetidine-3,7'-indolo[1,2-e][1,5]benzoxazocine]-11'-carboxylic acid,
14'-cyclohexyl-1-(2-pyrrolidin-1-ylethyl)spiro[azetidine-3,7'-indolo[1,2-e][1,5]benzoxazocine]-11'-carboxylic acid,
14'-cyclohexyl-1-[2-(methylamino)ethyl]spiro[azetidine-3,7'-indolo[1,2-e][1,5]benzoxazocine]-11'-carboxylic acid,
14'-cyclohexyl-1-(2-piperazin-1-ylethyl)spiro[azetidine-3,7'-indolo[1,2-e][1,5]benzoxazocine]-11'-carboxylic acid,
14'-cyclohexyl-1-[2-(4-methylpiperazin-1-yl)ethyl]spiro[azetidine-3,7'-indolo[1,2-e][1,5]benzoxazocine]-11'-carboxylic acid,
11'-carboxy-14'-cyclohexyl-1-{2-[(2-hydroxyethyl)(methyl)amino]ethyl}spiro[azetidine-3,7'-indolo[1,2-e][1,5]benzoxazocine],
14'-cyclohexyl-1-(N,N-dimethyl-beta-alanyl)spiro[azetidine-3,7'-indolo[1,2-e][1,5]benzoxazocine]-11'-carboxylic acid and
14'-cyclohexyl-1-(N,N-dimethylglycyl)spiro[azetidine-3,7'-indolo[1,2-e][1,5]benzoxazocine]-11'-carboxylic acid,
and pharmaceutically acceptable salts thereof.

11. A pharmaceutical composition comprising a compound of claim 1, or a pharmaceutically acceptable salt thereof, in association with a pharmaceutically acceptable carrier.

12. The pharmaceutical composition as claimed in claim 11, further comprising one or more other agents for the treatment of viral infections or an immunomodulatory agent.

* * * * *